United States Patent
Young et al.

(10) Patent No.: US 9,624,276 B2
(45) Date of Patent: Apr. 18, 2017

(54) PEPTIDIC CHIMERIC ANTIGEN RECEPTOR T CELL SWITCHES AND USES THEREOF

(71) Applicant: The California Institute for Biomedical Research, La Jolla, CA (US)

(72) Inventors: Travis Young, La Jolla, CA (US); Chanhyuk Kim, San Diego, CA (US); Peter G. Schultz, La Jolla, CA (US)

(73) Assignee: The California Institute for Biomedical Research, La Jolla, CA (US)

( * ) Notice: Subject to any disclaimer, the term of this patent is extended or adjusted under 35 U.S.C. 154(b) by 0 days.

(21) Appl. No.: 14/688,894

(22) Filed: Apr. 16, 2015

(65) Prior Publication Data

US 2015/0307564 A1 Oct. 29, 2015

Related U.S. Application Data

(63) Continuation of application No. PCT/US2014/060684, filed on Oct. 15, 2014.

(60) Provisional application No. 62/030,514, filed on Jul. 29, 2014, provisional application No. 62/030,526, filed on Jul. 29, 2014, provisional application No. 62/009,054, filed on Jun. 6, 2014, provisional application No. 61/895,704, filed on Oct. 25, 2013, provisional application No. 61/891,347, filed on Oct. 15, 2013.

(51) Int. Cl.
| | | |
|---|---|---|
| C07K 14/395 | (2006.01) | |
| C07K 14/00 | (2006.01) | |
| C07K 16/00 | (2006.01) | |
| A61K 39/00 | (2006.01) | |
| C12N 5/10 | (2006.01) | |
| C07K 19/00 | (2006.01) | |
| C12N 5/0783 | (2010.01) | |
| A61K 38/00 | (2006.01) | |

(52) U.S. Cl.
CPC .......... C07K 14/395 (2013.01); C12N 5/0636 (2013.01); *A61K 38/00* (2013.01); *C07K 2319/01* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,372,930 A | 12/1994 | Colton et al. | |
| 5,861,156 A | 1/1999 | George et al. | |
| 5,906,936 A | 5/1999 | Eshhar et al. | |
| 5,912,172 A | 6/1999 | Eshhar et al. | |
| 6,083,751 A | 7/2000 | Feldhaus et al. | |
| 7,258,986 B2 | 8/2007 | Maur et al. | |
| 7,446,190 B2 | 11/2008 | Sadelain et al. | |
| 7,514,537 B2 | 4/2009 | Jensen | |
| 8,802,374 B2 | 8/2014 | Jensen | |
| 8,916,381 B1 | 12/2014 | June et al. | |
| 2004/0044177 A1 | 3/2004 | Macke et al. | |
| 2004/0072299 A1* | 4/2004 | Gillies ................. | A61K 38/193 435/69.5 |
| 2005/0113564 A1 | 5/2005 | Campana et al. | |
| 2005/0129671 A1 | 6/2005 | Cooper et al. | |
| 2006/0083683 A1* | 4/2006 | Hsei .................... | A61K 39/3955 424/1.49 |
| 2007/0172504 A1 | 7/2007 | Shirwan et al. | |
| 2008/0260731 A1* | 10/2008 | Bernett .............. | C07K 16/2803 424/133.1 |
| 2009/0117108 A1 | 5/2009 | Wang et al. | |
| 2010/0178276 A1* | 7/2010 | Sadelain ............ | A61K 39/0011 424/93.7 |
| 2010/0278830 A1 | 11/2010 | Shoemaker et al. | |
| 2010/0297076 A1* | 11/2010 | Morrison ............. | A61K 38/212 424/85.6 |
| 2010/0324008 A1 | 12/2010 | Low et al. | |
| 2012/0034223 A1 | 2/2012 | Hall et al. | |
| 2012/0213783 A1 | 8/2012 | Rosenberg et al. | |
| 2014/0065171 A1 | 3/2014 | Geierstanger et al. | |
| 2014/0234348 A1 | 8/2014 | Scholler et al. | |

FOREIGN PATENT DOCUMENTS

| | | | | |
|---|---|---|---|---|
| DE | WO 2008025558 A2 * | 3/2008 | ......... | C07K 14/4702 |
| WO | WO 97/15669 A1 | 5/1997 | | |
| WO | WO 2004/106380 | 12/2004 | | |
| WO | WO 2007/059312 | 5/2007 | | |
| WO | WO 2007/070659 | 6/2007 | | |
| WO | WO 2007/079130 | 7/2007 | | |
| WO | WO 2007/094916 | 8/2007 | | |
| WO | WO 2008/077079 | 6/2008 | | |
| WO | WO 2008/083346 | 7/2008 | | |
| WO | WO 2010/037062 | 4/2010 | | |

(Continued)

OTHER PUBLICATIONS

Murphy et al., Proc. Amer. Assoc. Cancer Res., 2005, 46, abstract No. 1495.*
U.S. Appl. No. 14/432,065 Restriction Requirement Mailed Nov. 6, 2015.
U.S. Appl. No. 14/432,065, Travis Young.
Axup, J. et al., Synthesis of site-specific antibody-drug conjugates using unnatural amino acids. PNAS. 2012, pp. 16101-16106, vol. 109, No. 40.
Baeuerle, P.A., P. Kufer, and R. Bargou, BiTE: Teaching antibodies to engage T-cells for cancer therapy. Curr Opin Mol Ther, 2009. pp. 22-30, vol. 11, Issue No. 1.
Beers, S.A., et al., Antigenic modulation limits the efficacy of anti-CD20 antibodies: implications for antibody selection. Blood, Jun. 24, 2010. pp. 5191-5201, vol. 115, Issue No. 25.
Bibl, M., et al., Stability of amyloid-beta peptides in plasma and serum. Electrophoresis, 2012. pp. 445-450, vol. 33, Issue No. 3.

(Continued)

*Primary Examiner* — Hong Sang

(57) ABSTRACT

Disclosed herein are chimeric antigen receptor effector cells (CAR-ECs) and CAR-EC switches. The switchable CAR-ECs are generally T cells. The one or more chimeric antigen receptors may recognize a peptidic antigen on the CAR-EC switch. The CAR-ECs and switches may be used for the treatment of a condition in a subject in need thereof.

25 Claims, 8 Drawing Sheets

(56) References Cited

FOREIGN PATENT DOCUMENTS

| WO | WO 2011/028195 | | 3/2011 | |
|---|---|---|---|---|
| WO | WO 2012/031744 | | 3/2012 | |
| WO | WO 2012/079000 | | 6/2012 | |
| WO | WO 2012/082841 | | 6/2012 | |
| WO | WO 2012082841 | A2 * | 6/2012 | ......... C07K 16/2863 |
| WO | WO 2012/166559 | | 12/2012 | |
| WO | WO 2012/166560 | | 12/2012 | |
| WO | WO 2013/019615 | | 2/2013 | |
| WO | WO 2013/044225 | | 3/2013 | |
| WO | WO 2013/093809 | | 6/2013 | |
| WO | WO 2013/123061 | | 8/2013 | |
| WO | WO 2014/100615 | | 6/2014 | |
| WO | WO 2014/153002 | | 9/2014 | |
| WO | WO 2014/153164 | | 9/2014 | |

OTHER PUBLICATIONS

Bluemel, C., et al., Epitope distance to the target cell membrane and antigen size determine the potency of T cell-mediated lysis by BiTE antibodies specific for a large melanoma surface antigen. Cancer Immunol Immunother, 2010. pp. 1197-1209, vol. 59, Issue No. 8.

Boder, E.T., K.S. Midelfort, and K.D. Wittrup, Directed evolution of antibody fragments with monovalent femtomolar antigen-binding affinity. Proc Natl Acad Sci U S A, 2000, pp. 10701-10705, vol. 97, No. 20.

Bonini, C., et al., The suicide gene therapy challenge: how to improve a successful gene therapy approach. Mol Ther, 2007. pp. 1248-1252, vol. 15, No. 7.

Boulassel, M.R. and A. Galal, Immunotherapy for B-Cell Neoplasms using T Cells expressing Chimeric Antigen Receptors: From antigen choice to clinical implementation. Sultan Qaboos Univ Med J, 2012. p. 273-85, vol. 12, No. 3.

Brentjens, R., et al., Treatment of chronic lymphocytic leukemia with genetically targeted autologous T cells: case report of an unforeseen adverse event in a phase I clinical trial. Mol Ther, 2010. pp. 666-668, vol. 18, No. 4.

Bridgeman, J.S., et al., Structural and biophysical determinants of alphabeta T-cell antigen recognition. Immunology, 2011. pp. 9-18, vol. 135, No. 1.

Cairo, M.S., et al., NCI first International Workshop on the biology, prevention, and treatment of relapse after allogeneic hematopoietic stem cell transplantation: report from the committee on the biological considerations of hematological relapse following allogeneic stem cell transplantation unrelated to graft-versus-tumor effects: state of the science. Biol Blood Marrow Transplant, 2010. pp. 709-728, vol. 16, No. 6.

Cameron, B.J., et al., Identification of a Titin-Derived HLA-Al-Presented Peptide as a Cross-Reactive Target for Engineered MAGE A3-Directed T Cells. Sci Transl Med, 2013. pp. 197ra103, vol. 5, No. 197.

Carpenito, C., et al., Control of large, established tumor xenografts with genetically retargeted human T cells containing CD28 and CD137 domains. Proc Natl Acad Sci U S A, 2009. pp. 3360-3365, vol. 106, No. 9.

Carpenter et al., B-cell maturation antigen is a promising target for adoptive T-cell therapy of multiple myeloma, Clinical Cancer Research, 2013, pp. 2048-2060, vol. 19, No. 8, e-pub Jan. 23, 2013.

Chatterjee et al. A Versatile Platform for Single- and Multiple-Unnatural Amino Acid Mutagenesis in *Escherichia coli*. Biochemistry. Mar. 12, 2013. vol. 52, No. 10, e-pub. Dec. 7, 2013.

Chiarella, P., et al., Antigenic features of protein carriers commonly used in immunisation trials. Biotechnol Lett, 2010. pp. 1215-1221, vol. 32, No. 9.

Chlewicki, L.K., et al., High-affinity, peptide-specific T cell receptors can be generated by mutations in CDR1, CDR2 or CDR3. J Mol Biol, 2005. pp. 223-239, vol. 346, vol. 1.

Chung, E.Y., et al., CD19 is a major B cell receptor-independent activator of MYC-driven B-lymphomagenesis. J Clin Invest, 2012. pp. 2257-2266, vol. 122, No. 6.

Cole, D.K., et al., The molecular determinants of CD8 co-receptor function. Immunology, Oct. 2012. pp. 139-148, vol. 137, No. 2.

Cui et al. Chemically programmed bispecific antibodies that recruit and activate T cells. Journal of Biological Chemistry, 2012, pp. 28206-28214, vol. 287, No. 34.

Davila, M.L., et al., CD19 CAR-targeted T cells induce long-term remission and B Cell Aplasia in an immunocompetent mouse model of B cell acute lymphoblastic leukemia. PLoS One, 2013. p. e61338, vol. 8 No. 4.

Davis, T.A., et al., Therapy of B-cell lymphoma with anti-CD20 antibodies can result in the loss of CD20 antigen expression. Clin Cancer Res, 1999. pp. 611-615, vol. 5, No. 3.

Dubrovska, A., et al., A chemically induced vaccine strategy for prostate cancer. ACS Chem Biol, 2011. pp. 1223-1231, vol. 6, No. 11.

Gavrilyuk, et al. β-Lactam-based Approach for the Chemical Programming of Aldolase Antibody 38C2. Bioorg Med Chem Lett. Mar. 1, 2009, pp. 1421-1424, vol. 19, No. 5, e-pub Jan. 15, 2009.

GenBank Accession No. AB064051: *Homo sapiens* IGK mRNA for immunoglobulin kappa light chain VLJ region, partial cds, clone: K10. Jul. 2, 2002.

Gilham et al., CAR-T cells and solid tumors: tuning T cells to challenge an inveterate foe, Trends in Molecular Medicine, 2012, pp. 377-384, vol. 18, No. 7.

Grada et al., TanCAR: a novel bispecific chimeric antigen receptor for cancer immunotherapy, Molecular Therapy-Nucleic Acids, 2013, pp. 1-11, vol. 2, No. 7.

Griffioen, M., et al., Retroviral transfer of human CD20 as a suicide gene for adoptive T-cell therapy. Haematologica, 2009. pp. 1316-1320, vol. 94, No. 9.

Gross, G., T. Waks, and Z. Eshhar, Expression of immunoglobulin-T-cell receptor chimeric molecules as functional receptors with antibody-type specificity. Proc Natl Acad Sci U S A, 1989. 86(24): p. 10024-8.

Grupp, S.A., et al., Chimeric antigen receptor-modified T cells for acute lymphoid leukemia. N Engl J Med, 2013. pp. 1509-1518, vol. 68, No. 16.

Hanes, J., et al., Ribosome display efficiently selects and evolves high-affinity antibodies in vitro from immune libraries. Proc Natl Acad Sci U S A, 1998. pp. 14130-1435, vol. 95, No. 24.

Herron, J.N., et al., High resolution structures of the 4-4-20 Fab-fluorescein complex in two solvent systems: effects of solvent on structure and antigen-binding affinity. Biophys J, 1994. pp. 2167-2183, vol. 67, No. 6.

Heslop, H.E., Safer CARS. Mol Ther, Apr. 2010. pp. 661-662, vol. 18, No. 4.

Hollatz, G., et al., T cells for suicide gene therapy: activation, functionality and clinical relevance. J Immunol Methods, 2008, pp. 69-81, vol. 331(1-2).

Hotfilder, M., et al., Leukemic stem cells in childhood high-risk ALL/t(9;22) and t(4;11) are present in primitive lymphoid-restricted CD34+CD19− cells. Cancer Res, 2005. pp. 1442-1449, vol. 65, No. 4.

Hudecek, M., et al., Receptor affinity and extracellular domain modifications affect tumor recognition by ROR1-specific chimeric antigen receptor T cells. Clin Cancer Res, 2013.pp. 3153-3164, vol. 19, No. 12.

Hutchins et al. Site-Specific Coupling and Sterically Controlled Formation of Multimeric Antibody Fab Fragments with Unnatural Amino Acids. Journal of Molecular Biology. Mar. 2011. pp. 595-603, vol. 406, No. 4.

Hutchins et al., Selective formation of covalent protein heterodimers with an unnatural amino acid. Chemistry & Biology, 2011, pp. 299-303, vol. 18, No. 3.

Johnson et al. RF1 Knockout Allows Ribosomal Incorporation of Unnatural Amino Acids at Multiple Sites. Nat Chem Biol. May 1, 2012. pp. 779-786, vol. 7, No. 11.

Jung, S. and A. Pluckthun. Improving in vivo folding and stability of a single-chain Fv antibody fragment by loop grafting. Protein Engineering, Aug. 1997, pp. 959-966, vol. 10, No. 8.

(56) References Cited

OTHER PUBLICATIONS

Kalos, M., et al., T cells with chimeric antigen receptors have potent antitumor effects and can establish memory in patients with advanced leukemia. Science Translational Medicine, Aug. 10, 2011. p. 95ra73, vol. 3, No. 95.
Kazane et al. Self-assembled antibody multimers through peptide nucleic acid conjugation. Journal Am Chem Soc, 135(1):340-6, 2013.
Kim et al. Synthesis of bispecific antibodies genetically encoded unnatural amino acids. Journal of the American Chemical Society, Jun. 20, 2012, pp. 9918-9921, vol. 134, No. 24, e-pub Jun. 6, 2012.
Kim et al., Protein conjugation with genetically encoded unnatural amino acids. Current Opinion Chemical Biology, Jun. 2013, pp. 412-419, vol. 17, No. 3.
Kochenderfer et al., Construction and pre-clinical evaluation of an anti-CD19 chimeric antigen receptor, Journal of Immunotherapy, 2009, pp. 689-702, vol. 32, No. 7.
Kochenderfer, J.N., et al., Adoptive transfer of syngeneic T cells transduced with a chimeric antigen receptor that recognizes murine CD19 can eradicate lymphoma and normal B cells. Blood, 2010, pp. 3875-3886, vol. 116, No. 19.
Kochenderfer, J.N., et al., B-cell depletion and remissions of malignancy along with cytokine-associated toxicity in a clinical trial of anti-CD19 chimeric-antigenreceptor-transduced T cells. Blood, 2012, pp. 2709-2720, vol. 119, No. 12.
Kudo K., et al, T Lymphocytes expressing a CD16 signaling receptor exert antibody-dependent cancer cell killing. Cancer Research, Jan. 1, 2014, pp. 93-103, vol. 74, No. 1, e-pub Nov. 6, 2013.
Kularatne, S.A., et al., Prostate-specific membrane antigen targeted imaging and therapy of prostate cancer using a PSMA inhibitor as a homing ligand. Molecular Pharmaceutics, May-Jun. 2009, pp. 780-789, vol. 6, No. 3, e-pub Apr. 12, 2009.
Lamers, C.H., et al., Immune responses to transgene and retroviral vector in patients treated with ex vivo-engineered T cells. Blood, Jan. 6, 2011, pp. 72-82, vol. 117, No. 1, e-pub Oct. 1, 2010.
Lang et al., Genetic encoding of bicyclononynes and trans-cyclooctenes for site-specific protein labeling in vitro and in live mammalian cells via rapid fluorgenic Diels-Alder reactions. Journal of the American Chemical Society, 2012, pp. 10317-1320, vol. 134, No. 25.
le Viseur, C., et al., In childhood acute lymphoblastic leukemia, blasts at different stages of immunophenotypic maturation have stem cell properties. Cancer Cell, Jul. 8, 2008. p. 47-58, vol. 14, No. 1.
Lee, J., M. Sadelain, and R. Brentjens. Retroviral transduction of murine primary T lymphocytes. Methods in Molecular Biology, 2009. pp. 83-96, vol. 506.
Lin et al., Transglutaminase-Catalyzed Site-Specific Conjugation of Small-Molecules to Proteins in Vitro and on the Surface of Living Cells. Journal of American Chemical Society, 2006, pp. 4542-4543, vol. 128, No. 14, e-pub Mar. 16, 2006.
Linette, G.P., et al., Cardiovascular toxicity and titin cross-reactivity of affinity-enhanced T cells in myeloma and melanoma. Blood, Aug. 8, 2013. pp. 863-871, vol. 122, No. 6, e-pub Jun. 14, 2013.
Liu et al. Adding new chemistries to the genetic code. Annual Review of Biochemistry, Jul. 2010, pp. 413-444, vol. 79, e-pub Mar. 18, 2010.
Lu, H., et al., Site-Specific Antibody-Polymer Conjugates for siRNA Delivery. Journal of American Chemical Society, 2013. p. 13885-13891, vol. 135, No. 37.
Lu, Y., et al., Strategy to prevent drug-related hypersensitivity in folate-targeted hapten immunotherapy of cancer. AAPS J, 2009. p. 628-638, vol. 11, No. 3.
Ma, Q., R.M. Gonzalo-Daganzo, and R.P. Junghans, Genetically engineered T cells as adoptive immunotherapy of cancer. Cancer Chemother Biol Response Modif, 2002. pp. 315-341, vol. 20.
Ma, Y., et al., Targeting of antigens to B lymphocytes via CD19 as a means for tumor vaccine development. Journal of Immunology, Jun. 1, 2013, pp. 5588-5599, vol. 190, No. 11. e-pub Apr. 29, 2013.
Maher, J., Immunotherapy of malignant disease using chimeric antigen receptor engrafted T cells. International Scholarly Research Notices Oncology, 2012, p. 278093, vol. 2012.
Masir, N., et al., Loss of CD19 expression in B-cell neoplasms. Histopathology, 2006. p. 239-246, vol. 48, No. 3.
Milone, M.C., et al., Chimeric receptors containing CD137 signal transduction domains mediate enhanced survival of T cells and increased antileukemic efficacy in vivo. Molecular Therapy, 2009, pp. 1453-1464, vol. 17, No. 8.
Moore, P.A., et al., Application of dual affinity retargeting molecules to achieve optimal redirected T-cell killing of B-cell lymphoma. Blood, Apr. 28, 2011. pp. 4542-4551, vol. 117, No. 17. e-pub Feb. 7, 2011.
Morgan, R.A., et al., Case report of a serious adverse event following the administration of T cells transduced with a chimeric antigen receptor recognizing ERBB2. Molecular Therapy, Apr. 18, 2010. pp. 843-851 vol. 18, No. 4. e-pub Feb. 23, 2010.
Mossner, E., H. Koch, and A. Pluckthun, Fast selection of antibodies without antigen purification: adaptation of the protein fragment complementation assay to select antigen-antibody pairs. Journal of Molecular Biology, Apr. 27, 2001, pp. 115-122, vol. 308, No. 2.
Nauerth, M., et al., TCR-ligand koff rate correlates with the protective capacity of antigen-specific CD8+ T cells for adoptive transfer. Science Translational Medicine, Jul. 3, 2013, pp. 192ra87, vol. 5, No. 192.
Olejniczak, S.H., et al., A quantitative exploration of surface antigen expression in common B-cell malignancies using flow cytometry. Immunol Invest, 2006. pp. 93-114, vol. 35, No. 1.
PCT/US2014/060684 International Search Report Mailed Jan. 22, 2015.
PCT/US2014/060713 International Search Reported Dated Jan. 15, 2015.
Popkov, et al. Instant immunity through chemically programmable vaccination and covalent self-assembly. Proceedings of the National Academy of Sciences of the United States of America. Early Edition. Jan. 7, 2009, pp. 1-6.
Porter, D.L., et al., Chimeric antigen receptor-modified T cells in chronic lymphoid leukemia. New England Journal of Medicine, Aug. 25, 2011. pp. 725-733, vol. 365, No. 8.
Rader, et al. A Humanized Aldolase Antibody for Selective Chemotherapy and Adaptor Immunotherapy. Journal of Molecular Biology, 2003, pp. 889-899, vol. 332.
Rader, et al. Chemically programmed antibodies. Trends in Biotechnology, Apr. 2014, pp. 186-197, vol. 32, No. 4.
Rader, et al., Chemically programmed monoclanal antibodies for cancer therapy: Adaptor immunotherapy based on a covalent antibody catalyst. PNAS Apr. 29, 2003, pp. 5396-5400, vol. 100, No. 9.
Reichert, Biospecific antibodies: A global overview of development as innovative therapeutics. AAPS 2013 National Biotechnology Conference, May 21, 2013, 14 pages.
Restifo, N.P., M.E. Dudley, and S.A. Rosenberg, Adoptive immunotherapy for cancer: harnessing the T cell response. Nature Reviews Immunology, Apr. 2012, pp. 269-281, vol. 12, No. 4.
Rezvani, A.R. and D.G. Maloney. Rituximab resistance. Best Pract Res Clin Haematol, Jun. 2011. pp. 203-216, vol. 24, No. 2. e-pub Apr. 13, 2011.
Riviere, I., K. Brose, and R.C. Mulligan, Effects of retroviral vector design on expression of human adenosine deaminase in murine bone marrow transplant recipients engrafted with genetically modified cells. Proc Natl Acad Sci USA, Jul. 18, 1995, pp. 6733-6737, vol. 92, No. 15.
Romer, P.S., et al., Preculture of PBMCs at high cell density increases sensitivity of T-cell responses, revealing cytokine release by CD28 superagonist TGN1412. Blood, Dec. 22, 2011. pp. 6772-6782, vol. 118, No. 26.
Scholler, J., et al., Decade-long safety and function of retroviral-modified chimeric antigen receptor T cells. Science Translational Medicine, May 2, 2012, pp. 132ra53, vol. 4, No. 132.
Scott, D., et al., Immunogenicity of biotinylated hapten-avidin complexes. Mol Immunol, Nov. 1984. p. 1055-60, vol. 21, No. 11.
Sigma-Aldrich Co. LLC, Product Information Monoclanal Anti-CD3, clone UCHT-1 produced in mouse, purified immunoglobulin. Catalog No. C7048, © 2012.

(56) References Cited

OTHER PUBLICATIONS

Sinha et al. Preparation of integrin α(v)β(3)-targeting Ab 38C2 constructs. Nature Protocols Mar. 8, 2007, pp. 449-456, vol. 2.
Stone, J.D., et al., A sensitivity scale for targeting T cells with chimeric antigen receptors (CARs) and bispecific T-cell Engagers (BiTEs). Oncoimmunology, Sep. 1, 2012. pp. 863-873, vol. 1, No. 6.
Straathof, K.C., et al., An inducible caspase 9 safety switch for T-cell therapy. Blood, Jun. 1, 2005. pp. 4247-4254, vol. 105, No. 11, e-pub Feb. 22, 2005.
Suhoski, M.M., et al., Engineering artificial antigen-presenting cells to express a diverse array of co-stimulatory molecules. Molecular Therapy, May 2007. pp. 981-988, vol. 15, No. 5, e-pub Mar. 20, 2007.
Tai, W. et al., Development of a Peptide-Drug Conjugate for Prostate Cancer Therapy. Molecular Pharmaceutics. 2011, pp. 901-912, vol. 8.
Tamada et al., Redirecting gene-modified T cells toward various cancer types using tagged antibodies, Clinical Cancer Research, Dec. 1, 2012, pp. 6436-6445, vol. 18, No. 23, e-pub Oct. 2, 2012.
Terakura, S., et al., Generation of CD19-chimeric antigen receptor modified CD8+ T cells derived from virus-specific central memory T cells. Blood, Jan. 5, 2012. pp. 72-82, vol. 119, No. 1, e-pub Oct. 26, 2011.
Themeli, M., et al., Generation of tumor-targeted human T lymphocytes from induced pluripotent stem cells for cancer therapy. Nature Biotechnology, 2013, pp. 928-933, vol. 31, e-pub Aug. 11, 2013.
Thomas et al., Application of strain-promoted azide-alkyne cycloaddition and tetrazine ligation to targeted Fc-drug conjugates. Bioconjugate Chemistry, 2012, pp. 2007-2013, vol. 23, No. 10.
Traversari, C., et al., The potential immunogenicity of the TK suicide gene does not prevent full clinical benefit associated with the use of TK-transduced donor lymphocytes in HSCT for hematologic malignancies. Blood, Jun. 1, 2007. pp. 4708-4715, vol. 109, No. 11, e-pub Feb. 27, 2007.
Turatti, F., et al., Redirected activity of human antitumor chimeric immune receptors is governed by antigen and receptor expression levels and affinity of interaction. Journal of Immunotherapy, Oct. 2007, pp. 684-693, vol. 30, No. 7.
Urbanska K, et al, Targeted cancer immunotherapy via combination of designer bispecific antibody and novel gene-engineered T cells. Journal of Translational Medicine, Dec. 2014, 347-359, vol. 12.
Urbanska, K. and D.J. Powell, Development of a novel universal immune receptor for antigen targeting: To Infinity and beyond. Oncoimmunology, Aug. 1, 2012. pp. 777-779, vol. 1, No. 5.
Urbanska, K., et al., A universal strategy for adoptive immunotherapy of cancer through use of a novel T-cell antigen receptor. Cancer Research, Apr. 1, 2012. pp. 1844-1852, vol. 72, No. 7, e-pub Feb. 7, 2012.
Uttenthal, B.J., et al., Challenges in T cell receptor gene therapy. Journal of Gene Med, Jun. 2012. pp. 386-399, vol. 14, No. 6.
van Dam, G.M., et al., Intraoperative tumor-specific fluorescence imaging in ovarian cancer by folate receptor-alpha targeting: first in-human results. Nature Medicine, 2011. pp. 1315-1319, vol. 17, No. 10, e-pub Sep. 18, 2011.
Vaughan, T.J., et al., Human antibodies with sub-nanomolar affinities isolated from a large non-immunized phage display library. Nat Biotechnol, Mar. 1996. pp. 309-314, vol. 14, No. 3.
Wang et al. Expanding the genetic code. Angew Chem Int Ed, 2005, pp. 34-66, vol. 44, No. 1, e-pub Dec. 17, 2004.
Xu, X.J., H.Z. Zhao, and Y.M. Tang, Efficacy and safety of adoptive immunotherapy using anti-CD19 chimeric antigen receptor transduced T-cells: a systematic review of phase I clinical trials. Leuk Lymphoma, Feb. 2013. pp. 255-260, vol. 54, No. 2.
Young, T.S. and P.G. Schultz, Beyond the canonical 20 amino acids: expanding the genetic lexicon. Journal of Biological Chemistry, Apr. 9, 2010. pp. 11039-11044, vol. 285, No. 15.
Young, T.S., et al., An enhanced system for unnatural amino acid mutagenesis in E. coli. Journal Molecular Biology, Jan. 15, 2010. pp. 361-374, vol. 395, No. 2, e-pub Oct. 21, 2009.
Yu, D. and A. Thomas-Tikhonenko, A non-transgenic mouse model for B-cell lymphoma: in vivo infection of p53-null bone marrow progenitors by a Myc retrovirus is sufficient for tumorigenesis. Oncogene, Mar. 14, 2002. pp. 1922-1927, vol. 21, No. 12.
Yu, D., et al., Oscillation between B-lymphoid and myeloid lineages in Myc-induced hematopoietic tumors following spontaneous silencing/reactivation of the EBF/Pax5 pathway. Blood, Mar. 1, 2003. pp. 1950-1955, vol. 101, No. 5, e-pub Oct. 24, 2002.
Zahnd, C., et al., Directed in vitro evolution and crystallographic analysis of a peptide-binding single chain antibody fragment (scFv) with low picomolar affinity. Journal of Biological Chemistry, Apr. 30, 2004. pp. 18870-18877, vol. 279, No. 18.
Zhang, M.Y., et al., Identification and characterization of a new cross-reactive human immunodeficiency virus type 1-neutralizing human monoclonal antibody. Journal of Virology, Sep. 2004. pp. 9233-9242, vol. 78, No. 17.
Zhang, M.Y., et al., Identification of a novel CD4i human monoclonal antibody Fab that neutralizes HIV-1 primary isolates from different clades. Antiviral Research, Mar. 2004. pp. 161-164, vol. 61, No. 3.
Ang et al., "Generating a Chimeric Antigen Receptor to Redirect T-cell Specificity after Infusion" *Molecular Therapy* 19( Suppl 1): No. 353, p. S137, May 2011.
Arcondéguy et al., "Survey and Summary. VEGF-A mRNA processing, stability and translation: a paradigm for intricate regulation of gene expression at the post-transcriptional level," *Nucleic Acids Research* 41(17): 7997-8010, 2013.
Brentjens et al., "Eradication of systemic B-cell tumors by genetically targeted human T lymphocytes co-stimulated by CD80 and interleukin-15," *Nature Medicine* 9(3): 279-286, Mar. 2003.
Brentjens et al., "Genetically Targeted T Cells Eradicate Systemic Acute Lymphoblastic Leukemia Xenografts," *Clinical Cancer Research* 13(18): 5426-5435, Sep. 15, 2007.
Davis et al., "Therapy of B-Cell Lymphoma with Anti-CD20 Antibodies Can Result in the Loss of CD20 Antigen Expression," *Clinical Cancer Research* 5: 611-615, Mar. 1999.
Dengl et al., "Engineered hapten-binding antibody derivatives for modulation of pharmacokinetic properties of small molecules and targeted payload delivery," *Immunological Reviews* 270: 165-177, 2016.
Ertl et al., "Considerations for the Clinical Application of Chimeric Antigen Receptor T Cells: Observations from a Recombinant DNA Advisory Committee Symposium Held Jun. 15, 2010," *Cancer Research* 71(9): 3175-3181, 2011.
Eshhar et al., "Chimeric T cell receptor which incorporates the anti-tumour specificity of a monoclonal antibody with the cytolytic activity of T cells: a model system for immunotherapeutical approach" *Br. J. Cancer* 62: 27-29, 1990.
Eshhar et al., Specific activation and targeting of cytotoxic lymphocytes through chimeric single chains consisting of antibody-binding domains and the y or subunits of the immunoglobulin and T-cell receptors, Proc. Natl. Acad. Sci. USA 90: 720-724, Jan. 1993.
Eshhar, "The T-Body Approach: Redirecting T Cells with Antibody Specificity," Y. Chernajovsky, A. Nissim (eds.), Therapeutic Antibodies. Handbook of Experimental Pharmacology 181. Springer-Verlag Berlin Heidelberg 2008, pp. 329-342.
Fernando et al., "Targeted Therapy of Colorectal Cancer: Clinical Experience with Bevacizumab," *The Oncologist* 9(suppl 1): 11-18, 2004.
Fitzer-Attas et al., "Harnessing Syk Family Tyrosine Kinases as Signaling Domains for Chimeric Single Chain of the Variable Domain Receptors: Optimal Design for T Cell Activation," The Journal of Immunology 160: 145-154, 1998.
Friedmann-Morvinski et al., "Redirected primary T cells harboring a chimeric receptor require costimulation for their antigen-specific activation," Blood 105: 3087-3093, 2005.
Frost et al., "In Vitro Evaluation of Avidin Antibody Pretargeting Using 211At-Labeled and Biotinylated Poly-L-Lysine as Effector Molecule," Cancer 116(4 suppl): 1101-1110, 2010.

(56) References Cited

OTHER PUBLICATIONS

Gamzatova et al., "Human leucocyte antigen (HLA) A2 as a negative clinical prognostic factor in patients with advanced ovarian cancer," Gynecologic Oncology 103: 145-150, 2006.

Gillies et al., "Targeting Human Cytotoxic T Lymphocytes to Kill Heterologous Epidermal Growth Factor Receptor-Bearing Tumor Cells. Tumor-Infiltrating Lymphocyte/Hormone Receptor/Recombinant Antibody," J. Immu. 146(3): 1067-1071, Feb. 1, 1991.

Gross and Eshhar, "Endowing T cells with antibody specificity using chimeric T cell receptors," FASEB J. 6: 3370-3378, 1992.

Gross et al., "Expression of immunoglobulin-T-cell receptor chimeric molecules as functional receptors with antibody-type specificity," Proc. Natl. Acad. Sci. USA 86: 10024-10028, Dec. 1989.

Guest et al., "The Role of Extracellular Spacer Regions in the Optimal Design of Chimeric Immune Receptors. Evaluation of Four Different scFvs and Antigens," J. Immunother 28(3): 203-211, May/Jun. 2005.

Hombach et al., "T cell activation by recombinant FceRl γ-chain immune receptors: an extracellular spacer domain impairs antigen-dependent T cell activation but not antigen recognition," Gene Therapy 7: 1067-1075, 2000.

Hwu et al., "Lysis of Ovarian Cancer Cells by Human Lymphocytes Redirected with a Chimeric Gene Composed of an Antibody Variable Region and the Fc Receptor γ Chain," J. Exp. Med. 178: 361-366, Jul. 1993.

Johnson et al., "Gene therapy with human and mouse T-cell receptors mediates cancer regression and targets normal tissues expressing cognate antigen," Blood 114: 535-546, 2009.

Kershaw et al., "Gene-Engineered T Cells as a Superior Adjuvant Therapy for Metastatic Cancer," The Journal of Immunology 173(3): 2143-2150, Aug. 1, 2004.

Kershaw et al., "A Phase I Study on Adoptive Immunotherapy Using Gene-Modified T Cells for Ovarian Cancer," Clinical Cancer Research 12(20 Pt 1): 6106-6115, Oct. 15, 2006.

Krause et al., "Antigen-dependent CD28 Signaling Selectively Enhances Survival and Proliferation in Genetically Modified Activated Human Primary T Lymphocytes," J. Exp. Med. 188(4): 619-626, Aug. 17, 1998.

Kranz et al., "Conjugates of folate and anti-T-cell-receptor antibodies specifically target folate-receptor-positive tumor cells for lysis," Proc. Natl. Acad. Sci. USA 92: 9057-9061, Sep. 1995.

Kuroki et al., "Strategies to Endow Cytotoxic T Lymphocytes or Natural Killer Cells with Antibody Activity against Carcinoembryonic Antigen," Tumor Biol. 25: 208-216, 2004.

Lamers et al., "Treatment of Metastatic Renal Cell Carcinoma With Autologous T-Lymphocytes Genetically Retargeted Against Carbonic Anhydrase IX: First Clinical Experience," Journal of Clinical Oncology 24(13): e20-e22, May 1, 2006.

Lobbestael et al., "Immunohistochemical detection of transgene expression in the brain using small epitope tags," BMC Biotechnology 10, six pages, 2010.

Ma et al., "Carcinoembryonic antigen-immunoglobulin Fc fusion protein (CEA-Fc) for identification and activation of anti-CEA immunoglobulin-T-cell receptor-modified T cells, representative of a new class of Ig fusion proteins," C. Gene Therapy 11: 297-306, 2004.

Maher et al., "Human T-lymphocyte cytotoxicity and proliferation directed by a single chimeric TCRζ/CD28 receptor," Nature Biotechnology 20: 70-75, Jan. 2002.

Ogg et al., "Sensitization of tumour cells to lysis by virus-specific CTL using antibody-targeted MHC class I/peptide complexes," British Journal of Cancer 82(5): 1058-1062, 2000.

Oshimi et al., Increased Lysis of Patient CD10-Positive Leukemic Cells by T Cells Coated With Anti-CD3 Fab' Antibody Cross-Linked to Anti-CD10 Fab' Antibody, Blood 77(5): 1044-1049, Mar. 1, 1991.

Park et al., "Adoptive Transfer of Chimeric Antigen Receptor Re-directed Cytolytic T Lymphocyte Clones in Patients with Neuroblastoma," Molecular Therapy 15(4): 825-833, Apr. 2007.

Perez et al., "Specific targeting of cytotoxic T cells by anti-T3 linked to anti-target cell antibody," Nature 316: 354-356, Jul. 25, 1985.

Pule et al., "Virus-specific T cells engineered to coexpress tumor-specific receptors: persistence and antitumor activity in individuals with neuroblastoma," Nature Medicine 14(11): 1264-1270, Nov. 2008.

Reid et al., "Extrinsic Cotton Effects in Hapten-Carrier and Hapten-Antibody Interactions," Proc. Nat. Acad. Sci. USA 68(6): 1184-1187, Jun. 1971.

Riddell and Protzer, "Carving the CAR," Gene Therapy 17: 1191-1192, 2010.

Sadelain et al., "The promise and potential pitfalls of chimeric antigen receptors," Current Opinion in Immunology 21: 215-223, 2009.

Savage et al., "Induction of viral and tumor specific CTL responses using antibody targeted HLA class I peptide complexes," British Journal of Cancer 86: 1336-1342, 2002.

Shirasu et al., "Construction and Molecular Characterization of Human Chimeric T-Cell Antigen Receptors Specific for Carcinoembryonic Antigen," Anticancer Research 30: 2731-2738, 2010.

Siliciano et al., "The Interaction of Nominal Antigen With T Cell Antigen Receptors. I. Specific Binding of Multivalent Nominal Antigen to Cytolytic T Cell Clone," The Journal of Immunology 135(2): 906-914, Aug. 1985.

Schmitt-Verhulst et al., "H-2-Restricted Cytotoxic Effectors Generated In Vitro by the Addition of Trinitrophenyl-Conjugated Soluble Proteins," The Journal of Experimental Medicine 147: 352-368, 1978.

Till et al., "Adoptive immunotherapy for indolent non-Hodgkin lymphoma and mantle cell lymphoma using genetically modified autologous CD20-specific T cells," Blood 112(6): 2261-2271, Sep. 15, 2008.

Weiden and Breitz, "Pretargeted radioimmunotherapy (PRIT™) for treatment of non-Hodgkin's lymphoma (NHL)," Critical Reviews in Oncology/Hematology 40: 37-51, 2001.

Zeidler et al., "Simultaneous Activation of T Cells and Accessory Cells by a New Class of Intact Bispecific Antibody Results in Efficient Tumor Cell Killing," The Journal of Immunology 163: 1246-1252, 1999.

Xiang et al., "Production of hybrid bispecific antibody recognizing human colorectal carcinoma and CD3 antigen," Mol. Biother. 4: 15-23, Mar. 1992.

\* cited by examiner

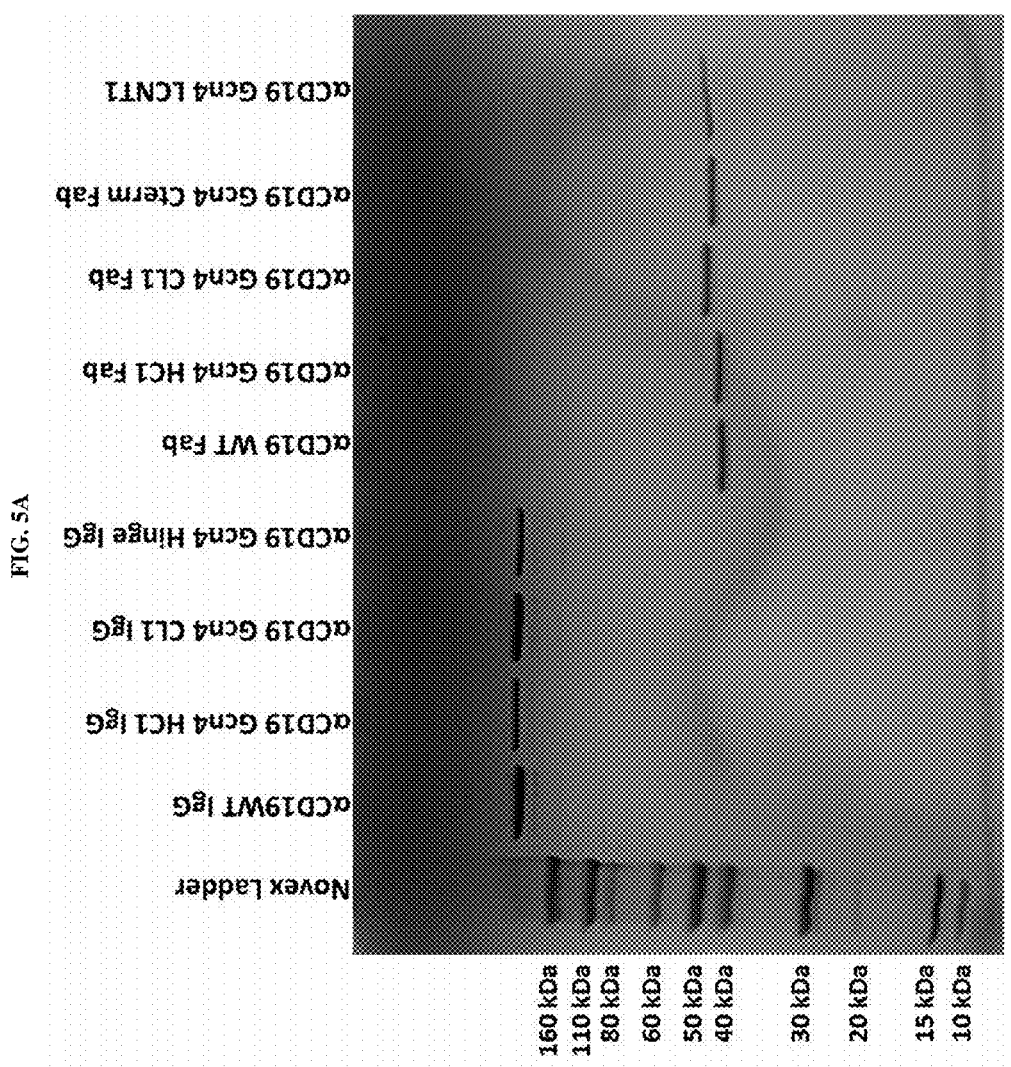

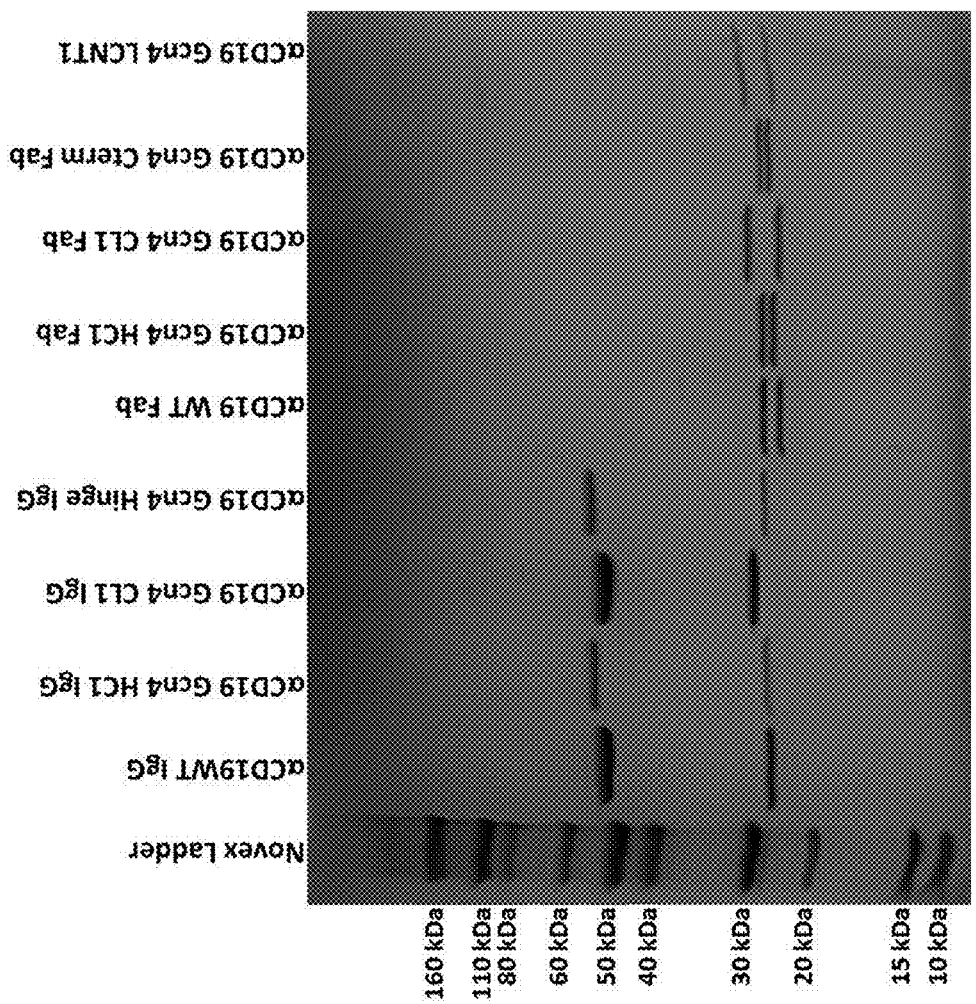

SEQUENCE LISTING

<160> NUMBER OF SEQ ID NOS: 49

<210> SEQ ID NO 1
<211> LENGTH: 8835
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
caggtggcac ttttcgggga aatgtgcgcg gaacccctat ttgtttattt ttctaaatac      60
attcaaatat gtatccgctc atgagacaat aaccctgata aatgcttcaa taatattgaa     120
aaaggaagag tatgagtatt caacatttcc gtgtcgccct tattcccttt tttgcggcat     180
tttgccttcc tgttttttgct cacccagaaa cgctggtgaa agtaaaagat gctgaagatc     240
agttgggtgc acgagtgggt tacatcgaac tggatctcaa cagcggtaag atccttgaga     300
gttttcgccc cgaagaacgt tttccaatga tgagcacttt taaagttctg ctatgtggcg     360
cggtattatc ccgtattgac gccgggcaag agcaactcgg tcgccgcata cactattctc     420
agaatgactt ggttgagtac tcaccagtca cagaaaagca tcttacggat ggcatgacag     480
taagagaatt atgcagtgct gccataacca tgagtgataa cactgcggcc aacttacttc     540
tgacaacgat cggaggaccg aaggagctaa ccgcttttt gcacaacatg ggggatcatg     600
taactcgcct tgatcgttgg gaaccggagc tgaatgaagc cataccaaac gacgagcgtg     660
acaccacgat gcctgtagca atggcaacaa cgttgcgcaa actattaact ggcgaactac     720
ttactctagc ttcccggcaa caattaatag actggatgga ggcggataaa gttgcaggac     780
cacttctgcg ctcggccctt ccggctggct ggtttattgc tgataaatct ggagccggtg     840
agcgtgggtc tcgcggtatc attgcagcac tggggccaga tggtaagccc tcccgtatcg     900
tagttatcta cacgacgggg agtcaggcaa ctatggatga acgaaataga cagatcgctg     960
agataggtgc ctcactgatt aagcattggt aactgtcaga ccaagtttac tcatatatac    1020
tttagattga tttaaaactt catttttaat ttaaaaggat ctaggtgaag atccttttttg    1080 ataatctcat gaccaaaatc ccttaacgtg agttttcgtt ccactgagcg tcagaccccg    1140
tagaaaagat caaaggatct tcttgagatc ctttttttct gcgcgtaatc tgctgcttgc    1200
aaacaaaaaa accaccgcta ccagcggtgg tttgtttgcc ggatcaagag ctaccaactc    1260
tttttccgaa ggtaactggc ttcagcagag cgcagatacc aaatactgtc cttctagtgt    1320
agccgtagtt aggccaccac ttcaagaact ctgtagcacc gcctacatac ctcgctctgc    1380
taatcctgtt accagtggct gctgccagtg gcgataagtc gtgtcttacc gggttggact    1440
caagacgata gttaccggat aaggcgcagc ggtcgggctg aacggggggt tcgtgcacac    1500
agcccagctt ggagcgaacg acctacaccg aactgagata cctacagcgt gagctatgag    1560
```

```
aaagcgccac gcttcccgaa gggagaaagg cggacaggta tccggtaagc ggcagggtcg    1620
gaacaggaga gcgcacgagg gagcttccag ggggaaacgc ctggtatctt tatagtcctg    1680
tcgggtttcg ccacctctga cttgagcgtc gattttgtg atgctcgtca gggggggcgga    1740 gcctatggaa aaacgccagc aacgcggcct ttttacggtt cctggccttt tgctggcctt    1800
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga agagcgccca atacgcaaac cgcctctccc gcgcgttgg ccgattcatt     1980 aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttaat    2220
gtagtcttat gcaatactct tgtagtcttg caacatggta acgatgagtt agcaacatgc    2280
cttacaagga gagaaaaagc accgtgcatg ccgattggtg gaagtaaggt ggtacgatcg    2340
tgccttatta ggaaggcaac agacgggtct gacatggatt ggacgaacca ctgaattgcc    2400
gcattgcaga gatattgtat ttaagtgcct agctcgatac aataaacggg tctctctggt    2460
tagaccagat ctgagcctgg gagctctctg gctaactagg gaacccactg cttaagcctc    2520
aataaagctt gccttgagtg cttcaagtag tgtgtgcccg tctgttgtgt gactctggta    2580
actagagatc cctcagaccc ttttagtcag tgtggaaaat ctctagcagt ggcgcccgaa    2640
cagggacctg aaagcgaaag ggaaaccaga gctctctcga cgcaggactc ggcttgctga    2700
agcgcgcacg gcaagaggcg aggggcggcg actggtgagt acgccaaaaa ttttgactag    2760
cggaggctag aaggagagag atgggtgcga gagcgtcagt attaagcggg ggagaattag    2820
atcgcgatgg gaaaaaattc ggttaaggcc aggggaaag aaaaaatata aattaaaaca     2880
tatagtatgg gcaagcaggg agctagaacg attcgcagtt aatcctggcc tgttagaaac    2940
atcagaaggc tgtagacaaa tactgggaca gctacaacca tcccttcaga caggatcaga    3000
agaacttaga tcattatata atacagtagc aaccctctat tgtgtgcatc aaaggataga    3060
gataaaagac accaaggaag cttagacaa gatagaggaa gagcaaaaca aaagtaagac     3120
caccgcacag caagcggccg ctgatcttca gacctggagg aggagatatg agggacaatt    3180
ggagaagtga attatataaa tataaagtag taaaaattga accattagga gtagcaccca    3240
ccaaggcaaa gaagaagtg gtgcagagag aaaaaagagc agtgggaata ggagctttgt     3300
tccttgggtt cttgggagca gcaggaagca ctatgggcgc agcctcaatg acgctgacgg    3360
tacaggccag acaattattg tctggtatag tgcagcagca gaacaatttg ctgagggcta    3420
ttgaggcgca acagcatctg ttgcaactca cagtctgggg catcaagcag ctccaggcaa    3480
gaatcctggc tgtggaaaga tacctaaagg atcaacagct cctggggatt tggggttgct    3540
ctggaaaact catttgcacc actgctgtgc cttggaatgc tagttggagt aataaatctc    3600
tggaacagat tggaatcaca cgacctggat ggagtgggac agagaaatta caattacac     3660 aagcttaata cactccttaa ttgaagaatc gcaaaaccag caagaaaaga atgaacaaga    3720
attattggaa ttagataaat gggcaagttt gtggaattgg tttaacataa caaattggct    3780
gtggtatata aaattattca taatgatagt aggaggcttg gtaggtttaa gaatagtttt    3840
tgctgtactt tctatagtga atagagttag gcagggatat tcaccattat cgtttcagac    3900
ccacctccca accccgaggg gacccgacag gcccgaagga atagaagaag aaggtggaga    3960
```

| | |
|---|---|
| gagagacaga gacagatcca ttcgattagt gaacggatct cgacggttaa cttttaaaag | 4020 |
| aaaaggggg attgggggt acagtgcagg ggaaagaata gtagacataa tagcaacaga | 4080 |
| catacaaact aaagaattac aaaaacaaat tacaaaaatt caaaatttta tcgagctttg | 4140 |
| caaagatgga taaagtttta aacagagagg aatctttgca gctaatggac cttctaggtc | 4200 |
| ttgaaaggag tgcctcgtga ggctccggtg cccgtcagtg ggcagagcgc acatcgccca | 4260 |
| cagtccccga gaagttgggg ggaggggtcg gcaattgaac cggtgcctag agaaggtggc | 4320 |
| gcggggtaaa ctgggaaagt gatgtcgtgt actggctccg ccttttttccc gagggtgggg | 4380 |
| gagaaccgta tataagtgca gtagtcgccg tgaacgttct ttttcgcaac gggtttgccg | 4440 |
| ccagaacaca ggtaagtgcc gtgtgtggtt cccgcgggcc tggcctcttt acgggttatg | 4500 |
| gcccttgcgt gccttgaatt acttccacct ggctgcagta cgtgattctt gatcccgagc | 4560 |
| ttcgggttgg aagtgggtgg gagagttcga ggccttgcgc ttaaggagcc ccttcgcctc | 4620 |
| gtgcttgagt tgaggcctgg cctgggcgct ggggccgccg cgtgcgaatc tggtggcacc | 4680 |
| ttcgcgcctg tctcgctgct ttcgataagt ctctagccat ttaaaatttt tgatgacctg | 4740 |
| ctgcgacgct ttttttctgg caagatagtc ttgtaaatgc gggccaagat ctgcacactg | 4800 |
| gtatttcggt ttttggggcc gcgggcggcg acggggcccg tgcgtcccag cgcacatgtt | 4860 |
| cggcgaggcg gggcctgcga gcgcggccac cgagaatcgg acggggtag tctcaagctg | 4920 |
| gccggcctgc tctggtgcct ggcctcgcgc cgccgtgtat cgccccgccc tgggcggcaa | 4980 |
| ggctggcccg gtcggcacca gttgcgtgag cggaaagatg gccgcttccc ggccctgctg | 5040 |
| cagggagctc aaaatggagg acgcggcgct cgggagagcg ggcgggtgag tcacccacac | 5100 |
| aaaggaaaag ggcctttccg tcctcagccg tcgcttcatg tgactccacg gagtaccggg | 5160 |
| cgccgtccag gcacctcgat tagttctcga gcttttggag tacgtcgtct ttaggttggg | 5220 |
| gggaggggtt ttatgcgatg gagtttcccc acactgagtg ggtggagact gaagttaggc | 5280 |
| cagcttggca cttgatgtaa ttctccttgg aatttgccct ttttgagttt ggatcttggt | 5340 |
| tcattctcaa gcctcagaca gtggttcaaa gtttttttct tccatttcag gtgtcgtgag | 5400 |
| gaattcggta ccgcggccgc ccggggatcc atggccttac cagtgaccgc cttgctcctg | 5460 |
| ccgctggcct tgctgctcca cgccgccagg ccggacgccg ttgtgaccca ggaatccgct | 5520 |
| ctgaccttct ctccaggcga aaccgtgact ctgacttgcc gtagtagcac cggggctgtg | 5580 |
| accacatcta actatgccag ttgggtccag gaaaaaccgg atcacctgtt tactggcctg | 5640 |
| attggcggca ccaacaatcg cgcaccgggt gtgcccgctc gtttcagcgg ttccctgatt | 5700 |
| ggggacaagg cagcactgac tatcaccggc gcccagaccg aagatgaggc gatctatttt | 5760 |
| tgcgtcctgt ggtacagcga ccattgggtg ttcgggggag gcaccaaaact gacagtgctg | 5820 |
| ggcggaggag gaggttcagg aggaggaggt agcgggggag gcggttccgg gggaggcggt | 5880 |
| tctgatgtgc agctgcaaga atccgggcca ggactggttg cgccttctca gagtctgtca | 5940 |
| attacatgta ctgttagtgg cttttctgctg accgactatg gtgtgaactg ggttcgtcag | 6000 |
| agcccaggca agggtctgga gtggctggga gtgatttggg gggatggaat cacagactac | 6060 |
| aatagcgcac tgaaatctcg gctgagtgtt accaaagata cagcaagtc ccaggtcttc | 6120 |
| ctgaagatga acagcctgca aagcggcgac tccgctcgct attactgcgt taccggactg | 6180 |
| tttgattatt gggggcaggg gacaactctg actgtttcct ccaccacgac gccagcgccg | 6240 |
| cgaccaccaa caccggcgcc caccatcgcg tcgcagcccc tgtccctgcg cccagaggcg | 6300 |

```
tgccggccag cggcgggggg cgcagtgcac acgaggggc tggacttcgc ctgtgatatc    6360
tacatctggg cgcccttggc cgggacttgt ggggtccttc tcctgtcact ggttatcacc    6420
ctttactgca aacggggcag aaagaaactc ctgtatatat tcaaacaacc atttatgaga    6480
ccagtacaaa ctactcaaga ggaagatggc tgtagctgcc gatttccaga agaagaagaa    6540
ggaggatgtg aactgagagt gaagttcagc aggagcgcag acgccccgc gtacaagcag    6600
ggccagaacc agctctataa cgagctcaat ctaggacgaa gagaggagta cgatgttttg    6660
gacaagagac gtggccggga ccctgagatg gggggaaagc cgagaaggaa gaaccctcag    6720
gaaggcctgt acaatgaact gcagaaagat aagatggcgg aggcctacag tgagattggg    6780
atgaaaggcg agcgccggag gggcaagggg cacgatggcc tttaccaggg tctcagtaca    6840
gccaccaagg acacctacga cgcccttcac atgcaggccc tgcccctcg ctaagtcgac    6900
aatcaacctc tggattacaa aatttgtgaa agattgactg gtattcttaa ctatgttgct    6960
ccttttacgc tatgtggata cgctgcttta atgcctttgt atcatgctat tgcttcccgt    7020
atggctttca ttttctcctc cttgtataaa tcctggttgc tgtctcttta tgaggagttg    7080
tggcccgttg tcaggcaacg tggcgtggtg tgcactgtgt ttgctgacgc aaccccact    7140
ggttgggca ttgccaccac ctgtcagctc ctttccggga ctttcgcttt cccctccct    7200
attgccacgg cggaactcat cgccgcctgc cttgcccgct gctggacagg ggctcggctg    7260
ttgggcactg acaattccgt ggtgttgtcg gggaagctga cgtcctttcc atggctgctc    7320
gcctgtgttg ccacctggat tctgcgcggg acgtccttct gctacgtccc ttcggccctc    7380
aatccagcgg accttccttc ccgcggcctg ctgccggctc tgcggcctct tccgcgtctt    7440
cgccttcgcc ctcagacgag tcggatctcc ctttgggccg cctccccgcc tggaattcga    7500
gctcggtacc tttaagacca atgacttaca aggcagctgt agatcttagc cacttttaa    7560
aagaaaaggg gggactggaa gggctaattc actcccaacg aagacaagat ctgcttttg    7620
cttgtactgg gtctctctgg ttagaccaga tctgagcctg ggagctctct ggctaactag    7680
ggaacccact gcttaagcct caataaagct tgccttgagt gcttcaagta gtgtgtgccc    7740
gtctgttgtg tgactctggt aactagagat ccctcagacc cttttagtca gtgtggaaaa    7800
tctctagcag tagtagttca tgtcatctta ttattcagta tttataactt gcaaagaaat    7860
gaatatcaga gagtgagagg aacttgttta ttgcagctta taatggttac aaataaagca    7920
atagcatcac aaatttcaca aataaagcat ttttttcact gcattctagt tgtggtttgt    7980
ccaaactcat caatgtatct tatcatgtct ggctctagct atcccgcccc taactccgcc    8040
cagttccgcc cattctccgc cccatggctg actaatttt tttatttatg cagaggccga    8100
ggccgcctcg gcctctgagc tattccagaa gtagtgagga ggcttttttg gaggcctagg    8160
cttttgcgtc gagacgtacc caattcgccc tatagtgagt cgtattacgc gcgctcactg    8220
gccgtcgttt tacaacgtcg tgactgggaa aaccctggcg ttacccaact taatcgcctt    8280
gcagcacatc cccctttcgc cagctggcgt aatagcgaag aggcccgcac cgatcgccct    8340
tcccaacagt tgcgcagcct gaatggcgaa tggcgcgacg cgccctgtag cggcgcatta    8400
agcgcggcgg gtgtggtggt tacgcgcagc gtgaccgcta cacttgccag cgccctagcg    8460
cccgctcctt tcgctttctt cccttccttt ctcgccacgt tcgccggctt tccccgtcaa    8520
gctctaaatc gggggctccc tttagggttc cgatttagtg ctttacggca cctcgacccc    8580
aaaaaacttg attagggtga tggttcacgt agtgggccat cgccctgata gacggttttt    8640
cgccctttga cgttggagtc cacgttcttt aatagtggac tcttgttcca aactggaaca    8700
```

```
acactcaacc ctatctcggt ctattctttt gatttataag ggattttgcc gatttcggcc    8760
tattggttaa aaaatgagct gattaacaa aaatttaacg cgaattttaa caaaatatta    8820
acgtttacaa tttcc                                                    8835
```

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Arg Met Lys Gln Leu Glu Pro Lys Val Glu Glu Leu Leu Pro Lys Asn
1               5                   10                  15

Tyr His Leu Glu Asn Glu Val Ala Arg Leu Lys Lys Leu Val Gly Glu
            20                  25                  30

Arg
```

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Asn Tyr His Leu Glu Asn Glu Val Ala Arg Leu Lys Lys Leu
1               5                   10
```

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Gly Gly Gly Gly Ser Asn Tyr His Leu Glu Asn Glu Val Ala Arg Leu
1               5                   10                  15

Lys Lys Leu Gly Gly Gly Gly Ser
            20
```

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Gly Gly Gly Ser Asp Tyr Lys Asp Asp Asp Asp Lys
1               5                   10
```

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Ser Asp Tyr Lys Asp Asp Asp Lys Pro
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Tyr Lys Asp Asp Asp Asp Lys
1               5

<210> SEQ ID NO 8
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gacatccaga tgacacagac tacatcctcc ctgtctgcct ctctgggaga cagagtcacc        60
atcagttgca gggcaagtca ggacattagt aaatatttaa attggtatca gcagaaacca       120
gatggaactg ttaaactcct gatctaccat acatcaagat tacactcagg agtcccatca       180
aggttcagtg gcagtgggtc tggaacagat tattctctca ccattagcaa cctggagcaa       240
gaagatattg ccacttactt tgccaacag ggtaatacgc ttccgtacac gttcggaggg        300
gggaccaagc ttgagatcaa acgaactgtg gctgcaccat ctgtcttcat cttcccgcca       360
tctgatgagc agttgaaatc tggaactgcc tctgtcgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga aaacacaaa gtctacgcct gcgaagtcac ccatcagggc        600
ctgtcctcgc ccgtcacaaa gagcttcaac aggggagagt gt                         642

<210> SEQ ID NO 9
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaggtgaaac tgcaggagtc aggacctggc ctggtggcgc cctcacagag cctgtccgtc        60
acatgcactg tctcaggggt ctcattaccc gactatggtg taagctggat tcgccagcct       120
ccacgaaagg gtctggagtg gctgggagta atatggggta gtgaaaccac atactataat       180
tcagctctca aatccagact gaccatcatc aaggacaact ccaagagcca agttttctta       240
aaaatgaaca gtctgcaaac tgatgacaca gccatttact actgtgccaa acattattac       300
tacggtggta gctatgctat ggactactgg ggccaaggaa cctcagtcac cgtctcctca       360
gcctccacca agggcccatc ggtcttcccc ctggcaccct cctccaagag cacctctggg       420
ggcacagcgg ccctgggctg cctggtcaag gactacttcc ccgaaccggt gacggtgtcg       480

```
tggaactcag gcgccctgac cagcggcgtg cacaccttcc cggctgtcct acagtcctca        540
ggactctact ccctcagcag cgtggtgact gtgccctcta gcagcttggg cacccagacc        600
tacatctgca acgtgaatca caagcccagc aacaccaagg tggacaagaa agttgagccc        660
aaatcttgt                                                                669
```

<210> SEQ ID NO 10
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gaggtgaaac tgcaggagtc aggacctggc ctggtggcgc cctcacagag cctgtccgtc         60
acatgcactg tctcaggggt ctcattaccc gactatggtg taagctggat tcgccagcct        120
ccacgaaagg gtctggagtg gctgggagta atatggggta gtgaaaccac atactataat        180
tcagctctca atccagact gaccatcatc aaggacaact ccaagagcca agttttctta        240
aaaatgaaca gtctgcaaac tgatgacaca gccatttact actgtgccaa acattattac        300
tacggtggta gctatgctat ggactactgg ggccaaggaa cctcagtcac cgtctcctca        360
gcctccacca agggcccatc ggtcttcccc ctggcaccct cctccaagag cacctctggg        420
ggcacagcgg ccctgggctg cctggtcaag gactacttcc ccgaaccggt gacggtgtcg        480
tggaactcag gcgccctgac cagcggcgtg cacaccttcc cggctgtcct acagtcctca        540
ggactctact ccctcagcag cgtggtgact gtgccctcta gcagcttggg cacccagacc        600
tacatctgca acgtgaatca caagcccagc aacaccaagg tggacaagaa agttgagccc        660
aaatcttgtg acaaaactca cacatgccca ccgtgcccag cacctccagt cgccggaccg        720
tcagtcttcc tcttccctcc aaaacccaag gacaccctca tgatctcccg gacccctgag        780
gtcacatgcg tggtggtgga cgtgagccac gaagaccctg aggtcaagtt caactggtac        840
gtggacggcg tggaggtgca taatgccaag acaaagccgc gggaggagca gtacaacagc        900
acgtaccgtg tggtcagcgt cctcaccgtc ctgcaccagg actggctgaa tggcaaggag        960
tacaagtgca aggtctccaa caaaggcctc ccaagctcca tcgagaaaac catctccaaa       1020
gccaaagggc agccccgaga accacaggtg tacaccctgc ctccatcccg ggatgagctg       1080
accaagaacc aggtcagcct gacctgcctg gtcaaaggct tctatcccag cgacatcgcc       1140
gtggagtggg agagcaatgg gcagccggag aacaactaca agaccacgcc tcccgtgctg       1200
gactccgacg gctccttctt cctctacagc aagctcaccg tggacaagag caggtggcag       1260
caggggaacg tcttctcatg ctccgtgatg catgaggctc tgcacaacca ctacacgcag       1320
aagagcctct ccctgtctcc gggtaaa                                          1347
```

<210> SEQ ID NO 11
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgaaaaaga atatcgcatt tcttcttgct agcatgttcg ttttttctat tgctacaaac         60
```

```
gcatacgctg acatccagat gacccagtct ccatcctccc tgtctgcatc tgtaggagac    120
agagtcacca tcacttgccg ggcaagtcag gatgtgaata ccgcggtcgc atggtatcag    180
cagaaaccag ggaaagcccc taagctcctg atctattctg catccttctt gtatagtggg    240
gtcccatcaa ggttcagtgg cagtagatct gggacagatt tcactctcac catcagcagt    300
ctgcaacctg aagattttgc aacttactac tgtcaacagc attacactac ccctccgacg    360
ttcggccaag gtaccaagct tgagatcaaa cgaactgtgg ctgcaccatc tgtcttcatc    420
ttcccgccat ctgatgagca gttgaaatct ggaactgcct ctgtcgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgtcctcgcc cgtcacaaag agcttcaaca ggggagagtg t             711

<210> SEQ ID NO 12
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgaaaaaga atatcgcatt tcttcttgca tctatgttcg ttttttctat tgctacaaac     60
gcgtacgctg aggtgcagct ggtggagtct ggaggaggct tggtccagcc tgggggggtcc   120 ctgagactct cctgtgcagc ctctgggttc aatattaagg acacttacat ccactgggtc   180
cgccaggctc cagggaaggg gctggagtgg gtcgcacgta tttatcctac caatggttac   240
acacgctacg cagactccgt gaagggccga ttcaccatct ccgcagacac ttccaagaac   300
acggcgtatc ttcaaatgaa cagcctgaga gccgaggaca cggccgtgta ttactgttcg   360
agatggggcg gtgacggctt ctatgccatg gactactggg gccaaggaac cctggtcacc   420
gtctcctcag cctccaccaa gggcccatcg gtcttccccc tggcaccctc ctccaagagc   480
acctctgggg gcacagcggc cctgggctgc ctggtcaagg actacttccc cgaaccggtg   540
acggtgtcgt ggaactcagg cgccctgacc agcggcgtgc acaccttccc ggctgtccta   600
cagtcctcag gactctactc cctcagcagc gtggtgactg tgccctctag cagcttgggc   660
acccagacct acatctgcaa cgtgaatcac aagcccagca acaccaaggt ggacaagaaa   720
gttgagccca aatcttgtga caaaactcac aca                                 753

<210> SEQ ID NO 13
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgaaaaaga atatcgcatt tcttcttgct agcatgttcg ttttttctat tgctacaaac     60
gcatacgctc agattgtgct gagccagagc ccggcgattc tgagcgcgag cccgggcgaa   120
aaagtgacca tgacctgccg cgcgagcagc agcgtgagct atattcattg gtttcagcag   180
aaaccgggca gcagcccgaa accgtggatt tatgcgacca gcaacctggc gagcggcgtg   240
ccggtgcgct ttagcggcag cggcagcggc accagctata gcctgaccat tagccgcgtg   300
```

```
gaagcggaag atgcggcgac ctattattgc cagcagtgga ccagcaaccc gccgaccttt    360
ggcggcggca ccaagcttga gatcaaacga actgtggctg caccatctgt cttcatcttc    420
ccgccatctg atgagcagtt gaaatctgga actgcctctg tcgtgtgcct gctgaataac    480
ttctatccca gagaggccaa agtacagtgg aaggtggata cgccctcca atcgggtaac     540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctgt cctcgcccgt cacaaagagc ttcaacaggg gagagtgt                 708
```

<210> SEQ ID NO 14
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atgaaaaaga atatcgcatt tcttcttgca tctatgttcg tttttttctat tgctacaaac    60 gcgtacgctc aggtgcagct gcagcagccg ggcgcggaac tggtgaaacc gggcgcgagc    120
gtgaaaatga gctgcaaagc gagcggctat acctttacca gctataacat gcattgggtg    180
aaacagaccc cgggccgcgg cctggaatgg attggcgcga tttatccggg caacggcgat    240
accagctata accagaaatt taaggcaaa gcgaccctga ccgcggataa aagcagcagc    300
accgcgtata tgcagctgag cagcctgacc agcgaagata cgcggtgta ttattgcgcg    360 cgcagcaccct attatggcgg cgattggtat tttaacgtgt ggggcgcggg caccaccgtg    420
accgtgagcg cggcgagcac caaggggccca tcggtcttcc ccctggcacc ctcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ctgtgccctc tagcagcttg    660
ggcacccaga cctacatctg caacgtgaat cacaagccca gcaacaccaa ggtggacaag    720
aaagttgagc ccaaatcttg tgacaaaact cacaca                              756
```

<210> SEQ ID NO 15
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgagggtcc ccgctcagct cctggggctc ctgctgctct ggctcccagg tgcacgatgt    60
gacatcctgc tgacccagtc ccccgtgatc ctgtccgtgt ccctggcga gcgggtgtcc    120 ttctcctgcc gggcctccca gtccatcggc accaacatcc actggtatca gcagcggacc    180
aacggctccc ctcggctgct gatcaagtac gcctccgagt ctatctccgg catcccttcc    240
cggttctccg gctccggctc tggcaccgac ttcaccctgt ccatcaactc cgtggagtcc    300
gaggatatcg ccgactacta ctgccagcag aacaacaact ggcctaccac cttcggcgct    360
ggaaccaagc tggagctgaa gcgtacggtg gctgcaccat ctgtcttcat cttcccgcca    420
tctgatgagc agttgaaatc tggaactgcc tctgttgtgt gcctgctgaa taacttctat    480
```

```
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga gaaacacaaa gtctacgcct gcgaagtcac ccatcagggc      660
ctgagctcgc ccgtcacaaa gagcttcaac aggggagagt gttgatga                  708
```

<210> SEQ ID NO 16
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgggttgga gcctcatctt gctcttcctt gtcgctgttg ctacgcgtgt ccactcccag       60
gtgcagctga agcagtccgg ccctggcctg gtgcagcctt ccagtccct gtccatcacc      120 tgcaccgtgt ccggcttctc cctgaccaac tacggcgtgc actgggtgcg ccagtccccc      180
ggcaagggcc tggagtggct gggcgtgatc tggtccggcg gcaacaccga ctacaacacc      240
cctttcacct cccggctgtc catcaacaag gacaactcca gtcccaggt gttcttcaag       300 atgaactccc tgcagtccaa cgacaccgcc atctactact gcgccagagc cctgacctac      360
tatgactacg agttcgccta ctggggccag ggcaccctgg tgaccgtgtc cgccgctagc      420
accaagggcc catcggtctt ccccctggca cctcctcca agagcacctc tgggggcaca      480
gcggccctgg gctgcctggt caaggactac ttccccgaac cggtgacggt gtcgtggaac      540
tcaggcgccc tgaccagcgg cgtgcacacc ttcccggctg tcctacagtc ctcaggactc      600
tactccctca gcagcgtggt gaccgtgccc tccagcagct tgggcaccca gacctacatc      660
tgcaacgtga atcacaagcc cagcaacacc aaggtggaca agaaagttga gcccaaatct      720
tgtgacaaaa ctcacacatg cccaccgtgc cca                                  753
```

<210> SEQ ID NO 17
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gagaacgtgc tcacccaatc ccccgccatt atgtccgcct ccccaggcga aaaggtgaca       60
atgacctgca gggccagctc caacgtgatc agctcttacg tgcactggta ccagcaacgg      120
tccggcgcct cccctaagct gtggatctat agcacaagca acctggcttc cggcgtgcct      180
gcacggttca gcggaagcgg aagcggaaca agttactccc tcaccatttc tagcgttgaa      240
gccgaggatg ccgctacata ctattgtcaa cagtacagcg atacccccct gaccttcgga      300
gccggcacaa aactggagct caagagagca gctgcagctc ccagcgtgtt catttttcct      360
ccctccgacg aacaactgaa agcggaaca gcctctgtcg tttgcctgtt gaacaatttc      420
taccctaggg aggccaaggt ccagtggaaa gtggataacg ctctgcaaag cggaaattct      480
caggaaagcg ttaccgaaca ggattctaag gactctacat actctctgtc tagcacactc      540
acgctgagca agcagactac gagaaacac aaagtctacg cctgcgaagt cacccatcag      600
ggcctgtcct cgcccgtcac aaagagcttc aacaggggag agtgt                     645
```

```
<210> SEQ ID NO 18
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gacatccagc tgcaggagag cggccccggc ctggtgaagc ccagccagag cctgagcctg      60
acctgcagcg tgaccggcta cagcatcacc agcgcctatt actggaactg gatccggcag     120
ttccccggca caagctgga gtggatgggc tacatcagct acgacggccg gaacaactac      180
aacccaagcc tgaagaaccg gatcagcatc acccgggaca ccagcaagaa ccagtttttc     240
ctgaagctga cagcgtgac cacagaggac accgccacct attactgcgc caaggaggga      300
gactacgacg tgggcaacta ctacgccatg gactactggg gccagggcac cagcgtgacc     360
gtgtctagcg cccggaccaa gggcccagc gtgttccccc tggccccag ctctaagagc       420 accagcggcg gaaccgccgc tctgggctgc ctggtgaagg actacttccc cgagcccgtg     480
accgtgagct ggaacagcgg cgccctgacc agcggcgtgc acaccttccc cgccgtgctg     540
cagagctctg gcctgtacag cctgagcagc gtggttaccg tgcccagttc ttccctgggc     600
acccagacct acatctgcaa cgtgaaccac aagcccagca caccaaggt ggacaagaaa     660 gtggagccca agagctgc                                                   678

<210> SEQ ID NO 19
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gatattcaga tgacccagag cccgagcagc ctgagcgcga gcgtgggcga tcgcgtgacc      60
attacctgcc gcgcgagcga aagcgtggat aactatggca ttagctttat gaactggttt     120
cagcagaaac cgggcaaagc gccgaaactg ctgatttatg cggcgagcaa ccagggcagc     180
ggcgtgccga ccgctttag cggcagcggc agcggcaccg attttacct gaacattagc      240 agcctgcagc cggatgattt tgcgacctat tattgccagc agagcaaaga agtgccgtgg     300
acctttggcc agggcaccaa agtggaaatt aaacgaactg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600 acccatcagg gcctgagctc gcccgtcaca aagagcttca caggggaga gtgt            654

<210> SEQ ID NO 20
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caggtgcagc tggtgcagag cggcgcggaa gtgaaaaaac cgggcagcag cgtgaaagtg      60
```

```
agctgcaaag cgagcggcta ccctttacc gattataaca tgcattgggt gcgccaggcg    120
ccgggccagg gcctggaatg gattggctat atttatccgt ataacggcgg caccggctat    180
aaccagaaat ttaaaagcaa agcgaccatt accgcggatg aaagcaccaa caccgcgtat    240
atggaactga gcagcctgcg cagcgaagat accgcggtgt attattgcgc gcgcggccgc    300
ccggcgatgg attattgggg ccagggcacc ctggtgaccg tgagcagcgc ctccaccaag    360
ggcccatcgg tcttcccct ggcaccctcc tctagagca cctctggggg cacagcggcc    420
ctgggctgcc tggtcaagga ctacttcccc gaaccggtga cggtgtcgtg aactcaggc    480 gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtc gacaagaaag ttgagcccaa atcttgtggt    660
ggcggtcacc atcaccatca tcaccaccac                                     690
```

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105
```

<210> SEQ ID NO 22
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Pro Asp Gly Asn Tyr Trp Tyr Phe Asp Val Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
        210                 215                 220

<210> SEQ ID NO 23
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
                20                  25                  30

Ile Gly Trp Leu Gln Gln Lys Pro Gly Lys Ser Phe Lys Gly Leu Ile
            35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 24
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Leu Gln Glu Ser Gly Pro Gly Leu Val Lys Pro Ser Gln Thr Leu
1               5                   10                  15

Ser Leu Thr Cys Thr Val Ser Gly Tyr Ser Ile Ser Ser Asp Phe Ala
            20                  25                  30

Trp Asn Trp Ile Arg Gln Pro Pro Gly Lys Gly Leu Glu Trp Met Gly
        35                  40                  45

Tyr Ile Ser Tyr Ser Gly Asn Thr Arg Tyr Gln Pro Ser Leu Lys Ser
    50                  55                  60

Arg Ile Thr Ile Ser Arg Asp Thr Ser Lys Asn Gln Phe Phe Leu Lys
65                  70                  75                  80

Leu Asn Ser Val Thr Ala Ala Asp Thr Ala Thr Tyr Tyr Cys Val Thr
                85                  90                  95

Ala Gly Arg Gly Phe Pro Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys
    210                 215

<210> SEQ ID NO 25
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Gly Ile Ser Asn Asn
            20                  25                  30

Leu Asn Trp Tyr Gln Gln Lys Pro Gly Lys Ala Pro Lys Pro Leu Ile
        35                  40                  45

Tyr Tyr Thr Ser Asn Leu Gln Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Phe Thr Ser Leu Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 224
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Phe
             20                  25                  30

Asp Met Ala Trp Val Arg Gln Ala Pro Gly Lys Gly Leu Val Trp Val
         35                  40                  45

Ser Ser Ile Thr Thr Gly Gly Gly Asp Thr Tyr Tyr Ala Asp Ser Val
 50                  55                  60

Lys Gly Arg Phe Thr Ile Ser Arg Asp Asn Ala Lys Ser Thr Leu Tyr
 65                  70                  75                  80

Leu Gln Met Asp Ser Leu Arg Ser Glu Asp Thr Ala Val Tyr Tyr Cys
                 85                  90                  95

Val Arg His Gly Tyr Tyr Asp Gly Tyr His Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220
```

<210> SEQ ID NO 27
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 28
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60
```

```
Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 29
<211> LENGTH: 223
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 29

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 30
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Thr Val Ala Ala

```
                100             105             110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Ser Asn Tyr His
        165                 170                 175

Leu Glu Asn Glu Val Ala Arg Leu Lys Lys Leu Gly Gly Gly Ser
        180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 31
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Ser Asn Tyr His
        165                 170                 175

Leu Glu Asn Glu Val Ala Arg Leu Lys Lys Leu Gly Gly Gly Ser
        180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
        210                 215                 220
```

Ser Ser Pro Val Thr Lys Ser Phe Asn Arg Gly Glu Cys
225                 230                 235

<210> SEQ ID NO 32
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Asn Tyr His Leu Glu Asn Glu Val Ala
130                 135                 140

Arg Leu Lys Lys Leu Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys
225                 230

<210> SEQ ID NO 33
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

```
Gly Val Ile Trp Gly Ser Glu Thr Thr Tyr Tyr Asn Ser Ala Leu Lys
 50              55                  60
Ser Arg Leu Thr Ile Ile Lys Asp Asn Ser Lys Ser Gln Val Phe Leu
65              70                  75                  80
Lys Met Asn Ser Leu Gln Thr Asp Asp Thr Ala Ile Tyr Tyr Cys Ala
                 85                  90                  95
Lys His Tyr Tyr Tyr Gly Gly Ser Tyr Ala Met Asp Tyr Trp Gly Gln
                100                 105                 110
Gly Thr Ser Val Thr Val Ser Ser Ala Ser Thr Lys Gly Pro Ser Val
                115                 120                 125
Phe Pro Leu Ala Pro Ser Ser Asn Tyr His Leu Glu Asn Glu Val Ala
130                 135                 140
Arg Leu Lys Lys Leu Ser Gly Thr Ala Ala Leu Gly Cys Leu Val
145                 150                 155                 160
Lys Asp Tyr Phe Pro Glu Pro Val Thr Val Ser Trp Asn Ser Gly Ala
                165                 170                 175
Leu Thr Ser Gly Val His Thr Phe Pro Ala Val Leu Gln Ser Ser Gly
                180                 185                 190
Leu Tyr Ser Leu Ser Ser Val Val Thr Val Pro Ser Ser Ser Leu Gly
        195                 200                 205
Thr Gln Thr Tyr Ile Cys Asn Val Asn His Lys Pro Ser Asn Thr Lys
        210                 215                 220
Val Asp Lys Lys Val Glu Pro Lys Ser Cys Asp Lys Thr His Thr Cys
225                 230                 235                 240
Pro Pro Cys Pro Ala Pro Pro Val Ala Gly Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Lys Phe
        275                 280                 285
Asn Trp Tyr Val Asp Gly Val Glu Val His Asn Ala Lys Thr Lys Pro
        290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                325                 330                 335
Ser Asn Lys Gly Leu Pro Ser Ser Ile Glu Lys Thr Ile Ser Lys Ala
                340                 345                 350
Lys Gly Gln Pro Arg Glu Pro Gln Val Tyr Thr Leu Pro Pro Ser Arg
                355                 360                 365
Asp Glu Leu Thr Lys Asn Gln Val Ser Leu Thr Cys Leu Val Lys Gly
                370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
                420                 425                 430
Gly Asn Val Phe Ser Cys Ser Val Met His Glu Ala Leu His Asn His
                435                 440                 445
Tyr Thr Gln Lys Ser Leu Ser Leu Ser Pro Gly Lys
450                 455                 460
```

```
<210> SEQ ID NO 34
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Gly Ser Asn Tyr His Leu Glu Asn Glu Val Ala Arg Leu Lys
225                 230                 235                 240

Lys Leu

<210> SEQ ID NO 35
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60
```

```
Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Gly Ser Asn Tyr His Leu Glu Asn Glu Val Ala Arg Leu Lys
225                 230                 235                 240

Lys Leu Gly Gly Ser Asp Lys Thr His Thr Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 36
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asn Tyr His Leu Glu Asn Glu Val Ala Arg Leu Lys Lys Leu Gly Gly
1               5                   10                  15

Gly Gly Ser Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Lys Tyr Leu Asn Trp Tyr Gln Gln Lys Pro Asp Gly Thr Val Lys
50                  55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 37
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Gly Ile Ser Asn Asn
            20                  25                  30

Leu Asn Trp Tyr Gln Gln Lys Pro Gly Lys Ala Pro Lys Pro Leu Ile
        35                  40                  45

Tyr Tyr Thr Ser Asn Leu Gln Ser Gly Val Pro Ser Arg Phe Ser Gly
50                  55                  60

```
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Phe Thr Ser Leu Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Ser Asn Tyr His
                165                 170                 175

Leu Glu Asn Glu Val Ala Arg Leu Lys Lys Leu Gly Gly Gly Ser
                180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 38
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Phe
                 20                  25                  30

Asp Met Ala Trp Val Arg Gln Ala Pro Gly Lys Gly Leu Val Trp Val
             35                  40                  45

Ser Ser Ile Thr Thr Gly Gly Gly Asp Thr Tyr Tyr Ala Asp Ser Val
         50                  55                  60

Lys Gly Arg Phe Thr Ile Ser Arg Asp Asn Ala Lys Ser Thr Leu Tyr
 65                  70                  75                  80

Leu Gln Met Asp Ser Leu Arg Ser Glu Asp Thr Ala Val Tyr Tyr Cys
                 85                  90                  95

Val Arg His Gly Tyr Tyr Asp Gly Tyr His Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 39
<211> LENGTH: 5574
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
aagaaaccaa ttgtccatat tgcatcagac attgccgtca ctgcgtcttt tactggctct      60
tctcgctaac caaaccggta accctgatta tttgcacgga gtcacacttt gctatgccat     120 agcatttta tccataagat tagcggatcc tacctgacgc tttttatcgc aactctctac     180
tgtttctcca tacccgtttt tttgggctag aaataatttt gtttaacttt aagaaggaga     240
atacatcaac tagtacgcaa gttcacgtaa aagggtatc tagaggttga ggtgatttta     300
tgaaaaagaa tatcgcattt cttcttgcta gcatgttcgt tttttctatt gctacaaacg     360
catacgctga catccagatg acacagacta tcctcccct gtctgcctct ctggagaca     420 gagtcaccat cagttgcagg gcaagtcagg acattagtaa atatttaaat tggtatcagc     480

```
agaaaccaga tggaactgtt aaactcctga tctaccatac atcaagatta cactcaggag    540
tcccatcaag gttcagtggc agtgggtctg gaacagatta ttctctcacc attagcaacc    600
tggagcaaga agatattgcc acttactttt gccaacaggg taatacgctt ccgtacacgt    660
tcggaggggg gaccaagctt gagatcaaac gaactgtggc tgcaccatct gtcttcatct    720
tcccgccatc tgatgagcag ttgaaatctg gaactgcctc tgtcgtgtgc ctgctgaata    780
acttctatcc cagagaggcc aaagtacagt ggaaggtgga taacgccctc caatcgggta    840
actcccagga gagtgtcaca gagcaggaca gcaaggacag cacctacagc ctcagcagca    900
ccctgacgct gagcaaagca gactacgaga acacaaagt ctacgcctgc gaagtcaccc    960
atcagggcct gtcctcgccc gtcacaaaga gcttcaacag gggagagtgt taagctgggg   1020
atcctctaga ggttgaggtg attttatgaa aaagaatatc gcatttcttc ttgcatctat   1080
gttcgttttt tctattgcta caaacgcgta cgctgaggtg aaactgcagg agtcaggacc   1140
tggcctggtg gcgccctcac agagcctgtc cgtcacatgc actgtctcag gggtctcatt   1200
acccgactat ggtgtaagct ggattcgcca gcctccacga aagggtctgg agtggctggg   1260
agtaatatgg ggtagtgaaa ccacatacta taattcagct ctcaaatcca gactgaccat   1320
catcaaggac aactccaaga gccaagtttt cttaaaaatg aacagtctgc aaactgatga   1380
cacagccatt tactactgtg ccaaacatta ttactacggt ggtagctatg ctatggacta   1440
ctggggccaa ggaacctcag tcaccgtctc ctcagcctcc accaagggcc catcggtctt   1500
ccccctggca ccctcctcca agagcacctc tgggggcaca gcggccctgg gctgcctggt   1560
caaggactac ttccccgaac cggtgacggt gtcgtggaac tcaggcgccc tgaccagcgg   1620
cgtgcacacc ttcccggctg tcctacagtc ctcaggactc tactccctca gcagcgtggt   1680
gactgtgccc tctagcagct tgggcaccca gacctacatc tgcaacgtga atcacaagcc   1740
cagcaacacc aaggtggaca gaaagttga gcccaaatct tgtgacaaaa ctcacacata   1800
ataagtcgac cgatgccctt gagagccttc aacccagtca gctccttccg gtgggcgcgg   1860
ggcatgacta tcgtcgccgc acttatgact gtcttcttta tcatgcaact cgtaggacag   1920
gtgccaaacg gtctccagct tggctgtttt ggcggatgag agaagatttt cagcctgata   1980
cagattaaat cagaacgcag aagcggtctg ataaaacaga atttgcctgg cggcagtagc   2040
gcggtggtcc cacctgaccc catgccgaac tcagaagtga aacgccgtag cgccgatggt   2100 agtgtgggt ctccccatgc gagagtaggg aactgccagg catcaaataa aacgaaaggc   2160
tcagtcgaaa gactgggcct ttcgttttat ctgttgtttg tcggtgaacg ctctcctgag   2220
taggacaaat ccgccgggag cggatttgaa cgttgcgaag caacggcccg gagggtggcg   2280
ggcaggacgc ccgccataaa ctgccaggca tcaaattaag cagaaggcca tcctgacgga   2340 tggcctttt gcgtttctac aaactctttt tgtttatttt tctaaataca ttcaaatatg   2400
tatccgctca tgagacaata accctgataa atgcttcaat aatattgaaa aaggaagagt   2460
atgagtattc aacatttccg tgtcgccctt attccctttt ttgcggcatt ttgccttcct   2520
gtttttgctc acccagaaac gctggtgaaa gtaaaagatg ctgaagatca gttgggtgca   2580
cgagtgggtt acatcgaact ggatctcaac agcggtaaga tccttgagag ttttcgcccc   2640
gaagaacgtt ttccaatgat gagcactttt aaagttctgc tatgtggcgc ggtattatcc   2700
cgtgttgacg ccgggcaaga gcaactcggt cgccgcatac actattctca gaatgacttg   2760
gttgagtact caccagtcac agaaaagcat cttacggatg gcatgacagt aagagaatta   2820
tgcagtgctg ccataaccat gagtgataac actgcggcca acttacttct gacaacgatc   2880
```

```
ggaggaccga aggagctaac cgcttttttg cacaacatgg gggatcatgt aactcgcctt    2940
gatcgttggg aaccggagct gaatgaagcc ataccaaacg acgagcgtga caccacgatg    3000
cctgtagcaa tggcaacaac gttgcgcaaa ctattaactg gcgaactact tactctagct    3060
tcccggcaac aattaataga ctggatggag gcggataaag ttgcaggacc acttctgcgc    3120
tcggcccttc cggctggctg gtttattgct gataaatctg gagccggtga gcgtgggtct    3180
cgcggtatca ttgcagcact ggggccagat ggtaagccct cccgtatcgt agttatctac    3240
acgacgggga gtcaggcaac tatggatgaa cgaaatagac agatcgctga gataggtgcc    3300
tcactgatta agcattggta actgtcagac caagtttact catatatact ttagattgat    3360
ttaaaacttc atttttaatt taaaaggatc taggtgaaga tcctttttga taatctcatg    3420
accaaaatcc cttaacgtga gttttcgttc cactgagcgt cagacccgt agaaaagatc     3480 aaaggatctt cttgagatcc tttttttctg cgcgtaatct gctgcttgca acaaaaaaa     3540 ccaccgctac cagcggtggt ttgtttgccg gatcaagagc taccaactct ttttccgaag    3600
gtaactggct tcagcagagc gcagatacca atactgtcc ttctagtgta gccgtagtta     3660
ggccaccact tcaagaactc tgtagcaccg cctacatacc tcgctctgct aatcctgtta    3720
ccagtggctg ctgccagtgg cgataagtcg tgtcttaccg ggttggactc aagacgatag    3780
ttaccggata aggcgcagcg gtcgggctga acggggggtt cgtgcacaca gcccagcttg    3840
gagcgaacga cctacaccga actgagatac ctacagcgtg agctatgaga aagcgccacg    3900
cttcccgaag ggagaaaggc ggacaggtat ccggtaagcg gcagggtcgg aacaggagag    3960
cgcacgaggg agcttccagg gggaaacgcc tggtatcttt atagtcctgt cgggtttcgc    4020
cacctctgac ttgagcgtcg atttttgtga tgctcgtcag ggggcggag cctatggaaa     4080 aacgccagca acgcggcctt tttacggttc ctggcctttt gctggccttt tgctcacatg    4140
ttctttcctg cgttatcccc tgattctgtg gataaccgta ttaccgcctt tgagtgagct    4200
gataccgctc gccgcagccg aacgaccgag cgcagcgagt cagtgagcga ggaagcggaa    4260
gagcgcctga tgcggtattt tctccttacg catctgtgcg gtatttcaca ccgcatatgg    4320
tgcactctca gtacaatctg ctctgatgcc gcatagttaa gccagtatac actccgctat    4380
cgctacgtga ctgggtcatg gctgcgcccc gacacccgcc aacacccgct gacgcgccct    4440
gacgggcttg tctgctcccg gcatccgctt acagacaagc tgtgaccgtc tccgggagct    4500
gcatgtgtca gaggttttca ccgtcatcac cgaaacgcgc gaggcagcag atcaattcgc    4560
gcgcgaaggc gaagcggcat gcataatgtg cctgtcaaat ggacgaagca gggattctgc    4620
aaaccctatg ctactccgtc aagccgtcaa ttgtctgatt cgttaccaat tatgacaact    4680
tgacggctac atcattcact tttcttcac aaccggcacg gaactcgctc gggctggccc     4740
cggtgcattt tttaaatacc gcgagaaat agagttgatc gtcaaaacca acattgcgac     4800
cgacggtggc gataggcatc cgggtggtgc tcaaaagcag cttcgcctgg ctgatacgtt    4860
ggtcctcgcg ccagcttaag acgctaatcc ctaactgctg gcggaaaaga tgtgacagac    4920
gcgacggcga caagcaaaca tgctgtgcga cgctggcgat atcaaaattg ctgtctgcca    4980
ggtgatcgct gatgtactga caagcctcgc gtacccgatt atccatcggt ggatggagcg    5040
actcgttaat cgcttccatg cgccgcagta acaattgctc aagcagattt atcgccagca    5100
gctccgaata gcgcccttcc ccttgcccgg cgttaatgat ttgcccaaac aggtcgctga    5160
aatgcggctg gtgcgcttca tccgggcgaa agaacccgt attggcaaat attgacggcc    5220
```

-continued

```
agttaagcca ttcatgccag taggcgcgcg gacgaaagta aacccactgg tgataccatt    5280
cgcgagcctc cggatgacga ccgtagtgat gaatctctcc tggcgggaac agcaaaatat    5340
cacccggtcg gcaaacaaat tctcgtccct gattttcac caccccctga ccgcgaatgg     5400
```
*(Note: "gattttcac" in the image reads* `gattttttcac` *— verify)*

```
tgagattgag aatataacct ttcattccca gcggtcggtc gataaaaaaa tcgagataac    5460
cgttggcctc aatcggcgtt aaacccgcca ccagatgggc attaaacgag tatcccggca    5520
gcaggggatc attttgcgct tcagccatac ttttcatact cccgccattc agag          5574
```

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Gly Ser
1               5

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Gly Ser
1

<210> SEQ ID NO 42
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Ser
1

<210> SEQ ID NO 43
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ser
1

<210> SEQ ID NO 44
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Any amino acid

<400> SEQUENCE: 44

Xaa Ser
1

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1 to 5 "Gly Gly Gly
      Gly Ser" repeating units

<400> SEQUENCE: 45

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1 to 5 "Gly Gly
      Ser" repeating units

<400> SEQUENCE: 46

Gly Gly Ser Gly Gly Ser Gly Gly Ser Gly Gly Ser Gly Gly Ser
1               5                   10                  15

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Ser Ser Ser Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser
1               5

<210> SEQ ID NO 49
<211> LENGTH: 2
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ser
1
```

PEPTIDIC CHIMERIC ANTIGEN RECEPTOR T CELL SWITCHES AND USES THEREOF

CROSS-REFERENCE

This application is a continuation of International Application No. PCT/US14/60684, filed Oct. 15, 2014, which claims the benefit of priority from U.S. provisional application Ser. No. 61/891,347, filed Oct. 15, 2013; U.S. provisional application Ser. No. 61/895,704, filed Oct. 25, 2013; U.S. provisional application Ser. No. 62/009,054, filed Jun. 6, 2014; U.S. provisional application Ser. No. 62/030,526, filed Jul. 29, 2014; and U.S. provisional application Ser. No. 62/030,514, filed Jul. 29, 2014; which are all incorporated by reference in their entirety.

SEQUENCE LISTING

The instant application contains a Sequence Listing which has been submitted electronically in ASCII format and is hereby incorporated by reference in its entirety. Said ASCII copy, created on Dec. 2, 2014, is named 41135-728-601SL.txt and is 83,208 bytes in size.

BACKGROUND OF THE INVENTION

Immunotherapies are becoming attractive alternatives to chemotherapies, including immunotherapies that use adoptive transfer of genetically modified T cells to "reteach" the immune system to recognize and eliminate malignant tumor cells. Genetically modified T cells express chimeric antigen receptors, which generally consist of a signaling endodomain, a CD3-zeta transmembrane domain and an extracellular single-chain variable fragment (scFv) derived from a monoclonal antibody which gives the receptor specificity for a tumor-associated antigen on a target malignant cell. Upon binding the tumor-associated antigen via the chimeric antigen receptor, the chimeric antigen receptor expressing T cell (CAR T-cell) mounts an immune response that is cytotoxic to the malignant cell. Such therapies can circumvent chemotherapy resistance and have been shown to be active against relapsed/refractory disease, resulting in sustained remissions for some chronic lymphocytic leukemia (CLL) and acute lymphoblastic leukemia (ALL) patients. However, these therapies require further investigation and optimization, as they caused undesirable effects such as toxic lymphophenia, chronic hypogammaglobulinemia for hematological targets, fatal off-target cytolysis for solid tumor targets, persistent B cell aplasia with the use of anti-CD19 antibody expressing CAR T-cells, and, in some cases, death.

Introduction of a switch, which controls the activity of the CAR T-cell, would allow CAR T-cell activity and associated immune responses to be turned off after neoplastic cells are eliminated and would allow B cells to reproliferate. Recent preclinical studies have demonstrated that CAR T-cell systems can be controlled through an antibody-based switch, wherein the antibody binds the target cell (e.g. cancer cell), blocking the CAR T-cell from binding the target cell and "switching off" CAR-T activity. While these systems conceptually allow for switchable targeting of tumors using CAR T-cells, they may suffer from a series of limitations. Non-specific labeling of antibodies using cysteines or lysines produces heterogeneous products which includes variants that may be non-functional, have unpredictable pharmacokinetics and/or immunogenicity, and that may be difficult to optimize.

SUMMARY OF THE INVENTION

Disclosed herein are chimeric antigen receptor-effector cell switches comprising: a peptidic antigen that binds a chimeric antigen receptor on an effector cell; and a targeting moiety that binds a cell surface molecule on a target cell. The peptidic antigen may be based on or derived from a naturally occurring peptide. The peptidic antigen may be based on or derived from a non-human peptide. The peptidic antigen may be based on or derived from a eukaryotic peptide. The peptidic antigen may be based on or derived from a peptide, wherein the peptide is expressed by a yeast. The peptidic antigen may be based on or derived from a yeast transcription factor GCN4. The peptidic antigen may comprise a non-naturally occurring peptide. The peptidic antigen may comprise a synthetic peptide tag. The peptidic antigen may be based on or derived from a sequence selected from SEQ ID NOs: 2-7. The peptidic antigen may comprise a sequence that is at least about 50% homologous to a peptide sequence selected from SEQ ID NOs: 2-7. The targeting moiety may comprise a targeting peptide. The targeting moiety may comprise a targeting antibody or antibody fragment. The targeting antibody or antibody fragment may be selected from the group consisting of: an immunoglobulin, an Fc null immunoglobulin, and a Fab, and fragments thereof. The targeting moiety may be selected from the group consisting of: an anti-EGFR antibody, an anti-Her2 antibody, anti-EGFRvIII antibody, an anti-CD33 antibody, an anti-CLL-1 antibody, an anti-CEA antibody, an anti-CD19 antibody, an anti-CD22 antibody, an anti-BCMA antibody, and an anti-CS1 antibody, and fragments thereof. The targeting antibody or antibody fragment may comprise a light chain and a heavy chain pair, wherein the light chain and heavy chain are encoded by nucleic acid sequences based on or derived from nucleic acid sequence pairs selected from the group consisting of: SEQ ID NOs: 8 and 9; SEQ ID NOs: 8 and 10; SEQ ID NOs: 11 and 12; SEQ ID NOs. 13 and 14; SEQ ID NOs: 15 and 16; SEQ ID NOs: 17 and 18; and SEQ ID NOs: 19 and 20. The targeting antibody or antibody fragment may comprise a light chain and a heavy chain pair, wherein the light chain and heavy chain are encoded by amino acid sequences based on or derived from amino acid sequence pairs selected from the group consisting of: SEQ ID NOs: 21 and 22; SEQ ID NOs: 23 and 24; SEQ ID NOs. 25 and 26; SEQ ID NOs: 27 and 28; and SEQ ID NOs: 27 and 29. The chimeric antigen receptor-effector cell switch may comprise a light chain and a heavy chain pair, wherein the light chain and heavy chain are encoded by amino acid sequences based on or derived from amino acid sequence pairs selected from the group consisting of: SEQ ID NOs: 30 and 29; SEQ ID NOs: 36 and 29; SEQ ID NOs: 31 and 28; SEQ ID NOs: 27 and 32; SEQ ID NOs: 27 and 33; SEQ ID NOs: 27 and 34; and SEQ ID NOs: 27 and 35. The peptidic antigen may be fused to a terminus of the targeting antibody or antibody fragment. The peptidic antigen may be fused to a region of the targeting antibody or antibody fragment selected from the group consisting of: an N terminus of a light chain, a C terminus of a light chain, an N terminus of a heavy chain, a C terminus of a Fab heavy chain and a C terminus of a constant region heavy chain. The peptidic antigen may be grafted into the targeting moiety. The targeting moiety may comprise a targeting antibody or antibody fragment. The peptidic antigen may be grafted into a region of the targeting antibody or antibody fragment selected from a $CH_1$ domain, a $CH_2$ domain, a $CH_3$ domain, a CL domain, a VH domain, a VL domain and a hinge region. The peptidic antigen may be grafted between two regions of the targeting antibody or antibody fragment selected from a CH$_1$ domain, a CH$_2$ domain, a CH$_3$ domain, a CL domain, a VH domain, a VL domain, a heavy chain, a light chain and a hinge region, wherein the two regions are adjacent. The peptidic antigen may be grafted into a loop of the targeting antibody or antibody fragment. The peptidic antigen may be grafted into a loop of a constant domain of the targeting antibody or antibody fragment. The peptidic antigen may be grafted between the hinge region and a heavy chain constant domain of the targeting antibody or antibody fragment. The peptidic antigen may replace one or more amino acids of the targeting antibody or antibody fragment. The peptidic antigen may be grafted into the targeting antibody or antibody fragment without replacing an amino acid. The chimeric antigen receptor-effector cell may further comprise a linker that links the peptidic antigen and the targeting moiety. The linker may be a peptide that links the peptidic antigen and the targeting moiety, wherein the targeting moiety comprises a targeting polypeptide. The linker may comprise about 1 to about 20 amino acids. The linker may comprise a sequence based on or derived from a sequence selected from SEQ ID NOs: 38-42. The peptidic antigen may comprise a yeast transcription factor GCN4 or homolog thereof and the targeting moiety is selected from the group consisting of: an anti-Her2 antibody, an anti-BCMA antibody, an anti-CD19 antibody, an anti-CEA antibody and fragments thereof. The target cell may be a cancer cell. The cell surface molecule may be a tumor associated antigen. The cell surface molecule may be selected from the group consisting of: a cluster of differentiation protein, a receptor, an integral membrane protein and a glycoprotein. The homogeneity of the chimeric antigen receptor-effector cell switch may be at least about 90%.

Further disclosed herein are pharmaceutical compositions comprising: a chimeric antigen receptor-effector cell switch comprising: a peptidic antigen that binds a chimeric antigen receptor on an effector cell; and a targeting moiety that binds a cell surface molecule on a target; and a pharmaceutically acceptable salt, excipient and/or vehicle.

Disclosed herein are kits comprising: a chimeric antigen receptor-effector cell switch comprising: a peptidic antigen that binds a chimeric antigen receptor on an effector cell; and a targeting moiety that binds a cell surface molecule on a target cell; and a chimeric antigen receptor-effector cell comprising a chimeric antigen receptor that binds to the peptidic antigen of the chimeric antigen receptor-effector cell switch. The targeting moiety may comprise a targeting peptide. The targeting moiety comprises a targeting antibody or antibody fragment. The peptidic antigen is grafted within the targeting moiety. The kit may comprise a first chimeric antigen receptor-effector cell switch and a second chimeric antigen receptor-effector cell switch, wherein the first chimeric antigen receptor-effector cell switch comprises a first peptidic antigen and a first targeting moiety and the second chimeric antigen receptor-effector cell switch comprises a second peptidic antigen and a second targeting moiety. The first peptidic antigen and the second peptidic antigen may be the same. The first targeting moiety may bind a first cell surface molecule on a first target cell and the second targeting moiety may bind a second cell surface molecule on a second target cell, wherein the first cell surface molecule and the second cell surface molecule are different. The effector cell may be selected from a T cell, an effector B cell, a natural killer cell, a macrophage and a progenitor thereof. The effector cell may be selected from a naive T cell, a memory stem cell T cell, a central memory T cell, an effector memory T cell, a helper T cell, a CD4+ T cell, a CD8+ T cell, a CD8/CD4+ T cell, an αβ T cell, a γδ T cell, a cytotoxic T cell, a natural killer T cell, a natural killer cell, a macrophage.

Further disclosed herein are chimeric antigen receptors that bind a peptidic antigen of a chimeric antigen receptor-effector cell switch. The chimeric antigen receptor may comprise an antibody or antibody fragment that binds the peptidic antigen of a chimeric antigen receptor-effector cell switch. The antibody fragment or antibody fragment may bind a eukaryotic antigen. The antibody or antibody fragment may bind a non-naturally occurring peptide. The antibody fragment may be an scFv. The antibody or antibody fragment may be selected from an anti-yeast transcription factor GCN4 antibody, an anti-FLAG® antibody, an anti-HTP antibody and fragments thereof. The chimeric antigen receptor may be encoded by a polynucleotide based on or derived from SEQ ID NO: 1.

Disclosed herein are effector cells comprising a chimeric antigen receptor, wherein the chimeric antigen receptor that binds a peptidic antigen of a chimeric antigen receptor-effector cell switch. The effector cells may be T cells. The effector cells may comprise one or more polynucleotides based on or derived from SEQ ID NO: 1.

Further disclosed herein are vectors comprising a polynucleotide having a sequence that encodes a chimeric antigen receptor-effector cell switch, wherein the chimeric antigen receptor-effector cell switch comprises peptidic antigen and a targeting moiety, wherein the targeting moiety comprises a peptide and binds a cell surface molecule on a target cell.

Disclosed herein are vectors comprising a first polynucleotide having a first sequence that encodes a heavy chain of a targeting antibody or antibody fragment; a second polynucleotide having a second sequence that encodes a light chain of a targeting antibody or antibody fragment; and a third polynucleotide having a third sequence that encodes a peptidic antigen, wherein expression of the vector produces a chimeric antigen receptor-effector cell switch. The third sequence may be adjacent to a sequence selected from the first sequence and the second sequence. The third sequence may be located within a sequence selected from the first sequence and the second sequence.

Further disclosed herein are methods of producing a chimeric antigen receptor-effector cell switch, comprising expressing from one or more polynucleotide vectors: a first sequence that encodes a heavy chain of a targeting antibody or antibody fragment; a second sequence that encodes a light chain of a targeting antibody or antibody fragment; and a third sequence that encodes a peptidic antigen, wherein expression of the vector produces a chimeric antigen receptor-effector cell switch.

BRIEF DESCRIPTION OF THE DRAWINGS

FIG. 1A illustrates a general overview of chimeric antigen receptor-T cell (CAR T-cell) and CAR T-cell switch therapy with switches disclosed herein. Lymphocytes are isolated from a subject and an expression vector encoding a chimeric antigen receptor is subsequently introduced to the lymphocytes to produce chimeric antigen receptor expressing cells. Resulting engineered lymphocytes are administered to the subject, along with a CAR T-cell switch.

FIG. 1B illustrates a CAR T-cell switch, comprising a peptide that is bound by the chimeric antigen receptor of the CAR T-cell and a targeting antibody that is selective for a target cell. Binding of the CAR T-cell switch to the CAR T-cell induces an immune response that would be cytotoxic to the malignant cell also bound to the CAR T-cell switch.

FIG. 5A shows a non-reducing SDS-PAGE gel of anti-CD19 antibodies or antibody fragments with a GCN4 peptide grafted or fused to various regions or domains of the antibodies or antibody fragments.

FIG. 5B shows a reducing SDS-PAGE gel of anti-CD19 antibodies or antibody fragments with a GCN4 peptide grafted or fused to various regions or domains of the antibodies or antibody fragments.

Figure 7A:
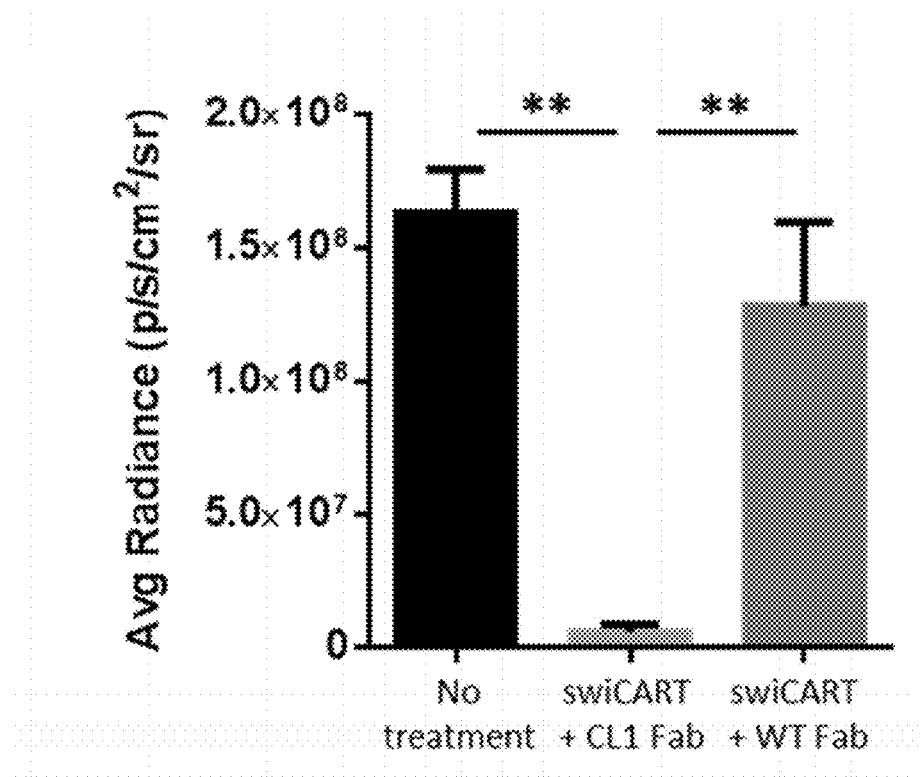
Figure 7B:
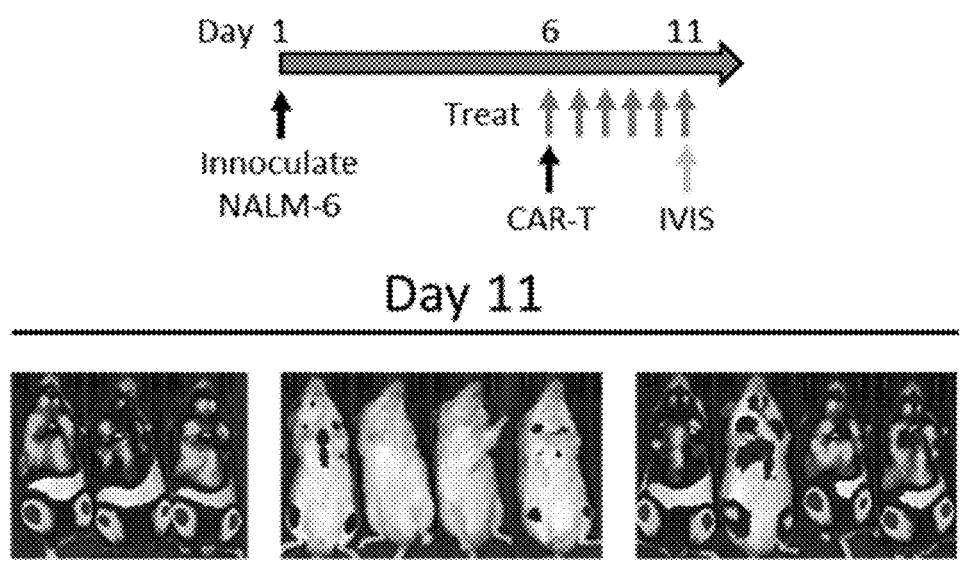

FIG. 7A-B shows in vivo efficacy of an anti-CD19 Fab-GCN4 peptide CAR T-cell switch and an anti-GCN4 CAR T-cell in a xenograft tumor mouse model. FIG. 7A shows quantification of tumors in untreated versus treated mice. FIG. 7B depicts in vivo treatment regimen and visualization of tumor cells in untreated versus treated mice.

Figure 8:
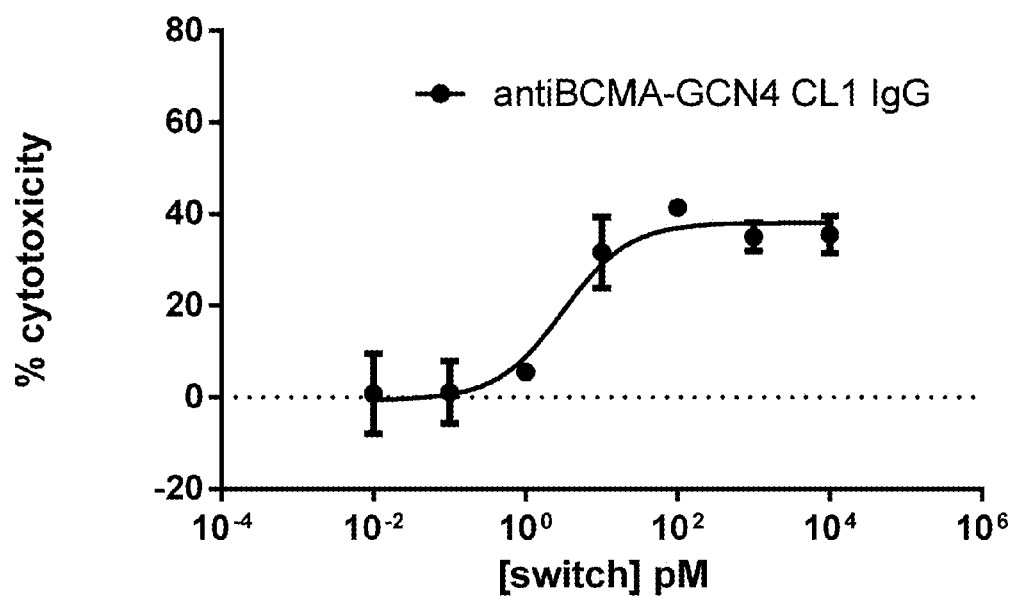

FIG. 8 shows cytotoxicity of an anti-GCN4 CAR T-cell and CAR T-cell switch (anti-BCMA antibody -GCN4 peptide grafted into the light chain constant domain) against BCMA-positive cells (OPM2).

DETAILED DESCRIPTION OF THE INVENTION

Figure 1A:
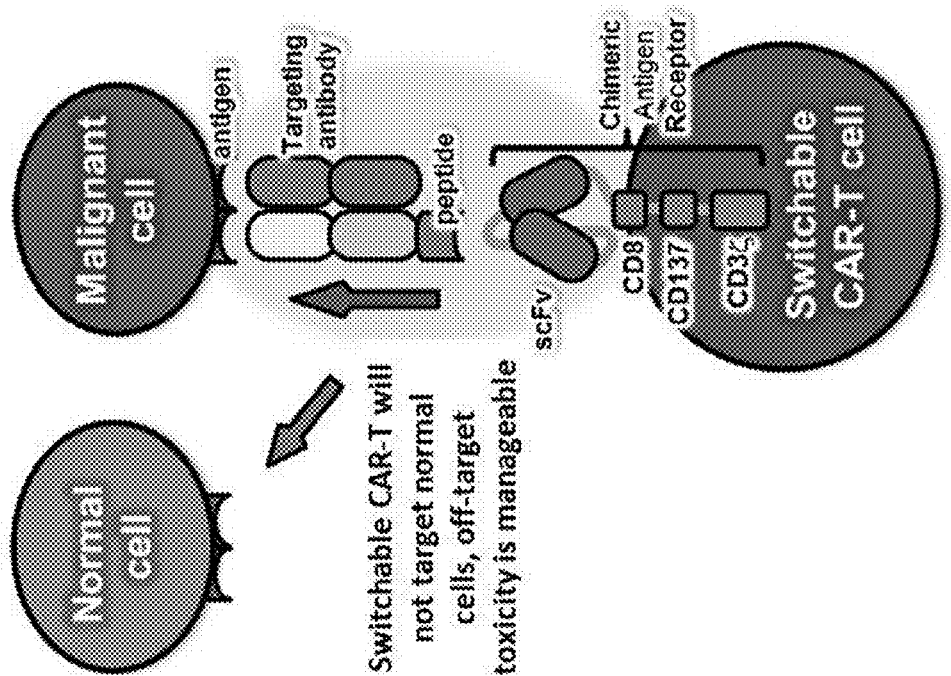
Figure 1B:
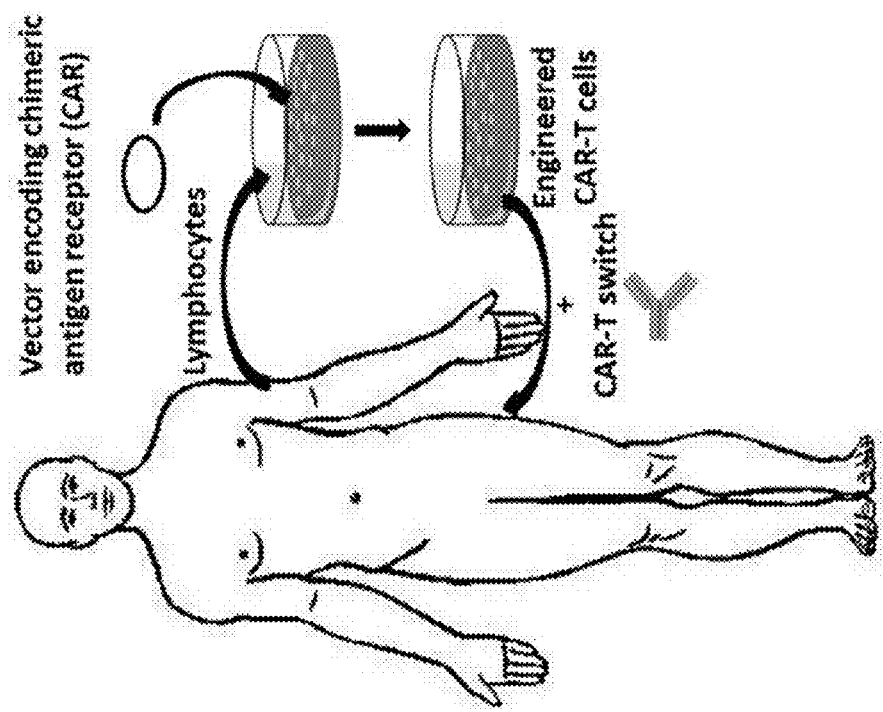

Current chimeric antigen receptor T cell (CAR T-cell) therapies can be unreliable due to lack of means to control CAR T-cell activity. Disclosed herein are compositions and methods for selectively activating and deactivating chimeric antigen receptor T cells, which may provide for safer and more versatile immunotherapies than those currently being tested and administered. Disclosed herein are switchable chimeric antigen receptor effector cells (CAR-ECs) and chimeric antigen receptor effector cell (CAR-EC) switches, wherein the CAR-EC switches have a first region that is bound by a chimeric antigen receptor on the CAR-EC and a second region that binds a cell surface molecule on target cell, thereby stimulating an immune response from the CAR-EC that is cytotoxic to the bound target cell. In general, the CAR-EC is a T cell. In this way, the CAR-EC switch may act as an "on-switch" for CAR-EC activity. Activity may be "turned off" by reducing or ceasing administration of the switch. These CAR-EC switches may be used with CAR-ECs disclosed herein, as well as existing CAR T-cells, for the treatment of a disease or condition, such as cancer, wherein the target cell is a malignant cell. Such treatment may be referred to herein as switchable immunotherapy, for which an exemplary schematic overview is depicted in FIG. 1.

The CAR-EC switches disclosed herein comprise a first region that binds a cell surface molecule on a target cell, and a second region that is bound by a chimeric antigen receptor. In general the first region is a targeting polypeptide. The targeting polypeptide may be a targeting antibody or antibody fragment that binds an antigen on the target cell. Alternatively or additionally, the first region may comprise a non-peptide small molecule (e.g. vitamin, metabolite). The second region, referred to herein as a chimeric antigen binding peptidic antigen (CAR-BP), comprises a peptide. For simplicity, the term chimeric antigen binding peptidic antigen may simply be referred to herein as a peptidic antigen. In general, the CAR-BP is fused to a terminus of the targeting polypeptide or grafted within the targeting polypeptide. Fusing or grafting the CAR-BP to the targeting polypeptide may be carried out by cloning one or more polynucleotides encoding the first region and the second region into a polynucleotide expression vector, in a desired order or combination.

Methods of treating a disease or condition comprising administering the CAR-EC switches, disclosed herein, may provide for a titratable response, improved safety and/or cessation of CAR-EC activity by reducing or ceasing administration of the CAR-EC switch. In contrast to other approaches of controlling CAR-EC activity, which "turn off" CAR-EC activity by competing with the target cell surface molecule for binding the CAR, the CAR-EC switches disclosed herein, generally function as CAR-EC activators or "on" switches.

Further disclosed herein are CAR-EC platforms including CAR-EC switches and effector cells comprising universal chimeric antigen receptors (CAR) that can bind multiple CAR-EC switches, providing for sequential targeting of one or more types of target cells (e.g. treatment of heterogeneous tumors). The CAR may comprise an ultra-high affinity antibody or antibody fragment (e.g. scFv) to the switch. Methods of producing the CAR-EC switches disclosed herein may advantageously provide for control of CAR-EC cell activity, titration of off-target reactivity, abrogation of tumor lysis syndrome (TLS), attenuation of cytokine release syndrome (CRS), and/or optimization of CAR-EC switch binding by affinity, valency, geometry, length and/or chemistry through site-specific grafting/fusing of CAR-EC switch peptides/antibodies.

Unless otherwise specified, the terms "switch" and "CAR-EC switch", as used herein, are used interchangeably and may refer to a peptide switch. The antibody portion of the peptide antibody switch may comprise at least a portion of an antibody or an entire antibody. For example, the antibody portion of the peptide antibody switch may comprise at least a portion of a heavy chain, a portion of a light chain, a portion of a variable region, a portion of a constant region, a portion of a complementarity determining region (CDR), or a combination thereof. The antibody portion of the peptide antibody switch and/or hapten antibody switch may comprise at least a portion of the Fc (fragment, crystallizable) region. The antibody portion of the peptide antibody switch may comprise at least a portion of the complementarity determining region (e.g., CDR1, CDR2, CDR3). The antibody portion of the peptide antibody switch may comprise at least a portion of the Fab (fragment, antigen-binding) region. The peptide switch may be a peptide-Fab switch.

Before the present methods, kits and compositions are described in greater detail, it is to be understood that this invention is not limited to particular method, kit or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, kits and compositions are provided for producing CAR-EC platforms and CAR-EC switches used to bring an effector cell together with a target in a subject. These methods, kits and compositions find therapeutic use in a number of diseases. For example, heterogeneous tumors and blood cell malignancies (e.g. acute lymphoblastic leukemia and chronic lymphocytic leukemia) may be more effectively treated with a CAR-EC platform when the length, valency and orientation of the CAR-EC switch linkage as well as the CAR-EC switch cell targeting moiety is optimized. Heterogeneous tumors may be more effectively treated with multiple CAR-EC switches that target more than one tumor antigens. Advantages, and features of the invention will become apparent to those persons skilled in the art upon reading the details of the compositions and methods as more fully described below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

IA. Peptide Switch

Disclosed herein are chimeric antigen receptor-effector cell switches comprising: a peptidic antigen that binds a chimeric antigen receptor on an effector cell; and a targeting moiety that binds a cell surface molecule on a target. The targeting moiety may be a targeting polypeptide, comprising a targeting peptide that binds the cell surface molecule. The targeting moiety may be a targeting antibody or antibody fragment comprising the targeting peptide, wherein the targeting peptide is an antigen binding site of the targeting antibody or antibody fragment. The targeting peptide may be at least a portion of an antibody fragment and the cell surface molecule may be an antigen. The targeting moiety may comprise one or more peptides that recognize and/or bind one or more antigens. The targeting moiety may comprise one or more peptides that recognize and/or bind only one antigen. The peptidic antigen may not comprise an antibody or antibody fragment that recognizes and/or binds an antigen.

Further disclosed herein are CAR-EC switches comprising: a peptidic antigen that binds a CAR (CAR-BP) on an effector cell, wherein the CAR-BP; and a targeting polypeptide that binds a cell surface molecule on a target cell. The peptidic antigen may be fused to a terminus of the targeting polypeptide. The peptidic antigen may be grafted into the targeting polypeptide (e.g. between chosen amino acids of the targeting polypeptide). The targeting polypeptide may be fused to a terminus of the peptidic antigen. The targeting polypeptide may be grafted into the peptidic antigen (e.g. between chosen amino acids of the peptidic antigen).

Disclosed herein are CAR-EC switches comprising: a peptidic antigen that binds a CAR (CAR-BP) on an effector cell; and a targeting antibody or antibody fragment that binds an antigen on a target. The targeting antibody or antibody fragment may be selected from an immunoglobulin, a Fab, a Fab', a F(ab')$_2$ and an scFv. The targeting antibody or antibody fragment may comprise a light chain. The targeting antibody or antibody fragment may comprise a heavy chain.

The peptidic antigen may be fused to an N terminus of the light chain of the targeting antibody or antibody fragment. The peptidic antigen may be fused to a C terminus of the light chain of the targeting antibody or antibody fragment. The peptidic antigen may be fused to an N terminus of the heavy chain of the targeting antibody or antibody fragment. The peptidic antigen may be fused to a C terminus of the heavy chain of the targeting antibody or antibody fragment. The peptidic antigen may be fused to an N terminus of a VL domain of the targeting antibody or antibody fragment. The peptidic antigen may be fused to an N terminus of a VH domain of the targeting antibody or antibody fragment. The peptidic antigen may be fused to a C terminus of a CL domain of the targeting antibody or antibody fragment. The peptidic antigen may be fused to a C terminus of an Fc domain of the targeting antibody or antibody fragment. The peptidic antigen may be fused to an N terminus of a VL domain of an IgG. The peptidic antigen may be fused to an N terminus of a VH domain of an IgG. The peptidic antigen may be fused to a C terminus of a CL domain of an IgG. The peptidic antigen may be fused to a C terminus of an Fc domain of an IgG. The peptidic antigen may be fused to an N terminus of a VL domain of a Fab. The peptidic antigen may be fused to an N terminus of a VH domain of a Fab. The peptidic antigen may be fused to a C terminus of a CL domain of a Fab. The peptidic antigen may be fused to a C terminus of a $CH_1$ domain of the Fab.

The peptidic antigen may be grafted into an internal site of a targeting antibody or antibody fragment (e.g. between chosen amino acids of the targeting antibody or antibody fragment). The peptidic antigen may be grafted into a heavy chain of a targeting antibody or antibody fragment. The peptidic antigen may be grafted into a light chain of a targeting antibody or antibody fragment. The peptidic antigen may be grafted into a constant domain/region of a targeting antibody or antibody fragment. The peptidic antigen may be grafted into a variable domain/region of a targeting antibody or antibody fragment. The peptidic antigen may be grafted into an internal site of a Fab. The peptidic antigen may be grafted into an internal site of an immunoglobulin (e.g. IgG). The peptidic antigen may be grafted into a domain of the targeting antibody or fragment thereof selected from a CL domain, a $CH_1$ domain, a $CH_2$ domain, a $CH_3$ domain, a VL domain, a VH domain and a hinge domain. The peptidic antigen may be grafted between two domains of the antibody or fragment thereof selected from a CL domain, a $CH_1$ domain, a $CH_2$ domain, a $CH_3$ domain, a VL domain, a VH domain and a hinge domain, wherein the two domains are adjacent. The peptidic antigen may be grafted into a CL domain of the antibody or fragment thereof. The peptidic antigen may be grafted into a $CH_1$ domain of the antibody or fragment thereof. The peptidic antigen may be grafted into a hinge domain of the antibody or fragment thereof. The peptidic antigen may be grafted into a loop of the antibody or fragment thereof. The peptidic antigen may be grafted into a CL domain loop of the antibody or fragment thereof.

The CAR-BP may be grafted into the C terminus of the antibody or antibody fragment and therefore the distance between the chimeric antigen receptor and the target may differ substantially depending on the size of CAR-EC switch (approximately 40 Å for scFv, 70 Å for Fab, and 120 Å for IgG). While a larger distance may negatively impact efficacy in vitro, the increased residence time of the full length antibody may be superior in vivo.

The CAR-BP may further comprise a linker. The linker may provide the CAR-EC switch flexibility, length or geometry optimal for facilitating an interaction or effect of the CAR-EC on the target cell. The CAR-BP may further comprise one or more linkers. The CAR-BP may comprise two linkers. The linker may comprise a peptide. The linker may be at least about 1, at least about 2, at least about 3, at least about 4, at least about 5, at least about 6, at least about 7, at least about 8, at least about 9 or at least about 10 amino acids in length. The one or more linkers may comprise about 5, about 10, about 15, about 20, about 25, about 30, about 35, about 40, about 45, about 50, about 55, about 60, about 70, about 80, about 90 or about 100 amino acids. The linker may be located at the N terminus or the C terminus of the CAR-BP to graft the CAR-BP to the targeting polypeptide. A first linker may be fused to the N terminus of the CAR-BP and a second linker may be fused to the C terminus of the CAR-BP. The linker may be comprised of the sequence $(GGGGS)_n$, (SEQ ID NO: 45), wherein n may be 1, 2, 3, 4, 5 or more. The linker may be comprised of the sequence $(GGS)_n$, (SEQ ID NO: 46), wherein n may be 1, 2, 3, 4, 5 or more. The CAR-BP may be grafted into an internal site of the targeting polypeptide with a linker on either end of the CAR-BP. The linker may comprise a sequence selected from SEQ ID NOS: 40-44.

The Peptidic Antigen

The peptidic antigen (CAR-BP) may be a peptide that is bound by a chimeric antigen receptor (CAR). The peptidic antigen may have high proteolytic stability and low immunogenicity in humans relative to peptides in general. The CAR-BP may be selected from a hormone, a cytokine, a chemokine, a growth factor, a cell adhesion molecule, a signaling peptide, a receptor, a cell surface peptide and fragments thereof. The CAR-BP may be a peptoid. The CAR-BP may be a peptide nucleic acid (PNA). The CAR-BP may be a ligand or a fragment thereof. The ligand may be a hormonal ligand. The ligand may be a peptide ligand. The CAR-BP may be a cyclic peptide. The CAR-BP may be a linear peptide. The CAR-BP may have a length of between about 2 and about 10, about 10 and about 20, about 20 and about 30, about 30 and about 40, about 40 and about 50, about 50 and about 60, about 60 and about 70, about 70 and about 80, and about 80 and about 90 amino acids. The CAR-BP may be an antigen. The CAR-BP may be an epitope. The CAR-BP may be a nonlinear epitope. The CAR-BP may further comprise a second peptide.

The peptidic antigen may not comprise an antibody or antibody fragment. The peptidic antigen may comprise less than 10 amino acids of an antibody or antibody fragment. The peptidic antigen may comprise less than 12 amino acids of an antibody or antibody fragment. The peptidic antigen may comprise less than 15 amino acids of an antibody or antibody fragment. The peptidic antigen may comprise less than 20 amino acids of an antibody or antibody fragment. The peptidic antigen may comprise less than 22 amino acids of an antibody or antibody fragment. The peptidic antigen may comprise less than 30 amino acids of an antibody or antibody fragment. The peptidic antigen may not comprise a paratope of an antibody or antibody fragment.

Disclosed herein are chimeric antigen receptor effector cell switches comprising a targeting moiety and a peptidic antigen, wherein the targeting moiety is a targeting polypeptide. The targeting polypeptide may comprise a targeting antibody or antibody fragment. The targeting antibody or antibody fragment may comprise a variable domain. The variable domain may be selected from a VH domain and a VL domain. The peptidic antigen may not be located at or near the N terminus of the VH domain. The peptidic antigen may not be located at or near the N terminus of the VL domain.

The peptidic antigen may comprise a non-naturally occurring peptide. The peptidic antigen may comprise a synthetic peptide. The peptidic antigen may comprise a non-animal peptide (e.g. a peptide not expressed in an animal). The peptidic antigen may comprise a non-mammalian peptide. The peptidic antigen may comprise a non-human peptide. The peptide may comprise a peptide derived from a plant, a yeast, a bacteria, a reptile, a bird or an insect.

The peptidic antigen may comprise a myc-tag. The peptidic antigen may comprise His-tag. The peptidic antigen may comprise an HA-tag. The peptidic antigen may comprise peridinin chlorophyll protein complex. The peptidic antigen may comprise green fluorescent protein (GFP). The peptidic antigen may comprise red fluorescent protein (RFP). The peptidic antigen may comprise phycoerythrin (PE). The peptidic antigen may comprise streptavidin. The peptidic antigen may comprise avidin. The peptidic antigen may comprise horse radish peroxidase (HRP). The peptidic antigen may comprise alkaline phosphatase. The peptidic antigen may comprise glucose oxidase. The peptidic antigen may comprise glutathione-S-transferase (GST). The peptidic antigen may comprise maltose binding protein. The peptidic antigen, by non-limiting example, may be a c-myc tag, polyhistidine tag, V5, VSVG, softag 1, softag 3, express tag, S tag, palmitoylation, nitrosylation, SUMO tag, thioredoxin, poly(NANP), poly-Arg, calmodulin binding protein, PurF fragment, ketosteroid isomerase, PaP3.30, TAF12 histone fold domain, FKBP-tag, SNAP tag, Halo-tag, peptides from RNAse I. The peptidic antigen may comprise a protease cleavage site. The protease cleavage site may be recognized by thrombin, factor Xa, TEV protease or enterokinase.

The peptidic antigen may be a small linear hydrophilic peptide. The small linear hydrophilic peptide may comprise a linker. The small linear hydrophilic peptide may be a hydrophilic target peptide (HTP). The small linear hydrophilic peptide may comprise the sequence GGGGSDYKDDDDK (SEQ ID NO: 5). The small linear hydrophilic peptide may comprise the sequence GGGGSDYKDDDDKP (SEQ ID NO: 6). The small linear hydrophilic peptide may consist essentially of the sequence GGGGSDYKDDDDK (SEQ ID NO: 5). The small linear hydrophilic peptide may consist essentially of the sequence GGGGSDYKDDDDKP (SEQ ID NO: 6). The small linear hydrophilic peptide may be at least about 50% homologous to SEQ ID NOs: 5 or 6. The small linear hydrophilic peptide may be at least about 60% homologous to SEQ ID NOs: 5 or 6. The small linear hydrophilic peptide may be at least about 70% homologous to SEQ ID NOs: 5 or 6. The small linear hydrophilic peptide may be at least about 80% homologous to SEQ ID NOs: 5 or 6. The small linear hydrophilic peptide may be at least about 85% homologous to SEQ ID NOs: 5 or 6. The small linear hydrophilic peptide may be at least about 90% homologous to SEQ ID NOs: 5 or 6. The small linear hydrophilic peptide may have reduced non-specific binding relative to other peptides known in the art. The small linear hydrophilic peptide may have reduced non-specific binding and reduced fusion protein instability relative to other peptides disclosed herein. The peptidic antigen may comprise a FLAG® tag (SEQ ID NO: 7) or a derivative or a homolog thereof.

The peptide may be based on or derived from a naturally occurring peptide. The peptide may be based on or derived from a human peptide. The peptide may be based on or derived from an peptide expressed in animal selected from a chimpanzee, a monkey, a rat, a mouse, a bird, a fish, a pig, a horse, a cow, a goat, a chicken, a rabbit and a guinea pig. The peptide may be based on or derived from a mammalian peptide. The peptide may be based on or derived from a non-mammalian peptide. The peptide may be based on or derived from a peptide expressed in a plant. The peptide may be based on or derived from a peptide expressed in a bacterium. The peptide may be based on or derived from a prokaryotic peptide. The peptide may be based on or derived from a eukaryotic peptide. The peptide may be based on or derived from a peptide expressed by a yeast. The peptidic antigen may comprise a yeast transcription factor GCN4 peptide or a derivative or a homolog thereof. The yeast transcription factor GCN4 peptide may comprise the sequence RMKQLEPKVEELLPKNYHLENEVARLK-KLVGER (SEQ ID NO: 2). The yeast transcription factor GCN4 peptide may comprise the sequence NYHLENE-VARLKKL (SEQ ID NO: 3). The yeast transcription factor GCN4 peptide may consist essentially of the sequence RMKQLEPKVEELLPKNYHLENEVARLKKLVGER (SEQ ID NO: 2). The yeast transcription factor GCN4 peptide may consist essentially of the sequence NYHLE-NEVARLKKL (SEQ ID NO: 3). The yeast transcription factor GCN4 peptide may comprise a portion of SEQ ID NO. 2. The portion of SEQ ID NO. 2 may be at least 4 amino acids long. The portion of SEQ ID NO. 2 may be about 4, about 5, about 6, about 7, about 8, about 9, about 10, about 11, about 12 or about 13 amino acids long. The yeast transcription factor GCN4 peptide may be at least about 50% homologous to SEQ ID NOs: 2 or 3. The yeast transcription factor GCN4 peptide may be at least about 60% homologous to SEQ ID NOs: 2 or 3. The yeast transcription factor GCN4 peptide may be at least about 70% homologous to SEQ ID NOs: 2 or 3. The yeast transcription factor GCN4 peptide may be at least about 80% homologous to SEQ ID NOs: 2 or 3. The yeast transcription factor GCN4 peptide may be at least about 85% homologous to SEQ ID NOs: 2 or 3. The yeast transcription factor GCN4 peptide may be at least about 90% homologous to SEQ ID NOs: 2 or 3. The CAR-EC switch may comprise a yeast GCN4 peptide and one or more linkers. The CAR-EC switch may comprise SEQ ID NO. 4.

The Targeting Moiety

The targeting moiety may bind to a cell surface molecule on a target. The cell surface molecule may comprise an antigen. The cell surface molecule may be selected from a protein, a lipid moiety, a glycoprotein, a glycolipid, a carbohydrate, a polysaccharide, a nucleic acid, an MHC-bound peptide, or a combination thereof. The cell surface molecule may comprise parts (e.g., coats, capsules, cell walls, flagella, fimbrae, and toxins) of bacteria, viruses, and other microorganisms. The cell surface molecule may be expressed by the target cell. The cell surface molecule may not be expressed by the target cell. By way of non-limiting example, the cell surface molecule may be a ligand expressed by a cell that is not the target cell and that is bound to the target cell or a cell surface molecule of the target cell. Also, by non-limiting example, the cell surface molecule may be a toxin, exogenous molecule or viral protein that is bound to a cell surface or cell surface receptor of the target cell.

The targeting polypeptide may be a targeting antibody or antibody fragment. The targeting antibody or antibody fragment may be an immunoglobulin (Ig). The immunoglobulin may selected from an IgG, an IgA, an IgD, an IgE, an IgM, a fragment thereof or a modification thereof. The immunoglobulin may be IgG. The IgG may be IgG1. The IgG may be IgG2. The IgG may have one or more Fc mutations for modulating endogenous T cell FcR binding to the CAR-EC switch. The IgG may have one or more Fc mutations for removing the Fc binding capacity to the FcR of FcR-positive cells. Removal of the Fc binding capacity may reduce the opportunity for crosslinking of the CAR-EC to FcR positive cells, wherein crosslinking of the CAR-EC to FcR positive cells would activate the CAR-EC in the absence of the target cell. As such, modulating the endogenous T cell FcR binding to the CAR-EC switch may reduce an ineffective or undesirable immune response. The one or more Fc mutations may remove a glycosylation site. The one or more Fc mutations may be selected from E233P, L234V, L235A, delG236, A327G, A330S, P331 S, N297Q and any combination thereof. The one or more Fc mutations may be in IgG1. The one or more Fc mutations in the IgG1 may be L234A, L235A, or both. Alternatively, or additionally, the one or more Fc mutations in the IgG1 may be L234A, L235E, or both. Alternatively, or additionally, the one or more Fc mutations in the IgG1 may be N297A. Alternatively, or additionally, the one or more mutations may be in IgG2. The one or more Fc mutations in the IgG2 may be V234A, V237A, or both.

The targeting antibody or antibody fragment may be an Fc null immunoglobulin or a fragment thereof.

As used herein, the term "antibody fragment" refers to any form of an antibody other than the full-length form. Antibody fragments herein include antibodies that are smaller components that exist within full-length antibodies, and antibodies that have been engineered. Antibody fragments include, but are not limited to, Fv, Fc, Fab, and (Fab')2, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, alternative scaffold non-antibody molecules, and bispecific antibodies. Unless specifically noted otherwise, statements and claims that use the term "antibody" or "antibodies" may specifically include "antibody fragment" and "antibody fragments."

The targeting antibody fragment may be human, fully human, humanized, human engineered, non-human, and/or chimeric antibody. The non-human antibody may be humanized to reduce immunogenicity to humans, while retaining the specificity and affinity of the parental non-human antibody. Chimeric antibodies may refer to antibodies created through the joining of two or more antibody genes which originally encoded for separate antibodies. A chimeric antibody may comprise at least one amino acid from a first antibody and at least one amino acid from a second antibody, wherein the first and second antibodies are different. At least a portion of the antibody or antibody fragment may be from a bovine species, a human species, or a murine species. At least a portion of the antibody or antibody fragment may be from a rat, a goat, a guinea pig or a rabbit. At least a portion of the antibody or antibody fragment may be from a human. At least a portion of the antibody or antibody fragment antibody may be from cynomolgus monkey.

The targeting antibody or antibody fragment may be based on or derived from an antibody or antibody fragment from a mammal, bird, fish, amphibian, reptile. Mammals include, but are not limited to, carnivores, rodents, elephants, marsupials, rabbits, bats, primates, seals, anteaters, cetaceans, odd-toed ungulates and even-toed ungulates. The mammal may be a human, non-human primate, mouse, sheep, cat, dog, cow, horse, goat, or pig.

The targeting antibody or an antibody fragment may target an antigen selected from, by non-limiting example, CD19, Her2, CLL-1, CD33, EGFRvIII, CD20, CD22, BCMA or a fragment thereof. The antigen may comprise a wildtype antigen. The antigen may comprise one or more mutations.

The targeting antibody or antibody fragment may be an anti-CD19 antibody or a fragment thereof. The targeting polypeptide may be an anti-CD22 antibody. The targeting polypeptide may be an anti-BCMA antibody or a fragment thereof. The targeting polypeptide may be an anti-CS1 antibody or a fragment thereof. The targeting polypeptide may be an anti-EGFRvIII antibody or a fragment thereof. The targeting polypeptide may be an anti-Her2 antibody or a fragment thereof. The targeting polypeptide may comprise an anti-CD20 antibody or antibody fragment. The targeting polypeptide may comprise rituximab. The targeting polypeptide may comprise an anti-EGFR antibody or antibody fragment. The targeting polypeptide may comprise an anti-CEA antibody or antibody fragment. The targeting polypeptide may comprise an anti-CLL-1 antibody or antibody fragment. The targeting polypeptide may comprise an anti-CD33 antibody or antibody fragment. The targeting polypeptide may not comprise an anti-EpCAM antibody or fragment thereof.

The targeting antibody or antibody fragment may be selected any commercially available antibody. The targeting antibody or antibody fragment may be selected from ado-trastuzumab emtansine, alemtuzumab, bevacizumab, brentuximab, vedotin, gemtuzumab, ozogamicin, ipilimumab, ibritumomab, tiuxetan, panitumumab, cetuximab, erbitux, rituximab, trastuzumab and fragments thereof.

The targeting antibody or antibody fragment may comprise an anti-CD19 antibody or fragment thereof. The targeting antibody or fragment thereof may comprise a light chain of the anti-CD19 antibody or fragment thereof. The light chain of the anti-CD19 antibody or fragment thereof may be encoded by a nucleotide sequence based on or derived from SEQ ID NO. 8. The nucleotide sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 8. The targeting antibody or fragment thereof may comprise a heavy chain of the anti-CD19 antibody or fragment thereof. The heavy chain of the anti-CD19 antibody or fragment thereof may be encoded by a sequence based on or derived from SEQ ID NO. 9. The nucleotide sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 9.

The targeting antibody or antibody fragment may comprise an anti-CD19 antibody or fragment thereof. The targeting antibody or fragment thereof may comprise a light chain of the anti-CD19 antibody or fragment thereof. The light chain of the anti-CD19 antibody or fragment may comprise an amino acid sequence based on or derived from SEQ ID NO. 27. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 27. The targeting antibody or fragment thereof may comprise a heavy chain of the anti-CD19 or fragment thereof. The targeting antibody or fragment thereof may comprise a heavy chain of an anti-CD19 IgG. The heavy chain of the anti-CD19 IgG may comprise a sequence based on or derived from SEQ ID NO. 28. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 28. The targeting antibody or fragment thereof may comprise a heavy chain of an anti-CD19 Fab. The heavy chain of the anti-CD19 Fab may comprise a sequence based on or derived from SEQ ID NO. 29. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 29.

The targeting antibody or antibody fragment may comprise a nucleotide sequence selected from SEQ ID NOs: 8-20. The targeting polypeptide may be based on or derived from a nucleotide selected from SEQ ID NOs: 8-20. The targeting antibody or antibody fragment may comprise an amino acid sequence selected from SEQ ID NOs: 21-29. The targeting polypeptide may be based on or derived from an amino acid sequence selected from SEQ ID NOs: 21-29.

Disclosed herein are chimeric antigen receptor effector cell (CAR-EC) switches comprising a peptidic antigen and a targeting moiety that binds a cell surface molecule on a target cell. Generally, binding of the effector cell and the target cell to the CAR-EC switch construct brings the target cell into proximity with the effector cell sufficiently close for an activity of the effector cell to have an effect on the target cell. For example, when the T cell and the target cell are bound to the CAR-EC switch, the T cell may produce an immune response that has a cytotoxic effect on the target cell.

The CAR-EC switches may interact with a plurality of target cells. The target cell may be an infected cell. The target cell may be a pathogenically infected cell. The target cell may be a diseased cell. The target cell may be a genetically-modified cell. The target cell may not be a host cell. The target cell may come from an invading organism (e.g. yeast, worm, bacteria, fungus). Further disclosed herein are CAR-EC switches that interact with a molecule on a non-cell target. The non-cell target may be a virus or a portion thereof. The non-cell target may be a fragment of a cell. The non-cell target may be an extracellular matrix component or protein.

The target cell may be derived from a tissue. The tissue may be selected from brain, esophagus, breast, colon, lung, glia, ovary, uterus, testes, prostate, gastrointestinal tract, bladder, liver, thymus, bone and skin. The target cell may be derived from one or more endocrine glands. Alternatively, or additionally, the target cell may be derived from one or more endocrine glands. The endocrine gland may be a lymph gland, pituitary gland, thyroid gland, parathyroid gland, pancreas, gonad or pineal gland.

The target cell may be selected from a stem cell, a pluripotent cell, a hematopoietic stem cell or a progenitor cell. The target cell may a circulating cell. The target cell may be an immune cell.

The target cell may be a cancer stem cell. The target cell may be a cancer cell. The cancer cell may be derived from a tissue. The tissue may be selected from, by way of non-limiting example, a brain, an esophagus, a breast, a colon, a lung, a glia, an ovary, a uterus, a testicle, a prostate, a gastrointestinal tract, a bladder, a liver, a thyroid and skin. The cancer cell may be derived from bone. The cancer cell may be derived from blood. The cancer cell may be derived from a B cell, a T cell, a monocyte, a thrombocyte, a leukocyte, a neutrophil, an eosinophil, a basophil, a lymphocyte, a hematopoietic stem cell or an endothelial cell progenitor. The cancer cell be derived from a CD19-positive B lymphocyte. The cancer cell may be derived from a stem cell. The cancer cell may be derived from a pluripotent cell. The cancer cell may be derived from one or more endocrine glands. The endocrine gland may be a lymph gland, pituitary gland, thyroid gland, parathyroid gland, pancreas, gonad or pineal gland.

The cancer cell may be a CD19-positive cell. The cancer cell may be a CD19-positive B lymphocyte. The cancer cell may be a Her2-positive cell. The Her2-positive cell may be a Her2-positive breast cancer cell. The target cell may be a BCMA-positive cell. The cancer cell may be a BCMA-positive multiple myeloma cell. The cancer cell may be a CS1-positive cell. The CS1-positive cell may be a multiple myeloma cell. The cancer cell may be a EGFRvIII-positive cell. The cancer cell may be a EGFRvIII-positive glioblastoma cell. The cancer cell may be a CD20-positive cell. The cancer cell may be a CD22-positive cell.

The cell surface molecule may be an antigen. The antigen may be at least a portion of a surface antigen or a cell surface marker on a cell. The antigen may be a receptor or a co-receptor on a cell. The antigen may refer to a molecule or molecular fragment that may be bound by a major histocompatibility complex (MHC) and presented to a T-cell receptor. The term "antigen" may also refer to an immunogen. The immunogen may provoke an adaptive immune response if injected on its own into a subject. The immunogen may induce an immune response by itself. The antigen may be a superantigen, T-dependent antigen or a T-independent antigen. The antigen may be an exogenous antigen. Exogenous antigens are typically antigens that have entered the body from the outside, for example by inhalation, ingestion, or injection. Some antigens may start out as exogenous antigens, and later become endogenous (for example, intracellular viruses). The antigen may be an endogenous antigen. The endogenous antigen may be an antigen that has been generated within cells as a result of normal cell metabolism, or because of pathogenic infections (e.g., viral, bacterial, fungal, parasitic). The antigen may be an autoantigen. The autoantigen may be a normal protein or complex of proteins (and sometimes DNA or RNA) that is recognized by the immune system of patients suffering from a specific autoimmune disease. These antigens should, under normal conditions, not be the target of the immune system, but, due to genetic and/or environmental factors, the normal immunological tolerance for such an antigen is not present in these patients. The antigen may be present or over-expressed due to a condition or disease. The condition or disease may be a cancer or a leukemia. The condition may be an inflammatory disease or condition. The condition or disease may be a metabolic disease. The condition may be a genetic disorder.

The cell surface molecule may be an antigen that has been designated as a tumor antigen. Tumor antigens or neoantigens may be antigens that are presented by MHC I or MHC II molecules on the surface of tumor cells. These antigens may sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens may also be on the surface of the tumor in the form of, for example, a mutated receptor, in which case they may be recognized by B cells. Unless otherwise specified, the terms "tumor antigen," "tumor specific antigen" and "tumor associated antigen," are used interchangeably herein.

The cell surface molecule may be a receptor. The receptor may be an extracellular receptor. The receptor may be a cell surface receptor. By way of non-limiting example, the receptor may bind a hormone, a neurotransmitter, a cytokine, a growth factor or a cell recognition molecule. The receptor may be a transmembrane receptor. The receptor may be an enzyme-linked receptor. The receptor may be a G-protein couple receptor (GPCR). The receptor may be a growth factor receptor. By way of non-limiting example, the growth factor receptor may be selected from an epidermal growth factor receptor, a fibroblast growth factor receptor, a platelet derived growth factor receptor, a nerve growth factor receptor, a transforming growth factor receptor, a bone morphogenic protein growth factor receptor, a hepatocyte growth factor receptor, a vascular endothelial growth factor receptor, a stem cell factor receptor, an insulin growth factor receptor, a somatomedin receptor, an erythropoietin receptor and homologs and fragments thereof. The receptor may be a hormone receptor. The receptor may be an insulin receptor. By way of non-limiting example, the receptor may selected from an eicosanoid receptor, a prostaglandin receptor, an estrogen receptor, a follicle stimulating hormone receptor, a progesterone receptor, a growth hormone receptor, a gonadotropin-releasing hormone receptor, homologs thereof and fragments thereof. The receptor may be an adrenergic receptor. The receptor may be an integrin. The receptor may be an Eph receptor. The receptor may be a luteinizing hormone receptor. The cell surface molecule may be at least about 50% homologous to a luteinizing hormone receptor. The receptor may be an immune receptor. By way of non-limiting example, the immune receptor may be selected from a pattern recognition receptor, a toll-like receptor, a NOD like receptor, a killer activated receptor, a killer inhibitor receptor, an Fc receptor, a B cell receptor, a complement receptor, a chemokines receptor and a cytokine receptor. By way of non-limiting example, the cytokine receptor may be selected from an interleukin receptor, an interferon receptor, a transforming growth factor receptor, a tumor necrosis factor receptor, a colony stimulating factor receptor, homologs thereof and fragments thereof. The receptor may be a receptor kinase. The receptor kinase may be a tyrosine kinase receptor. The receptor kinase may be a serine kinase receptor. The receptor kinase may be a threonine kinase receptor. By way of non-limiting example, the receptor kinase may activate a signaling protein selected from a Ras, a Raf, a PI3K, a protein kinase A, a protein kinase B, a protein kinase C, an AKT, an AMPK, a phospholipase, homologs thereof and fragments thereof. The receptor kinase may activate a MAPK/ERK signaling pathway. The receptor kinase may activate Jak, Stat or Smad.

The cell surface molecule may be a non-receptor cell surface protein. The cell surface molecule may be a cluster of differentiation proteins. By way of non-limiting example, the cell surface molecule may be selected from CD34, CD31, CD117, CD45, CD11b, CD15, CD24, CD114, CD182, CD14, CD11a, CD91, CD16, CD3, CD4, CD25, CD8, CD38, CD22, CD61, CD56, CD30, CD13, CD33, fragments thereof, and homologs thereof.

The cell surface molecule may be a molecule that does not comprise a peptide. The cell surface molecule may comprise a lipid. The cell surface molecule may comprise a lipid moiety or a lipid group. The lipid moiety may comprise a sterol. The lipid moiety may comprise a fatty acid. The antigen may comprise a glycolipid. The cell surface molecule may comprise a carbohydrate.

Disclosed herein are CAR-EC switches comprising (a) a chimeric antigen receptor binding peptidic antigen comprising a peptide from a yeast transcription factor peptide; and (b) a targeting polypeptide. The yeast transcription factor peptide may be a GCN4 peptide. The targeting polypeptide may comprise a targeting antibody or antibody fragment. The targeting antibody or antibody fragment may comprise a heavy chain of an antibody. The targeting antibody or antibody fragment may comprise a light chain of an antibody. The targeting antibody or antibody fragment may comprise a Fab of an antibody. The targeting antibody or antibody fragment may comprise an anti-CD19 antibody or a fragment thereof. The targeting antibody or antibody fragment may comprise an anti-Her2 antibody or a fragment thereof. The targeting antibody or antibody fragment may be selected from an anti-CS1 antibody, an anti-BCMA antibody, an anti-EGFRvIII antibody, an anti-CD20 antibody, an anti-EGFR antibody, an anti-CEA antibody, an anti-CLL-1 antibody, an anti-CD33 antibody and fragments thereof.

Further disclosed herein are CAR-EC switches comprising (a) a CAR binding region comprising a hydrophilic target peptide (HTP) tag; and (b) a targeting polypeptide. The targeting polypeptide may comprise a targeting antibody or antibody fragment. The targeting antibody or antibody fragment may comprise a heavy chain of an antibody. The targeting antibody or antibody fragment may comprise a light chain of an antibody. The targeting antibody or antibody fragment may comprise a Fab of an antibody. The targeting antibody or antibody fragment may comprise an anti-CD19 antibody or a fragment thereof. The targeting antibody or antibody fragment may comprise an anti-Her2 antibody or a fragment thereof. The targeting antibody or antibody fragment may be selected from an anti-CS1 antibody, an anti-BCMA antibody, an anti-EGFRvIII antibody, an anti-CD20 antibody, an anti-EGFR antibody, an anti-CEA antibody, an anti-CLL-1 antibody, an anti-CD33 antibody and fragments thereof.

The chimeric antigen receptor-effector cell switch may comprise a heavy chain selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 50% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 60% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 70% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 80% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 90% homologous to a sequence selected from SEQ ID NO. 32, SEQ ID NO. 33, SEQ ID NO. 34, SEQ ID NO. 35 and SEQ ID NO. 38.

The chimeric antigen receptor-effector cell switch may comprise a light chain selected from SEQ ID NO. 30, SEQ ID NO. 31, SEQ ID NO. 36 and SEQ ID NO. 37. The chimeric antigen receptor-effector cell switch may comprise a light chain that is at least 50% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 60% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 70% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 80% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 90% homologous to a sequence selected from SEQ ID NO. 30, SEQ ID NO. 31, SEQ ID NO. 36 and SEQ ID NO. 37.

The chimeric antigen receptor-effector cell switch may comprise a heavy chain of SEQ ID NO. 29 and a light chain of SEQ ID NO. 30. The chimeric antigen receptor-effector cell switch may comprise a heavy chain of SEQ ID NO. 29 and a light chain of SEQ ID NO. 36. The chimeric antigen receptor-effector cell switch may comprise a heavy chain of SEQ ID NO. 28 and a light chain of SEQ ID NO. 31. The chimeric antigen receptor-effector cell switch may comprise a heavy chain of SEQ ID NO. 32 and a light chain of SEQ ID NO. 27. The chimeric antigen receptor-effector cell switch may comprise a heavy chain of SEQ ID NO. 33 and a light chain of SEQ ID NO. 27. The chimeric antigen receptor-effector cell switch may comprise a heavy chain of SEQ ID NO. 34 and a light chain of SEQ ID NO. 27. The chimeric antigen receptor-effector cell switch may comprise a heavy chain of SEQ ID NO. 35 and a light chain of SEQ ID NO. 27. The chimeric antigen receptor-effector cell switch may comprise a heavy chain of SEQ ID NO. 38 and a light chain of SEQ ID NO. 37.

Multivalent CAR-EC Switches

Exemplified herein are CAR-EC switches comprising a chimeric antigen receptor binding peptidic antigen (CAR-BP) and a targeting polypeptide. However, one skilled in the art would understand that these switches could further comprise additional targeting polypeptides and/or additional CAR-BPs. One or more CAR-BPs may be grafted into one or more grafting sites of the targeting polypeptide. One or more CAR-BPs may be fused to one or more termini of the targeting polypeptide. This may be advantageous, as several grafting/fusing sites may be predicted to provide optimal binding of the CAR-BP to the CAR. For example, a first CAR-BP may be grafted into a first domain of the targeting polypeptide and a second CAR-BP may be grafted into a second domain of the targeting polypeptide. The first domain and the second domain may be the same. The first domain and the second domain may be different. By way of non-limiting example, the first CAR-BP may be grafted into a light chain of a targeting antibody or antibody fragment and a second CAR-BP may be grafted into heavy chain of the targeting antibody or antibody fragment. The first CAR-BP may be fused to a first terminus of the targeting polypeptide and a second CAR-BP may be fused to a second terminus of the targeting polypeptide. By way of non-limiting example, the first CAR-BP may be fused to a C terminus of a light chain of a targeting antibody or antibody fragment and a second CAR-BP may be fused to an N terminus of a heavy chain of the targeting antibody or antibody fragment. The first CAR-BP may be fused to a terminus of the targeting polypeptide and a second CAR-BP may be grafted within a domain of the targeting polypeptide. The first CAR-BP and the second CAR-BP may be the same or similar, such that the CAR-EC switch may be used with a CAR-EC cell that expresses one CAR. The first CAR-BP and the second CAR-BP may be different, such that the CAR-EC switch may be used with a CAR-EC cell that expresses one or more CARs or multiple CAR-EC cells that express different CARs.

The peptide switches disclosed herein may comprise one or more CAR-BPs. The peptide switches disclosed herein may comprise two or more CAR-BPs. The peptide switches disclosed herein may comprise three or more CAR-BPs. The peptide switches disclosed herein may comprise 1, 2, 3, 4, 5, 6, 7 or more CAR-BPs. The one or more CAR-BPs may be fused or grafted to the targeting polypeptide via one or more linkers. Thus, the peptide switches disclosed herein may comprise one or more linkers (e.g., L1, L2). The peptide switches disclosed herein may comprise two or more linkers. The peptide switches disclosed herein may comprise three or more linkers. The peptide switches disclosed herein may comprise 1, 2, 3, 4, 5, 6, 7 or more linkers.

IB. Peptide-Small Molecule Switch

Further disclosed herein are CAR-EC switches comprising a CAR binding region and a targeting moiety, wherein the CAR binding region is a CAR-binding peptidic antigen and the targeting moiety is a non-peptidic small molecule. The non-peptidic small molecule may be a cell-targeting molecule, a chemical ligand, a nucleic acid, a vitamin, a substrate or a substrate analog. The non-peptidic small molecule may not comprise two amino acids, wherein the two amino acids are connected by an amide bond. The CAR-EC switch may further comprise a linker. The CAR-binding peptidic antigen (CAR-BP) and the small molecule may be site-specifically linked. The CAR-binding peptidic antigen may comprise an unnatural amino acid. The CAR-binding peptidic antigen and the small molecule may be site-specifically linked by the unnatural amino acid. The small molecule may bind a cell surface molecule on a target cell. The cell surface molecule may be selected from an antigen, a protein, a peptide, a lipid, a sterol, a glycolipid and a cell surface marker. The CAR-binding peptidic antigen may be selected from FLAG® tag, yeast transcription factor GCN4 and a hydrophilic target peptide (HTP). The small molecule may be 2-[3-(1,3-dicarboxypropyl)ureido]pentanedioic acid. The small molecule may be folate. The CAR-EC switch may further comprise a linker.

Disclosed herein are methods of producing CAR-EC switches comprising conjugating the CAR binding region to the targeting moiety, wherein the CAR-EC switches comprise a CAR binding region and a targeting moiety, wherein the CAR binding region is a CAR-binding peptidic antigen and the targeting moiety is a small molecule. The method may further comprise conjugating the small molecule to the linker to create a small molecule-linker intermediate. The small molecule or the small molecule-linker intermediate may comprise one or more reactive functional groups that may react with a complementary reactive functional group on the CAR-BP, previous to incorporation into the CAR-EC switch. The linker or the small molecule-linker intermediate may be bifunctional. The linker or the small molecule-linker intermediate may be heterobifunctional.

The small molecule-linker intermediate or the CAR-EC switch may be the product of a bioorthogonal reaction, non-limiting examples of which are reviewed in Kim et al., Curr Opin Chem Bio 17:412-419 (2013). The small molecule-linker intermediate, linker or the CAR-EC switch may comprise an oxime, a tetrazole, a Diels Alder adduct, a hetero Diels Alder adduct, an aromatic substitution reaction product, a nucleophilic substitution reaction product, an ester, an amide, a carbamate, an ether, a thioether, or a Michael reaction product. The small molecule-linker intermediate, linker or the CAR-EC switch be a cycloaddition product, a metathesis reaction product, a metal-mediated cross-coupling reaction product, a radical polymerization product, an oxidative coupling product, an acyl-transfer reaction product, or a photo click reaction product. The cycloaddition may be a Huisgen-cycloaddition. The cycloaddition may be a copper-free [3+2] Huisgen-cycloaddition. The cycloaddition may be a Diels-Alder reaction. The cycloaddition may be a hetero Diels-Alder reaction. The small molecule-linker intermediate may be the product of an enzyme-mediated reaction. The small molecule-linker intermediate may be a product of a transglutaminase-mediated reaction, non-limiting examples of which are described in Lin et al., J. Am. Chem. Soc. 128:4542-4543 (2006) and WO 2013/093809. The small molecule-linker intermediate, linker or the CAR-EC switch may comprise a disulfide bridge that connects two cysteine residues, such as Thio-Bridge™ technology by PolyTherics. The small molecule-linker intermediate, linker or the CAR-EC switch may comprise a maleimide bridge that connects two amino acid residues. The small molecule-linker intermediate, linker or the CAR-EC switch may comprise a maleimide bridge that connects two cysteine residues.

The small molecule-linker intermediate or linker may comprise an alkoxy-amine (or aminooxy) group, azide group and/or cyclooctyne group at one or more termini. The small molecule-linker intermediate or linker may comprise an alkoxy-amine at one terminus and an azide group at the other terminus. The small molecule-linker intermediate or linker may comprise an alkoxy-amine at one terminus and a cyclooctyne group at the other terminus. The alkoxy-amine may form a stable oxime with a ketone group on an amino acid. The alkoxy-amine may form a stable oxime with a ketone group on an unnatural amino acid. The ketone group may be on a p-acetyl phenylalanine (pAcF).

II. Chimeric Antigen Receptor (CAR)

Disclosed herein are CAR-EC switches that regulate the activities of a cell expressing a chimeric antigen receptor (CAR). The chimeric antigen receptor may comprise an extracellular domain, transmembrane domain and intracellular domain. The extracellular domain may bind to the peptidic antigen (e.g. CAR-BP) of the CAR-EC switch. The extracellular domain may comprise an antibody or antibody fragment that binds to the CAR-BP of the CAR-EC switch (a CAR-antibody). The CAR-antibody may comprise at least a portion of an antibody. In some instances, the CAR-antibody is not a full-length antibody. The CAR-antibody may comprise at least a portion of an immunoglobulin or fragment thereof. The immunoglobulin or fragment thereof may be selected from the group consisting of an scFv, a di-scFv, a bi-scFv, a Fab, an Fc, an F(ab')$_2$, a pFc', a nanobody, an affibody, a DARPin, a diabody, a camelid, an engineered T cell receptor and a monobody. The immunoglobulin may be selected from the group consisting of an IgA1, an IgA2, an IgD, an IgM, an IgE, an IgG1, an IgG2, an IgG3, and an IgG4. The CAR-antibody may comprise at least a portion of a single chain variable fragment (scFv). The CAR-antibody may be human, fully human, humanized, human engineered, non-human, and/or chimeric antibody.

The CAR-antibody may have a binding affinity for the CAR-BP of less than about 0.01 pM, about 0.02 pM, about 0.03 pM, about 0.04 pM, about 0.05 pM, about 0.06 pM, about 0.07 pM, about 0.08 pM, about 0.09 pM, about 0.1 pM, about 0.2 pM, 0.3 pM, about 0.4 pM, about 0.5 pM, about 0.6 pM, about 0.7 pM, about 0.8 pM, about 0.9 pM or about 1 pM, about 2 pM, about 3 pM, about 4 pM, about 5 pM, about 6 pM, about 7 pM, about 8 pM, about 9 pM, about 10 pM, about 0.01 nM, about 0.02 nM, about 0.03 nM, about 0.04 nM, about 0.05 nM, about 0.06 nM, about 0.07 nM, about 0.08 nM, about 0.09 nM, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 2 nM, about 2.5 nM, about 3 nM, about 4 nM, about 5 nM, about 6 nM, about 7 nM, about 8 nM, about 9 nM, about 10 nM, about 12 nM, about 14 nM, about 16 nM, about 18 nM, about 20 nM, about 22 nM, about 24 nM, about 26 nM, about 28 nM or about 30 nM.

The CAR-antibody may recognize a synthetic (non-naturally-occurring) peptide. The CAR-antibody may comprise an antibody or antibody fragment that recognizes a FLAG® tag or a fragment thereof. The CAR-antibody may comprise an antibody or antibody fragment that recognizes a yeast transcription factor GCN4 or a fragment thereof. The CAR-antibody may comprise an anti-HTP antibody or a fragment thereof.

The transmembrane domain and/or the intracellular domain of the CAR may comprise at least a portion of a cytoplasmic signaling domain. The intracellular domain may comprise at least a portion of a signaling molecule selected from the group comprising CD3zeta, CD28, and 4-1BB. The intracellular domain may comprise an Fc receptor or a portion thereof. The Fc receptor or portion thereof may be CD16 or a portion thereof. The signaling molecule may comprise CD3zeta. The signaling molecule may comprise CD28. The signaling molecule may comprise 4-1BB. The intracellular domain may comprise at least a portion of CD3zeta. The intracellular domain may comprise at least a portion of CD28, The intracellular domain may comprise at least a portion of 4-1BB, The intracellular domain may comprise at least a portion of OX-40, The intracellular domain may comprise at least a portion of CD30, The intracellular domain may comprise at least a portion of CD40, The intracellular domain may comprise at least a portion of CD2. The intracellular domain may comprise at least a portion of CD27. The intracellular domain may comprise at least a portion of PD-1. The intracellular domain may comprise at least a portion of ICOS. The intracellular domain may comprise at least a portion of lymphocyte function-associated antigen-1 (LFA-1). The intracellular domain may comprise at least a portion of CD7. The intracellular domain may comprise at least a portion of LIGHT. The intracellular domain may comprise at least a portion of NKG2C. The intracellular domain may comprise at least a portion of B7-H3. The intracellular domain may comprise at least a portion of a cytoplasmic signaling domain from one or more signaling molecules. The intracellular domain may comprise at least a portion of two or more cytoplasmic signaling domains. The two or more cytoplasmic signaling domains may be from two or more different signaling molecules. The intracellular domain may comprise at least a portion of three or more cytoplasmic signaling domains. The intracellular domain may comprise at least a portion of four or more cytoplasmic signaling domains. The intracellular domain may comprise at least a portion of a ligand that binds to one or more signaling molecules. The intracellular domain may comprise at least a portion of a ligand that binds to CD83.

III. Chimeric Antigen Receptor Effector Cells (CAR-EC)

The methods, platforms and kits disclosed herein may comprise one or more chimeric antigen receptor effector cells (CAR-EC) or uses thereof. The chimeric antigen receptor effector cells disclosed herein express a chimeric antigen receptor. The chimeric antigen receptor (CAR) may be any CAR disclosed herein. Wherein the methods, platforms or kits comprise two or more effector cells, the two or more effector cells may be of the same cell type. The two or more effector cells may be of a different cell type. The two or more effector cells may be of the same cell lineage. The two or more effector cells may be of different cell lineages. The two or more effector cells may comprise two or more identical CARs. The two or more effector cells may comprise two or more different CARs. The two or more effector cells may comprise two or more similar CARs.

The effector cell may be a T cell. The effector cell may be a cell of a T cell lineage. The effector cell may be a mature T cell. The effector cell may be a precursor T cell. The effector cell may be a cytotoxic T cell. The effector cell may be a naive T cell. The effector cell may be a memory stem cell T cell ($T_{MSC}$). The effector cell may be a central memory T cell ($T_{CM}$). The effector cell may be an effector T cell (TE). The effector cell may be a CD4+ T cell. The T cell may be a CD8+ T cell. The effector cell may be a CD4+ and CD8+ cell. The effector cell may be an alpha-beta T cell. The effector cell may be a gamma-beta T cell. The effector cell may be a natural killer T cell. The effector cell may be a helper T cell.

While preferred embodiments of the present disclosure describe methods, kits and platforms comprising T cells, one skilled in the art may also understand that other cell types may be used in place of a T cell. The effector cell may be an effector cell that has an effect on a target or target cell when brought into proximity of the target or target cell. The effector cell may be a cell that has a cytotoxic effect on a target or target cell when brought into proximity of the target or target cell. The effector cell may be an immune cell. The effector cell may be selected from a B cell, a monocyte, a thrombocyte, a leukocyte, a neutrophil, an eosinophil, a basophil, or a lymphocyte. The effector cell may be a lymphocyte. The effector cell may be a macrophage. The effector cell may be a phagocytic cell. The effector cell may be an effector B cell. The effector cell may be a natural killer cell. The effector cell may isolated or derived from a subject suffering from a disease or condition. The effector cell may be a cell derived from a subject to be treated with a CAR-EC switch or CAR-EC platform disclosed herein.

The T cell may express a chimeric antigen receptor encoded by one or more polynucleotides based on or derived from SEQ ID NO: 1. The polynucleotide may be at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. The polynucleotide may be at least about 70% identical to one or more polynucleotides based on or derived from SEQ ID NO: 1. The polypeptide encoded by one or more polynucleotides may be based on or derived from SEQ ID NO: 1. The polypeptide may be encoded by a polynucleotide that is at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. The polynucleotide may be constitutively expressed. The polynucleotide may be conditionally expressed.

Disclosed herein are methods of producing a chimeric antigen receptor effector cell (CAR-EC), the methods comprising introducing one or more polynucleotides encoding a chimeric antigen receptor or a chimeric antigen receptor complex into an effector cell. The effector cell may be a T cell. Introducing one or more polynucleotides encoding a chimeric antigen receptor or a chimeric antigen receptor complex into an effector cell may comprise transfecting the effector cell with the one or more polynucleotides. Introducing one or more polynucleotides encoding a chimeric antigen receptor or a chimeric antigen receptor complex into an effector cell may comprise virally infecting the effector cell with one or more viruses comprising the one or more polynucleotides encoding a chimeric antigen receptor disclosed herein. The virus may be a lentivirus. The virus may be an adenovirus. The virus may be a retrovirus. The virus may be an adeno-associated virus. The virus may be a self-complementary adeno-associated virus (scAAV). The virus may be a modified human immunodeficiency (HIV) virus. The virus may be a modified herpes simplex virus (HSV) virus. Other methods of producing the CAR-EC may comprise a method of transferring one or more polynucleotides encoding a chimeric antigen receptor into a cell, wherein the methods comprise adding a transposon, a zinc finger nuclease, a TALEN or a CRISPR to the cell. The transposon may be a sleeping beauty transposon. The one or more polynucleotides may be based on or derived from SEQ ID NO: 1.

IV. CAR-EC Platform

Disclosed herein are chimeric antigen receptor effector cell (CAR-EC) platforms comprising a an effector cell, wherein the effector cell comprises a polynucleotide encoding a chimeric antigen receptor (CAR); and a chimeric antigen receptor effector cell (CAR-EC) switch, wherein the CAR-EC switch comprises a CAR binding peptidic antigen and a targeting polypeptide and wherein the CAR-EC switch binds a cell surface molecule on a target cell. The CAR-EC switch may be selected from any CAR-EC switches disclosed herein.

The CAR-EC platforms may comprise two or more CAR-EC switches. The CAR-EC platforms may comprise 3, 4, 5, 6, 7, 8, 9, 10, 11, 12, 13, 14, 15, 16, 17, 18, 19, 20 or more CAR-EC switches. The CAR-EC platforms may comprise may comprise more than 20, more than 25, more than 30, more than 35, more than 40, more than 45 or more than 50 CAR-EC switches. The two or more switches may be selected from one or more CAR-EC switches disclosed herein or a combination thereof.

The CAR-EC platforms disclosed herein may further comprise a first CAR-EC switch and a second CAR-EC switch, wherein the first CAR-EC switch comprises a first CAR-BP and a first targeting polypeptide and the second CAR-EC switch comprises a second CAR-BP and a second targeting polypeptide. The first CAR-BP and the second CAR-BP may be the same. The first CAR-BP and the second CAR-BP may be different. The first CAR-BP and the second CAR-BP may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous. The first targeting polypeptide and the second targeting polypeptide may be the same. The first targeting polypeptide and the second targeting polypeptide may be different. The first targeting polypeptide and the second targeting polypeptide may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous.

V. Kits, Vectors and Polynucleotides

Disclosed herein are kits comprising one or more CAR-EC switches disclosed herein. The kit may further comprise two or more CAR-EC switches. The kit may comprise three CAR-EC switches. The kit may comprise about 3, 4, 5, 6, 7, 8, 9, 10, 12, 15, 20, 24, 30, 35, 48, 50, 55, 60, 65, 70, 75, 80, 85, 90, 96, 100, 120, 150, 200, 300, 384, 400, 500, 600, 700, 800, 900 or 1000 CAR-EC switches. The kit may be employed for biological research. The kit may be used for diagnosing a disease or a condition. The kit may be used for treating a disease or condition. The CAR-EC switches of the kit may be used with CAR-EC cells disclosed herein or existing CAR T-cells clinically used or tested. The kit may further comprise one or more effector cells. The kit may further comprise one or more CAR-EC cells. The CAR-EC cell may be a T cell. The T cell may express one or more CARs. The kit may further comprise a polynucleotide encoding one or more CARs. The kit may further comprise a vector comprising a polynucleotide encoding one or more CARs. The CAR may be selected from any of the CARs disclosed herein. The kit may comprise one or more polynucleotide encoding a CAR-EC switch disclosed herein or a portion thereof (e.g. antibody, antibody fragment, peptide).

Further disclosed herein are and vectors and polynucleotides encoding CAR-EC switches or portions thereof, wherein the CAR-EC switch comprises a chimeric antigen receptor binding peptidic antigen and a targeting polypeptide, wherein the targeting peptide binds a cell surface molecule on a target cell. The polynucleotides may be DNA. The polynucleotides may be RNA. Unless otherwise specified, the terms "polynucleotide" and "vector," as used herein, are used interchangeably. The targeting polypeptide may be an antibody or antibody fragment. The vector may comprise a sequence encoding a heavy chain of the antibody or antibody fragment. The vectors may comprise a sequence encoding a light chain of the antibody or antibody fragment. The vectors may comprise the sequence encoding the light chain of the antibody or antibody fragment and the sequence encoding the heavy chain of the antibody or antibody fragment. The light chain and the heavy chain may be expressed from the same vector. The light chain and the heavy chain may be expressed from two separate vectors.

Disclosed herein are vectors and polynucleotides encoding chimeric antigen receptors, wherein the chimeric antigen receptors comprise an extracellular domain that binds to a peptide of a chimeric antigen receptor effector cell switch. The extracellular domain may comprise an antibody or antibody fragment. The antibody or antibody fragment may bind a peptidic antigen of a chimeric antigen receptor effector cell switch. The peptidic antigen may be a yeast peptide. The yeast peptide may be GCN4. f a or portions thereof may be encoded by one or more polynucleotides based on or derived from SEQ ID NO: 1. CARs or portions thereof may be encoded by a polynucleotide at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. CARs or portions thereof encoded by a polynucleotide may be at least about 70% identical to one or more polynucleotides based on or derived from SEQ ID NO: 1. Disclosed herein are vectors comprising one or more polynucleotides based on or derived from SEQ ID NO: 1.

Vectors comprising sequences encoding chimeric antigen receptors and/or chimeric antigen receptor effector cell switches and portions thereof, disclosed herein, may be selected from any commercially available expression vector. The expression vector may be a prokaryotic expression vector. The expression vector may be a eukaryotic expression vector. The expression vector may be a mammalian expression vector. The expression vector may be a viral expression vector. The expression vector may have a constitutive promoter for constitutive expression of the CAR and/or CAR-EC switch encoding sequences. The expression vector may have an inducible promoter for conditional expression of the CAR and/or CAR-EC switch encoding sequences.

VI. Therapeutic Use

Disclosed herein are methods, platforms and kits for treating a disease or condition in a subject in need thereof, the method comprising administering a chimeric antigen receptor effector cell (CAR-EC) switch to the subject, wherein the CAR-EC switch comprises: a CAR-binding peptidic antigen; and a targeting moiety. Disclosed herein are methods of treating a disease or condition in a subject in need thereof, the method comprising administering any one of the CAR-EC switches disclosed herein.

The methods may comprise administering a CAR-EC cell and one or more CAR-EC switches. The methods may comprise administering about 1, 2, 3, 4, 5, 6, 7, 8, 9, 10, 12, 15, 20, 24, 30, 35, 48, 50, 55, 60, 65, 70, 75, 80, 85, 90, 96, 100, 120, 150, 200, 300, 384, 400, 500, 600, 700, 800, 900, 1000 or more CAR-EC switches. The methods may comprise administering two or more CAR-EC switches. The two or more CAR-EC switches may comprise the same CAR-binding peptidic antigen. The two more CAR-EC switches may comprise the same cell targeting polypeptide. The two or more CAR-EC switches may comprise one or more different CAR-binding peptidic antigens. The two more CAR-EC switches may comprise one or more different cell targeting polypeptides. The methods may comprising a plurality of CAR-EC cells and one or more CAR-EC switches.

Disclosed herein are methods of treating a disease or condition in a subject in need thereof, the method comprising administering a chimeric antigen receptor effector cell (CAR-EC) switch to the subject, wherein the CAR-EC switch comprises: a chimeric antigen receptor binding peptidic antigen (CAR-BP); and a targeting moiety that binds an antigen on a target. The CAR-BP, by non-limiting example, may be selected from a FLAG® tag, a yeast transcription factor GCN4 and a hydrophilic target peptide (HTP). The targeting moiety, by non-limiting example may be selected from an anti-CD19 antibody, an anti-CD20 antibody, an anti-CD22 antibody, an anti-EGFR antibody, an anti-EGFRvIII antibody, an anti-Her2 antibody, an anti-CS1 antibody, an anti-BCMA antibody, an anti-CEA antibody, an anti-CLL-1 antibody and an anti-CD33 antibody.

The methods may comprise administering one or more chimeric antigen receptor effector cells. The methods may comprise administering one or more T cells. The one or more effector cells may be selected from T cell is selected from a naive T cell, a memory stem cell T cell, a central memory T cell, an effector memory T cell, a helper T cell, a CD4+ T cell, a CD8+ T cell, a CD8/CD4+ T cell, an $\alpha\beta$ T cell, a $\gamma\delta$ T cell, a cytotoxic T cell, a natural killer T cell, a natural killer cell, a macrophage.

The CAR-EC switch may have a therapeutic effect that is at least partially dependent on bringing an effector cell in proximity of a target cell. The therapeutic effect on the intended indication of the CAR-EC switch may be at least partially due to the CAR-EC switch recruiting an effector cell to the target cell. The therapeutic effect on the intended indication of the CAR-EC switch may be predominantly due to the CAR-EC switch recruiting an effector cell to the target cell. The therapeutic effect of the CAR-EC switch may be at least partially dependent on stimulating an immune response in the CAR-EC cell.

Administering the CAR-EC switch may not have any therapeutic effect without further administering an effector cell. The CAR-EC switch may not have a significant, desirable and/or intended therapeutic effect without further administering an effector cell. The CAR-EC switch may not have any therapeutic effect towards an intended indication of the CAR-EC platform without further administering an effector cell. A portion or component of the CAR-EC switch (e.g. CAR-BP or targeting moiety) may not have a therapeutic effect towards the intended indication of the CAR-EC switch without being conjugated to a second portion or component of the CAR-EC switch (e.g. CAR-BP or targeting moiety). The dose of a portion or component of the CAR-EC switch (e.g. CAR-BP or targeting moiety) when administered as part of the CAR-EC platform to provide a therapeutic effect may not have a therapeutic effect when the portion or component of the CAR-EC switch is administered alone at that dose. The portion or component of the CAR-EC switch may not be intended to have any therapeutic effect besides recruiting the T cell to the target cell. Administering the portion or component of the CAR-EC switch alone may have a therapeutic effect on the target cell, wherein the therapeutic effect is negligible relative to the therapeutic effect of administering the CAR-EC switch and the CAR-EC cell. Administering the portion or component of the CAR-EC switch may have a therapeutic effect on the target cell, wherein the therapeutic effect is less than the therapeutic effect of administering the CAR-EC switch and the CAR-EC cell.

Disclosed herein are uses of CAR-EC switches disclosed herein to treat a disease or condition in a subject in need thereof. Further disclosed herein are uses of CAR-EC switches disclosed herein in the manufacture of a medicament for the treatment of a disease.

Disclosed herein is use of a switch comprising a peptidic antigen that binds a CAR (CAR-BP) on an effector cell; and a targeting polypeptide that binds an antigen on a target to treat a disease or condition in a subject in need thereof. Further disclosed herein is use of a switch comprising a peptidic antigen (CAR-BP) that binds a CAR on an effector cell, wherein the CAR-BP; and a targeting polypeptide that binds an antigen on a target in the manufacture of a medicament for the treatment of a disease.

Disclosed herein is use of a CAR-EC switch comprising a CAR-BP, wherein the CAR-BP comprises a hydrophilic target peptide (HTP) or derivative thereof and a targeting polypeptide, wherein the targeting polypeptide comprises an anti-CD19 antibody or fragment thereof and an effector cell comprising a CAR, wherein the CAR comprises an anti-HTP antibody, wherein the anti-CD19 antibody or fragment thereof binds CD19 on a B cell to treat a multiple myeloma.

Disclosed herein is use of a CAR-EC switch comprising a CAR-BP, wherein the CAR-BP comprises a yeast transcription factor GCN4 or derivative thereof and a targeting polypeptide, wherein the targeting polypeptide comprises an anti-CD19 antibody or fragment thereof; and an effector cell comprising a CAR, wherein the CAR comprises an anti-GCN4 antibody, wherein the anti-CD19 antibody or fragment thereof binds CD19 on a lymphoblast, lymphocyte or B cell, to treat an acute lymphoblastic leukemia, a chronic lymphocytic leukemia or a B-cell lymphoma.

The disease or condition may be a cell proliferative disorder. The cell proliferative disorder may be selected from a solid tumor, a lymphoma, a leukemia and a liposarcoma. The cell proliferative disorder may be acute, chronic, recurrent, refractory, accelerated, in remission, stage I, stage II, stage III, stage IV, juvenile or adult. The cell proliferative disorder may be selected from myelogenous leukemia, lymphoblastic leukemia, myeloid leukemia, an acute myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia and hepatocellular carcinoma. The cell proliferative disorder may comprise a hematological malignancy. The hematological malignancy may comprise a B cell malignancy. The cell proliferative disorder may comprise a chronic lymphocytic leukemia. The cell proliferative disorder may comprise an acute lymphoblastic leukemia. The cell proliferative disorder may comprise a CD19-positive Burkitt's lymphoma.

The disease or condition may be a cancer, a pathogenic infection, autoimmune disease, inflammatory disease, or genetic disorder.

In some instances, the one or more diseases comprises a cancer. The cancer may comprise a recurrent and/or refractory cancer. Examples of cancers include, but are not limited to, sarcomas, carcinomas, lymphomas or leukemias.

The cancer may comprise a neuroendocrine cancer. The cancer may comprise a pancreatic cancer. The cancer may comprise an exocrine pancreatic cancer. The cancer may comprise a thyroid cancer. The thyroid cancer may comprise a medullary thyroid cancer. The cancer may comprise a prostate cancer.

The cancer may comprise an epithelial cancer. The cancer may comprise a breast cancer. The cancer may comprise an endometrial cancer. The cancer may comprise an ovarian cancer. The ovarian cancer may comprise a stromal ovarian cancer. The cancer may comprise a cervical cancer.

The cancer may comprise a skin cancer. The skin cancer may comprise a neo-angiogenic skin cancer. The skin cancer may comprise a melanoma.

The cancer may comprise a kidney cancer.

The cancer may comprise a lung cancer. The lung cancer may comprise a small cell lung cancer. The lung cancer may comprise a non-small cell lung cancer.

The cancer may comprise a colorectal cancer. The cancer may comprise a gastric cancer. The cancer may comprise a colon cancer.

The cancer may comprise a brain cancer. The brain cancer may comprise a brain tumor. The cancer may comprise a glioblastoma. The cancer may comprise an astrocytoma.

The cancer may comprise a blood cancer. The blood cancer may comprise a leukemia. The leukemia may comprise a myeloid leukemia. The cancer may comprise a lymphoma. The lymphoma may comprise a non-Hodgkin's lymphoma.

The cancer may comprise a sarcoma. The sarcoma may comprise an Ewing's sarcoma.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instances, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenströ m macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

The cancer may comprise a solid tumor. The cancer may comprise a sarcoma. The cancer may be selected from a group consisting of a bladder cancer, a breast cancer, a colon cancer, a rectal cancer, an endometrial cancer, a kidney cancer, a lung cancer, melanoma, a myeloma, a thyroid cancer, a pancreatic cancer, a glioma, a malignant glioma of the brain, a glioblastoma, an ovarian cancer, and a prostate cancer. The cancer may have non-uniform antigen expression. The cancer may have modulated antigen expression. The antigen may be a surface antigen. The cancer may not comprise a myeloma. The cancer may not comprise a melanoma. The cancer may not comprise a colon cancer. The cancer may be acute lymphoblastic leukemia (ALL). The cancer may be relapsed ALL. The cancer may be refractory ALL. The cancer may be relapsed, refractory ALL. The cancer may be chronic lymphocytic leukemia (CLL). The cancer may be relapsed CLL. The cancer may be refractory CLL. The cancer may be relapsed, refractory CLL.

The cancer may comprise a breast cancer. The breast cancer may be triple positive breast cancer (estrogen receptor, progesterone receptor and Her2 positive). The breast cancer may be triple negative breast cancer (estrogen receptor, progesterone receptor and Her2 negative). The breast cancer may be estrogen receptor positive. The breast cancer may be estrogen receptor negative. The breast cancer may be progesterone receptor positive. The breast cancer may be progesterone receptor negative. The breast cancer may comprise a Her2 negative breast cancer. The breast cancer may comprise a low-expressing Her2 breast cancer. The breast cancer may comprise a Her2 positive breast cancer. Cell lines expressing Her2 have been well-characterized for antigen density, reflecting clinical immunohistochemistry characterization which classifies malignancies as 0 (<20,000 Her2 antigens per cell), 1+(100,000 Her2 antigens per cell), 2+(500,000 Her2 antigens per cell), and 3+(>2,000,000 Her2 antigens per cell). The present invention provides for methods of treating breast cancers of these classifications. The breast cancer may comprise a breast cancer classified as Her2 0. The breast cancer may comprise a breast cancer classified as Her2 1+. The breast cancer may comprise a breast cancer classified as Her2 2+. The breast cancer may comprise a breast cancer classified as a Her2 3+.

The disease or condition may be a pathogenic infection. Pathogenic infections may be caused by one or more pathogens. In some instances, the pathogen is a bacterium, fungi, virus, or protozoan.

Exemplary pathogens include but are not limited to: *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. In some cases, the disease or condition caused by the pathogen is tuberculosis and the heterogeneous sample comprises foreign molecules derived from the bacterium *Mycobacterium tuberculosis* and molecules derived from the subject. In some instances, the disease or condition is caused by a bacterium is tuberculosis, pneumonia, which may be caused by bacteria such as *Streptococcus* and *Pseudomonas*, a foodborne illness, which may be caused by bacteria such as *Shigella, Campylobacter* and *Salmonella*, and an infection such as tetanus, typhoid fever, diphtheria, syphilis and leprosy. The disease or condition may be bacterial vaginosis, a disease of the vagina caused by an imbalance of naturally occurring bacterial flora. Alternatively, the disease or condition is a bacterial meningitis, a bacterial inflammation of the meninges (e.g., the protective membranes covering the brain and spinal cord). Other diseases or conditions caused by bacteria include, but are not limited to, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis,* and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (*e.g, I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

The disease or condition may be an autoimmune disease or autoimmune related disease. An autoimmune disorder may be a malfunction of the body's immune system that causes the body to attack its own tissues. Examples of autoimmune diseases and autoimmune related diseases include, but are not limited to, Addison's disease, alopecia areata, ankylosing spondylitis, antiphospholipid syndrome (APS), autoimmune aplastic anemia, autoimmune hemolytic anemia, autoimmune hepatitis, autoimmune myocarditis, Behcet's disease, celiac sprue, Crohn's disease, dermatomyositis, eosinophilic fasciitis, erythema nodosum, giant cell arteritis (temporal arteritis), Goodpasture's syndrome, Graves' disease, Hashimoto's disease, idiopathic thrombocytopenic purpura (ITP), IgA nephropathy, juvenile arthritis, diabetes, juvenile diabetes, Kawasaki syndrome, Lambert-Eaton syndrome, lupus (SLE), mixed connective tissue disease (MCTD), multiple sclerosis, myasthenia gravis, pemphigus, polyarteritis nodosa, type I, II, & III autoimmune polyglandular syndromes, polymyalgia rheumatica, polymyositis, psoriasis, psoriatic arthritis, Reiter's syndrome, relapsing polychondritis, rheumatoid arthritis, sarcoidosis, scleroderma, Sjogren's syndrome, sperm & testicular autoimmunity, stiff person syndrome, Takayasu's arteritis, temporal arteritis/giant cell arteritis, ulcerative colitis, uveitis, vasculitis, vitiligo, and Wegener's granulomatosis.

The disease or condition may be an inflammatory disease. Examples of inflammatory diseases include, but are not limited to, alveolitis, amyloidosis, angiitis, ankylosing spondylitis, avascular necrosis, Basedow's disease, Bell's palsy, bursitis, carpal tunnel syndrome, celiac disease, cholangitis, chondromalacia patella, chronic active hepatitis, chronic fatigue syndrome, Cogan's syndrome, congenital hip dysplasia, costochondritis, Crohn's Disease, cystic fibrosis, De Quervain's tendinitis, diabetes associated arthritis, diffuse idiopathic skeletal hyperostosis, discoid lupus, Ehlers-Danlos syndrome, familial mediterranean fever, fascitis, fibrositis/fibromyalgia, frozen shoulder, ganglion cysts, giant cell arteritis, gout, Graves' Disease, HIV-associated rheumatic disease syndromes, hyperparathyroid associated arthritis, infectious arthritis, inflammatory bowel syndrome/irritable bowel syndrome, juvenile rheumatoid arthritis, lyme disease, Marfan's Syndrome, Mikulicz's Disease, mixed connective tissue disease, multiple sclerosis, myofascial pain syndrome, osteoarthritis, osteomalacia, osteoporosis and corticosteroid-induced osteoporosis, Paget's Disease, palindromic rheumatism, Parkinson's Disease, Plummer's Disease, polymyalgia rheumatica, polymyositis, pseudogout, psoriatic arthritis, Raynaud's Phenomenon/Syndrome, Reiter's Syndrome, rheumatic fever, rheumatoid arthritis, sarcoidosis, sciatica (lumbar radiculopathy), scleroderma, scurvy, sickle cell arthritis, Sjogren's Syndrome, spinal stenosis, spondyloisthesis, Still's Disease, systemic lupus erythematosis, Takayasu's (Pulseless) Disease, Tendinitis, tennis elbow/golf elbow, thyroid associated arthritis, trigger finger, ulcerative colitis, Wegener's Granulomatosis, and Whipple's Disease.

Methods of treatment disclosed herein may comprise off-target activity as measured by cytokine levels. The method may reduce the off-target activity, as measured by cytokine levels, when compared to other CAR-EC therapies. The method may reduce the off-target activity as measured by interferon gamma levels. Other off-target activities that may be reduced include toxic lymphophenia, fatal cytolysis of solid tumor targets and chronic hypogammaglobulinemia for hematological targets. Methods of treatment and compositions disclosed herein may be used to treat a cancer comprising CD19-mediated B cell aplasia. The methods and compositions may minimize the CD19-mediated B cell aplasia. The method may avoid long-term B-cell aplasia.

The CAR-EC platforms, methods and compositions disclosed herein may be used to treat a heterogeneous tumor or a heterogeneous blood cell malignancy in a subject in need thereof. The "pan-B cell" marker CD20 is the most prevalently targeted antigen for B cell neoplasms and the FDA-approved antibody rituximab is a vital component in the treatment of many leukemias and lymphomas. However, resistance mechanisms related to modulation of CD20 antigen expression occurs in a significant number of patients. It is clear that targeting with either CD19 or CD20 antigen alone is insufficient for a curative therapy. The methods disclosed herein provide for construction and administration of two or more switches with different specificities (e.g. an anti-CD19 antibody CAR-EC switch and an anti-CD20 antibody CAR-EC switch). The methods disclosed herein provide for construction and administration of two or more switches with different specificities (e.g. an anti-CD19 antibody CAR-EC switch and an anti-CD22 antibody CAR-EC switch). This methodology may offer a significant advantage against the propensity for relapse in the clinic while avoiding persistent loss of B cells. A heterogeneous tumor or heterogeneous blood cell malignancy may also be treated with an anti-CD19 antibody CAR-EC switch and an anti-CD22 antibody CAR-EC switch. One or more CAR-EC switches may be administered sequentially or simultaneously.

The CAR-EC switch may be administered with one or more additional therapeutic agents. The one or more additional therapeutic agents may be selected from a group consisting of an immunotherapy, a chemotherapy and a steroid. The one or more additional therapeutic agents may be a chemotherapy drug. The chemotherapy drug may be an alkylating agent, an antimetabolite, an anthracycline, a topoisomerase inhibitor, a mitotic inhibitor, a corticosteroid or a differentiating agent. The chemotherapy drug may be selected from actinomycin-D, bleomycin, altretamine, bortezomib, busulfan, carboplatin, capecitabine, carmustine, chlorambucil, cisplatin, cladribine, clofarabine, cyclophosphamide, cytarabine, dacarbazine, daunorubicin, docetaxel, doxorubicin, epirubicin, etoposide, estramustine, floxuridine, fludarabine, fluorouracil, gemcitbine (Gemzar), hydroxyurea, idarubicin, ifosfamide, irinotecan (Camptosar), ixabepilone, L-asparaginase, lomustine, mechlorethamine, melphalan, 6-mercaptopurine, methotrexate, mitomycin-C, paclitaxel (Taxol), pemetrexed, pentostatin, streptozocin, temozolomide, teniposide, thioguanine, thiotepa, topotecan (Hycamtin), vincristine, vinblastine, vinorelbine, retinoids, tretinoin (ATRA or Atralin®), bexarotene (Targretin®) and arsenic trioxide (Arsenox®). The chemotherapy may be administered as a pill to swallow, as an injection into the muscle or fat tissue, intravenously, topically or directly into a body cavity.

The one or more additional therapeutic agents may comprise an angiogenesis inhibitor. The angiogenesis inhibitor may be selected from bevacizumab, itraconazole, carboxyamidotriazole, TNP-470, CM101, IFN alpha, IL-12, platelet factor 4, suramin, SU5416, thrombospondin, a VEGFR antagonist, an angiostatic steroid with heparin, CAR-ECilage-derived angiogenesis inhibitory factor, matrix metalloprotease inhibitors, angiostatin, endostatin, sorafenib, sunitinib, pazopanib, everolimus, 2-methoxyestradiol, tecogalan, tetrathiomolybdate, thalidomide, prolactin, $\alpha v \beta_3$ inhibitor, linomide, tasquinimod, soluble VEGFR-1, soluble NRP-1, angiopoietin 2, vasostatin, calreticulin, TIMP, CDAI, Meth-1, Meth-2, interferon-alpha, interferon-beta, interferon-gamma, CXCL10, IL-4, IL-12, IL-18, prothrombin, antithrombin III fragment, prolactin, VEGI, SPARC, osteopontin, maspin, canstatin, proliferin-related protein and restin.

The one or more additional therapeutic agents may comprise a hormone therapy. The hormone therapy may be selected from an anti-estrogen (e.g. fulvestrant (Faslodex®), tamoxifen, toremifene (Fareston®)); an aromatase inhibitor (e.g. anastrozole (Arimidex®), exemestane (Aromasin®) letrozole (Femara®); a progestin (e.g. megestrol acetate (Megace®); an estrogen; an anti-androgen (e.g. bicalutamide (Casode®), flutamide (Eulexin®), nilutamide (Nilandron®)); a gonadotropin-releasing hormone (GnRH) or luteinizing hormone-releasing hormone (LHRH) agonist or analog (e.g. leuprolide (Lupron®), goserelin (Zoladex®)).

The one or more additional therapeutic agents may comprise a steroid. The steroid may be a corticosteroid. The steroid may be cortisol or a derivative thereof. The steroid may be selected from prednisone, methylprednisolone (Solumedrol®) or dexamethasone.

The CAR-EC switch may be administered with one or more additional therapies. The one or more additional therapies may comprise laser therapy. The one or more additional therapies may comprise radiation therapy. The one or more additional therapies may comprise surgery.

Disclosed herein are platforms, kits and methods for treating a disease or condition in a subject. The subject may be a healthy subject. The subject may be suffering from a disease or condition. The subject may be suffering from more than one disease or condition. The subject may be suffering from chronic lymphocytic leukemia. The subject may be suffering from acute lymphoblastic leukemia. The subject may be an animal. The subject may be a mammal. The mammal may be a human, a chimpanzee, a gorilla, a monkey, a bovine, a horse, a donkey, a mule, a dog, a cat, a pig, a rabbit, a goat, a sheep, a rat, a hamster, a guinea pig or a mouse. The subject may be a bird or a chicken. The subject may be a human. The subject may be a child. The child may be suffering from acute lymphoblastic leukemia. The subject may be less than 6 months old. The subject may be about 1 year old, about 2 years old, about 3 years old, about 4 years old, about 5 years old, about 6 years old, about 7 years old, about 8 years old, about 9 years old, about 10 years old, about 11 years old, about 12 years old, about 13 years old, about 14 years old, about 15 years old, about 18 years old, about 20 years old, about 25 years old, about 30 years old, about 35 years old, about 40 years old, about 45 years old, about 50 years old, about 55 years old, about 60 years old, about 65 years old, about 70 years old, about 75 years old, about 80 years old, about 85 years old, about 90 years old, about 95 years old, about 100 years old or about 105 years old.

VII. Method of Clearing Effector Cells

Further disclosed herein are methods of clearing CAR-EC cells in a subject, comprising administering a CAR-EC off switch. The CAR-EC off switch may comprise an antibody or antibody fragment that targets a cell surface marker on the effector cell. The CAR-EC off switch may comprise a peptide that is bound by the CAR of the CAR-EC. The CAR-EC off switch may comprise a CAR-BP that is bound by the CAR of the CAR-EC.

The antibody, antibody fragment or peptide of the CAR-EC off switch may be conjugated to a drug or a toxin. The drug or toxin may be selected from maytasine (e.g. DM1, DM4), monomethylauristatin E, monomethylauristatin F, Ki-4.dgA, dolastatin 10, calicheamicin, SN-38, duocarmycin, irinotecan, ricin, saporin, gelonin, poke weed antiviral protein, *pseudomonas aeruginosa* exotoxin A or diphtheria toxin. The toxin may comprise a poison, a bacterial toxin (e.g. bacterial toxins causing tetanus, diphtheria), a plant toxin or animal toxin. The toxin may be a snake venom. The toxin may comprise vinblastine. The toxin may comprise auristatin. The toxin may be contained in a liposome membrane-coated vesicle. Wherein the toxin is contained in a liposome membrane-coated vesicle, the antibody is attached to the vesicle.

The cell surface marker may be a viral protein or fragment thereof. Alternatively or additionally, the effector cell expresses a viral protein or fragment thereof that is not a cell surface marker. The effector cell expressing a viral protein or fragment thereof may be targeted with a drug. Wherein the effector cell comprises a viral protein or fragment thereof, the drug may be selected from a group comprising abacavir, acyclovir, acyclovir, adefovir, amantadine, amprenavir, ampligen, arbidol, atazanavir, atripla, balavir, boceprevirertet, cidofovir, combivir, darunavir, delavirdine, didanosine, docosanol, edoxudine, efavirenz, emtricitabine, enfuvirtide, entecavir, an entry inhibitor, famciclovir, a fixed dose combination antiretroviral drug, fomivirsen, fosamprenavir, foscarnet, fosfonet, a fusion inhibitor, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, methisazone, nelfinavir, nevirapine, nexavir, nucleoside analogue, oseltamivir, peginterferon alfa-2a, penciclovir, peramivir, pleconaril, podophyllotoxin, protease inhibiro, raltegravir, a reverse transcriptase inhibitor, ribavirin, rimantadine, ritonavir, pyramidine, saquinavir, sofosbuvir, stavudine, a synergistic enhancer retroviral durg, tea tree oil, telaprevir, tenofovir, tenofovir disoproxil, tipranavir, trifluridine, trizivir, tromantadine, truvada, valaciclovir, vicriviroc, vidarabine, viramidine, zacitabine, zanamivir or zidovudine. The drug may be ganciclovir. The drug may be acyclovir.

VIII. Pharmaceutical Compositions

Disclosed herein is a pharmaceutical composition comprising one or more of the CAR-EC switches disclosed herein. The compositions may further comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HC1. Acetate buffer may be about pH 4-5.5, and Tris buffer may be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, *acacia*, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions may comprise the formulation of CAR-EC switches, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then may be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722. Suitable materials for this purpose include polylactides (see, e.g., U.S. Pat. No. 3,773,919), polymers of poly-(a-hydroxycarboxylic acids), such as poly-D-(-)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(-)-3-hydroxybutyric acid. Other biodegradable polymers include poly(lactones), poly(acetals), poly(orthoesters), and poly(orthocarbonates). Sustained-release compositions also may include liposomes, which may be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This may be determined by routine screening in animal models of the target disorder or, if such models are unavailable, in normal animals. Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids may be cleared quickly within the human body. Moreover, the degradability of this polymer may be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141).

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which a CAR-EC switch disclosed herein has been absorbed or encapsulated. Where an implantation device is used, the device may be implanted into any suitable tissue or organ, and delivery of a CAR-EC switch, nucleic acid, or vector disclosed herein may be directly through the device via bolus, or via continuous administration, or via catheter using continuous infusion.

A pharmaceutical composition comprising a CAR-EC switch disclosed herein may be formulated for inhalation, such as for example, as a dry powder Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 μm to 5 μm; however, larger particles may be used, for example, if each particle is fairly porous.

Certain formulations containing CAR-EC switches disclosed herein may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also may be employed.

Another preparation may involve an effective quantity of a CAR-EC switch disclosed herein in a mixture with nontoxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or *acacia*; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

IX. CAR-EC Switch Production Methods

Disclosed herein are methods of producing CAR-EC switches comprising expressing one or more polypeptides from one or more vectors comprising one or more polynucleotide having one or more sequences that encode a chimeric antigen receptor-effector cell switch or a portion thereof, wherein the chimeric antigen receptor-effector cell switch comprises a peptidic antigen (CAR-BP) and a targeting polypeptide. The targeting moiety may comprise a targeting polypeptide. In general, the methods comprise fusing or grafting a polynucleotide encoding the CAR-BP to a polynucleotide encoding the targeting polypeptide. Fusing or grafting may be carried out by any standard cloning method known to one skilled in the art. Fusing or grafting the polynucleotides encoding the CAR-BP and targeting polypeptide may comprise enzymatic digestion of the polynucleotides, ligation of the polynucleotides and/or amplification of the polynucleotides.

The peptidic antigen may be fused to an N terminus of the targeting polypeptide. The peptidic antigen may be fused to a C terminus of the targeting polypeptide. The peptidic antigen may be grafted within the targeting polypeptide. The targeting polypeptide may comprise a targeting antibody or antibody fragment. The peptidic antigen may be fused to an N terminus of the targeting antibody or antibody fragment. The peptidic antigen may be fused to a C terminus of the targeting antibody or antibody fragment.

As used herein, the term "fused" may refer to adjoining a terminus of the CAR-BP with a terminus of the targeting polypeptide. The CAR-BP may be fused to the terminus of the targeting polypeptide without replacing or removing any amino acids of the targeting polypeptide. Fusing the CAR-BP to the terminus of the targeting polypeptide may comprise removing or replacing amino acids at the terminus of the targeting polypeptide. Removing or replacing amino acids at the terminus of the targeting polypeptide may comprise removing or replacing about 1 to about 20 amino acids at the terminus of the targeting polypeptide. The CAR-BP may be fused to the terminus of the targeting polypeptide via a linker. The linker may be fused to the CAR-BP to produce a CAR-BP-linker intermediate. The linker may be fused to a CAR-BP N terminus to produce the CAR-BP-linker intermediate. The linker may be fused to a CAR-BP C terminus to produce the CAR-BP-linker intermediate. The CAR-BP-linker intermediate may be fused to the targeting polypeptide. The CAR-BP-linker intermediate may be fused to the N terminus of the targeting polypeptide. The CAR-BP-linker intermediate may be fused to the C terminus of the targeting polypeptide. A first CAR-BP linker intermediate may be fused to the N terminus of the targeting polypeptide and a second CAR-BP linker intermediate may be fused to the C terminus of the targeting polypeptide. The CAR-BP of the first CAR-BP linker intermediate may be the same or similar to the CAR-BP of the second CAR-BP linker intermediate. The CAR-BP of the first CAR-BP linker intermediate may be different from the CAR-BP of the second CAR-BP linker intermediate.

As used herein, the term "grafted" may refer to inserting a CAR-BP within a targeting polypeptide (e.g. between two amino acids of the targeting polypeptide). The CAR-BP may be grafted within the targeting polypeptide without replacing or removing any amino acids of the targeting polypeptide. Grafting the CAR-BP within the targeting polypeptide may comprise removing or replacing amino acids within the targeting polypeptide. Removing or replacing amino acids within the targeting polypeptide may comprise removing or replacing about 1 to about 20 amino acids within the targeting polypeptide. The CAR-BP may be grafted within the targeting polypeptide via one linker. The CAR-BP may be grafted within the targeting polypeptide via two linkers. The linker may be fused to the CAR-BP N terminus to produce a CAR-BP-linker intermediate. The linker may be fused to the CAR-BP C terminus to produce a CAR-BP-linker intermediate. A first linker may be fused to the CAR-BP N terminus and a second linker may be fused to the CAR-BP C terminus to produce a CAR-BP-linker intermediate. The CAR-BP linker intermediate may be grafted with in the targeting polypeptide. A first CAR-BP linker intermediate may be grafted within the targeting polypeptide and a second CAR-BP linker intermediate may be grafted within the targeting polypeptide. The first CAR-BP linker intermediate may be grafted within a first domain of the targeting polypeptide and a second CAR-BP linker intermediate may be grafted within a second domain of the targeting polypeptide. The first domain of the targeting polypeptide may be the same as the second domain of the targeting polypeptide. The first domain of the targeting polypeptide may be different from the second domain of the targeting polypeptide. The CAR-BP of the first CAR-BP linker intermediate may be the same or similar to the CAR-BP of the second CAR-BP linker intermediate. The CAR-BP of the first CAR-BP linker intermediate may be different from the CAR-BP of the second CAR-BP linker intermediate. Unless otherwise specified, the terms "graft" and "insert", as used herein, are used interchangeably.

The targeting moiety may comprise an antibody or antibody fragment. The antibody or antibody fragment may comprise a heavy chain and a light chain or fragments thereof. The methods may comprise expressing a heavy chain wherein the peptidic antigen is fused to a terminus of the heavy chain. The methods may comprise expressing a heavy chain wherein the peptidic antigen is grafted within the heavy chain. The methods may comprise expressing a light chain wherein the peptidic antigen is fused to a terminus of the light chain. The methods may comprise expressing a light chain wherein the peptidic antigen is grafted within the light chain.

The methods may further comprise cloning one or more polynucleotides encoding the targeting polypeptide and/or the peptidic antigen into an expression vector. The methods may further comprise ligation of the one or more polynucleotides encoding the targeting polypeptide and/or peptidic antigen into an expression vector. The expression vector may be a prokaryotic expression vector. The expression vector may be a eukaryotic expression vector. The expression vector may be a mammalian expression vector. The expression vector may be a viral expression vector. The methods may further comprise validating the cloning of the one or more polynucleotides encoding the targeting polypeptide and/or peptidic antigen into the expression vector comprising sequencing the expression vector, running gel electrophoresis of the vector and/or viewing the targeting polypeptide and/or peptidic antigen on an SDS page gel.

The methods may further comprise amplifying a polynucleotide encoding the targeting polypeptide and/or peptidic antigen and cloning the targeting polypeptide and/or peptidic antigen into the expression vector. Amplifying the polynucleotide encoding the targeting polypeptide and/or the peptidic antigen may comprise synthesizing oligonucleotides at least partially complementary to the gene. The oligonucleotides may be sufficiently complementary to the gene to anneal to the polynucleotide. The oligonucleotides may comprise linker sequences. The linker sequences may be selected from SEQ ID NOs: 40-44.

The methods may further comprise transfecting or infecting a cell with the expression vector. The methods may further comprise expressing the targeting polypeptide and/or peptidic antigen in the cell. The methods may further comprise expressing the targeting polypeptide and/or peptidic antigen in a cell free system. The methods may further comprise producing a virus comprising the expression vector. The methods may further comprise propagating the virus. The methods may further comprise infecting a cell with the virus comprising the expression vector. The methods may further comprise propagating the cell.

Disclosed herein are methods of grafting the antibody or antibody fragment, the peptidic antigen or the targeting peptide to produce a CAR-EC switch. The method may comprise grafting the CAR-BP to the antibody or antibody fragment. The method may comprise grafting the CAR-BP to an N terminus, C terminus or internal site of the antibody or antibody fragment. The CAR-BP may be grafted to a CL domain of the antibody or antibody fragment. The CAR-BP may be grafted to a loop of the CL domain of the antibody or antibody fragment. The method may comprise grafting the antibody or antibody fragment to the CAR-BP. The method may comprise grafting the antibody or antibody fragment to an N terminus, C terminus or internal site of the CAR-BP. The method may comprise grafting the CAR-BP to the targeting peptide. The method may comprise grafting the CAR-BP to an N terminus, C terminus or internal site of the targeting peptide. The method may comprise grafting the targeting peptide to the CAR-BP. The method may comprise grafting the targeting peptide to an N terminus, C terminus or internal site of the CAR-BP.

The CAR-BP, targeting peptide, antibody or antibody fragment may comprise one or more linkers, wherein the linker is located at the N terminus and/or C terminus of the CAR-BP, targeting peptide, antibody or antibody fragment. The method may comprise grafting the antibody or antibody fragment, the CAR-BP or the targeting peptide through the linker. The linker may comprise (GSSSS)$_n$ (SEQ ID NO: 47).

Grafting may comprise producing a CAR-EC switch encoding nucleic acid. Producing the CAR-EC switch encoding nucleic acid may comprise one or more polymerase chain reactions. Producing the CAR-EC switch encoding nucleic acid may comprise one or more nucleic acid enzymatic digestions. The enzymatic digestion may be site specific. Producing the CAR-EC switch encoding nucleic acid may comprise one or more ligations. The methods of producing the CAR-EC switch may comprise incorporating the CAR-EC switch encoding nucleic acid into a CAR-EC switch vector. The vector may be an expression vector. The expression vector may comprise a constitutive promoter, an inducible promoter and/or a conditional promoter. The CAR-EC switch encoding nucleic acid or CAR-EC switch vector may be expressed in a cell and the resulting CAR-EC switch isolated and purified. The cell may be a prokaryotic cell. The cell may be an *E. coli*. The cell may be a eukaryotic cell. The cell may be a mammalian cell. The CAR-EC switch encoding nucleic acid or CAR-EC switch vector may be expressed in a cell-free system. Alternatively or additionally the CAR-EC switch may be synthesized from free amino acids.

Purification of CAR-EC Switches and Portions Thereof

Disclosed herein are methods of purifying CAR-EC switches disclosed herein, comprising separating the CAR-EC switches disclosed herein from components of a CAR-EC switch production system (e.g. cellular debris, free amino acids). Purifying the CAR-EC switch may comprise use of one or more concentrator columns, electrophoresis, filtration, centrifugation, chromatography or a combination thereof. Chromatography may comprise size-exclusion chromatography. Additional chromatography methods include, but are not limited to, hydrophobic interaction chromatography, ion exchange chromatography, affinity chromatography, metal binding, immunoaffinity chromatography, and high performance liquid chromatography or high pressure liquid chromatography. Electrophoresis may comprise denaturing electrophoresis or non-denaturing electrophoresis.

The CAR-EC switches may comprise one or more peptide tags. The methods of purifying CAR-EC switches may comprise binding one or more peptide tags of the CAR-EC switches to a capturing agent. The capturing agent may be selected from an antibody, a column, a bead and a combination thereof. The one or more tags may be cleaved by one or more proteases. Examples of tags include, but are not limited to, polyhistidine, FLAG® tag, HA, c-myc, V5, chitin binding protein (CBP), maltose binding protein (MBP), and glutathione-S-transferase (GST). The peptide tag may be the CAR-BP. The peptide tag may be HTP. The peptide tag may be yeast transcription factor GCN4.

The methods may further comprise lyophilization or ultracentrifugation of the CAR-BPs, targeting polypeptides and/or the CAR-EC switches.

The purity of the CAR-BPs, targeting polypeptides and/or the CAR-EC switches may be equal to or greater than 50%, 55%, 60%, 65%, 70%, 75%, 80%, 85%, 90%, 91%, 92%, 93%, 94%, 95%, 96%, 97%, 98%, 99% or more. The purity of the CAR-BPs, targeting polypeptides and/or the CAR-EC switches may be equal to or greater than 85%. The purity of the CAR-BPs, targeting polypeptides and/or the CAR-EC switches may be equal to or greater than 90%. The purity of the CAR-BPs, targeting polypeptides and/or the CAR-EC switches may be equal to or greater than 95%. The purity of the CAR-BPs, targeting polypeptides and/or the CAR-EC switches may be equal to or greater than 97%.

The methods of producing CAR-EC switches disclosed herein may comprise producing CAR-EC switches that are structurally homogeneous. The method of producing the CAR-EC switch from a polynucleotide may result in one or more CAR-EC switches that have the same or similar form, features, binding affinities (e.g. for the CAR or the target), geometry and/or size. The homogeneity of the CAR-EC switches may be equal to or greater than 50%, 55%, 60%, 65%, 70%, 75%, 80%, 85%, 90%, 91%, 92%, 93%, 94%, 95%, 96%, 97%, 98%, 99% or more. The homogeneity of the CAR-EC switches may be equal to or greater than 85%. The homogeneity CAR-EC switches may be equal to or greater than 90%. The homogeneity of the CAR-EC switches may be equal to or greater than 95%. The homogeneity of the CAR-EC switches may be equal to or greater than 97%. The homogeneity may be a structural homogeneity. The homogeneity may be a structural homogeneity prior to administering the cell to a subject. The homogeneity may be a structural homogeneity prior to modifications to the CAR-EC switch by cellular activities (methylation, acetylation, glycosylation, etc.). These high percentages of homogeneity may provide a more predictable effect of the CAR-EC switch. These high percentages of homogeneity may provide for less off-target effects of the CAR-EC switch, when combined with a CAR-EC to treat a condition in a subject.

EXAMPLES

The following illustrative examples are representative of embodiments of the software applications, systems, and methods described herein and are not meant to be limiting in any way.

Example 1

Production and Evaluation of a Switchable CAR-T Platform

The solubility, stability, affinity, and potential for cross reactive epitopes in the human proteome of developed antibodies were considered in choosing a CAR-EC switch peptidic antigen. Based on these criteria, a linear amino acid epitope from the yeast transcription factor GCN4 (7P14P) was chosen. Single chain antibodies with affinities varying from 2.6 nM to 5.2 pM enable optimization of the CAR-EC through binding kinetics. Additionally, these antibodies are among the highest affinity anti-peptide single chain antibodies for linear epitopes. The dissociation constant (Kd) for the chosen GCN4 epitope (7P14P) having a sequence of NYHLENEVARLKKL (SEQ ID NO. 3) and GCN4 binding scFv (52SR4) is 5.2 pM.

A small hydrophilic target peptide (HTP), based on the commonly used FLAG® tag, was developed. FLAG® has low antigenicity, is highly soluble, and has been fused to numerous proteins with little impact on protein folding or stability. In modifying FLAG to HTP, a proline residue was incorporated after the terminal lysine in an effort to increase proteolytic stability. Antibodies to this epitope are developed by traditional mouse immunization and subsequent humanization or by phage panning of a human library. Binding kinetics of evolved scFv's are fully characterized and peptide-CAR-ECs are created and tested for off-target specificity as described.

Evaluation of a Switchable CAR-T Platform in a Xenograft Model

To evaluate efficacy, mouse xenograft models are used to compare these switchable platforms to previously developed by CAR-T switch platforms. Towards this end, RS4; 11, NALM-6, Raji or other CD19 positive cell lines are used to establish tumor models in non-obese diabetic-severe combined immunodeficiency (NOD-SCID-$\gamma^{-/-}$, NSG) mice. CAR-Ts are delivered by intravenous administration. Dose-range finding is carried out for the peptide anti-CD19 switch, and is compared to a wild type CD19 Fab control. Efficacy is judged based on tumor burden and overall survival. Mice are monitored with weekly blood draws to monitor proliferation of CAR-ECs in peripheral blood. Detailed immunophenotypic characterization of CAR-ECs focus on effector, memory, senescent (terminally differentiated), or anergized phenotypes are defined according to standard phenotypic parameters using multi-channel flow cytometry.

Efficacy of the Fab, and IgG based switches are delivered at appropriate dosages per observed PK data and compared. IgG is most efficacious in this model for its long residence time in vivo. Further exploration on this idea is carried out in the syngeneic model.

Primary patient-derived ALL or CLL samples are obtained and for generating xenograft models in NSG mice. Primary samples are characterized for CD19 expression by flow cytometry. Leukemia is established in mice for 2-3 weeks prior to administration of therapy. Efficacy versus CAR-T-19 is judged by monitoring CD19$^+$ ALL blast counts in peripheral blood. In the event that leukemia is not controlled or eliminated, proliferated blasts are immunophenotyped (specifically looking for loss of CD19 antigen expression, vida infra for further study). Persistence of CAR-ECs is also monitored (although the latter is not expected to differ substantially from RS4; 11-based xenografts).

Evaluation of a Switchable CAR-T Platform in a Syngeneic Model

Although the xenograft models in immunodeficient mice allow measurement of the efficacy of the switchable platform, this model is not optimal to assess a method for alleviating the long-term lymphopenia associated with CAR-T-19 therapy. Switchable CAR-ECs are tested for the ability to reverse B cell aplasia in an immunocompetent B cell lymphoma mouse model. To create a murine surrogate CAR-T, the engineered peptide-based chimeric receptor is cloned to a Moloney murine leukemia-based retroviral vector for transduction into murine splenocytes. The murine-derived signaling domains CD28 and CD3z are used. The anti-human CD19 antibody does not cross-react with mouse CD19; therefore, the rat anti-mouse CD19 hybridoma 1D3 is obtained (from ATCC) and variable regions sequenced. This sequence is cloned into an expression vector for peptide fusion to create the switch and is cloned into a chimeric antigen receptor to create a CAR-T-19 mouse surrogate.

After optimization of transduction and assessment of efficacy in vitro, the Myc5-CD19 cell line is used to establish B cell lymphoma in wild type C57BL/6 mice. CAR-ECs and switches are administered with dosing schedules based on xenograft studies and in vitro assays with surrogate system. Of particular interest in this model is to compare Fab, and IgG based switches on the rate of Myc5-CD19 disappearance and B cell ablation. As with xenografts studies, CAR-T proliferation is monitored and immunophenotypic characterization is carried out ex vivo. After eradication of lymphoma cells, switch administration is halted and the reproliferation of B cells in peripheral blood is monitored. Both the surrogate CAR-T-19 and the surrogate switchable CAR-T are expected to enable long-term remission, but only the switchable platform enables repopulation of B cells. CAR-T infiltration to major organs is monitored via histology on predefined cohorts and cellular analysis is carried out post-therapy. Long-term persistence of CAR-ECs in the absence of stimulation is followed.

Evaluation of a Switchable CAR-T Platform in a Heterogeneous Cancer Model

A first switch containing an anti-CD19 targeting antibody and a second switch containing the anti-CD20 targeting antibody rituximab are used sequentially or simultaneously to target different antigens in the same patient using a single adoptively transferred CAR-T in an effort to combat ALL relapse attributed to a CD19 escape variant during CAR-T-19 therapy.

An anti-CD20 switch is created in analogous fashion to the anti-CD19 switch using the optimal characteristics determined in Example 3. A CAR-T-20 based on rituximab is constructed for comparison. Efficacy is tested in vitro against CD20-positive IM-9 and Daudi cells lines. To create a heterogeneous B-cell lymphoblast, the chronic myelogenous leukemia-derived K562 cell line (which is negative for CD20 and CD19) is stably transduced with the CD19 antigen using a lentiviral vector. Single cell clones are obtained via flow-sorting to obtain a population with homogenous CD19 expression. This cell line is then be transduced with CD20 and sorted by high (CD20$^{hi}$) or low (CD20$^{low}$) level of antigen expression. The activation and cytotoxicity of the switchable CAR-T on mixtures of CD19$^+$ CD20$^-$ and CD19$^{+CD}$20$^{hi}$ or CD19$^+$CD20$^{low}$ are assessed in vitro using the CD19 and CD20 switches (simultaneous or sequential administration). The method provides an opportunity to study the lowest percentage of CD20$^{hi}$ or CD20$^{low}$ cells in a population that are necessary to stimulate the CAR-T with the rituximab switch. This may be more physiologically relevant than a homogeneous population. This system is then tested in a xenograft mouse model. A mixture of CD19$^+$CD20$^-$ and CD19$^+$CD20$^+$ are used to establish the xenograft. Alternatively, primary patient derived ALL samples are used for this experiment if found to be heterogeneous for CD19 or CD20 expression in our initial xenograft study. Switchable CAR-ECs with the anti-CD20 switch are administered to eliminate the CD19$^+$CD20$^+$ population and allow outgrowth of CD19$^+$CD20$^-$ cells. To demonstrate the feasibility of retargeting the same CAR-T, the anti-CD19 switch is subsequently dosed and growth of remaining xenograft monitored. Tumors are evaluated for antigen expression in cohorts of sacrificed mice or in primary blasts. Simultaneous targeting is also assessed. Treatment is compared with CAR-T-19, CAR-T-20, or both simultaneously.

Example 2

CAR Construction

The CARs were constructed as follows:

LV-EF1a-GCN4-BBZ was designed to target the 7P14P epitope of the yeast transcription factor GCN4 (sequence RMKQLEPKVEELLPKN<u>YHLENEVARLKKL</u>VGER (SEQ ID NO. 2) where the underlined amino acids have been shown to bind to the c11L32Ser scFv in the 1P4B crystal structure from PDB. The scFv was constructed from the 52SR4 (high affinity mutant with similar sequence to c11L32Ser) antibody scFv from reference: Zahnd, C., Spinelli, S., Luginbuhl, B., Amstutz, P., Cambillau, C., and Pluckthun, A. (2004) Directed in vitro evolution and crystallographic analysis of a peptide-binding single chain antibody fragment (scFv) with low picomolar affinity, *The Journal of Biological Chemistry* 279, 18870-18877.

Example 3

Cloning, Expression and Purification of Anti-CD19-Fab-GCN4$_{HC1}$

Cloning: Mammalian expression vector of CD19 Fab heavy chain was generated by ligation of amplified CD19 Fab heavy chain (VH and CH1) to pFuse-hIgG1-Fc backbone vector (InvivoGen, CA) without Fc fragment. A gene encoding antibody CD19 light chain was amplified and cloned into the pFuse vector without hIgG1 Fc fragment. A gene encoding GCN4 (NYHLENEVARLKKL=SEQ ID NO: 3) with was synthesized as oligonucleotides. Subsequently, anti-CD1-Fab-GCN4$_{HC1}$ fusion proteins were created by grafting GCN4 into the mature heavy chain of the CD19 Fab following S135 of the CD19 Fab heavy chain. The resulting mammalian expression vectors were confirmed by DNA sequencing.

Expression and Purification: anti-CD19-Fab-GCN4$_{HC1}$ was expressed through transient transfection of FreeStyle HEK 293 cells with expression vectors of CD19-Fab light chain and GCN4-CD19-HC1, according to the manufacturer's protocol. Briefly, 28 mL FreeStyle HEK 293 cells containing 3×107 cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% CO2 environment at 37° C. Culture medium containing secreted proteins was harvested at 48 and 96 hours after transfection. The anti-CD1-Fab-GCN4$_{HC1}$ was purified by Protein G chromatography (Thermo Fisher Scientific, IL). Purified proteins were analyzed by SDS-PAGE gels. FIGS. 5A and 5B show SDS gel images of anti-CD1-Fab-GCN4$_{HC1}$ (Lane 7) in non-reducing and reducing (with 50 mM DTT) conditions, respectively.

Example 4

Cloning, Expression and Purification of Anti-CD19-IgG-GCN4$_{HC1}$

Cloning: Mammalian expression vector of CD19 IgG heavy chain was generated by in-frame ligation of amplified CD19 Fab heavy chain (VH and CH1) to pFuse-hIgG1-Fc backbone vector (InvivoGen, CA). A gene encoding antibody CD19 light chain was amplified and cloned into the pFuse vector without hIgG1 Fc fragment. A gene encoding GCN4 (NYHLENEVARLKKL=SEQ ID NO: 3) was synthesized as oligonucleotides. Subsequently, anti-CD19-IgG-GCN4$_{HC1}$ fusion proteins were created by inserting GCN4 following S135 of the mature heavy chain of the CD19 IgG. The resulting mammalian expression vectors were confirmed by DNA sequencing.

Expression and Purification: anti-CD19-IgG-GCN4$_{HC1}$ was expressed through transient transfection of FreeStyle HEK 293 cells with expression vectors of CD19-IgG light chain and GCN4-CD19 heavy chain, according to the manufacturer's protocol. Briefly, 28 mL FreeStyle HEK 293 cells containing 3×107 cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% CO2 environment at 37° C. Culture medium containing secreted proteins was harvested at 48 and 96 hours after transfection. GCN4-CD19 heavy chain was purified by Protein G chromatography (Thermo Fisher Scientific, IL). Purified proteins were analyzed by SDS-PAGE gels. FIGS. 5A & 5B show SDS gel images of anti-CD19-IgG-GCN4$_{HC1}$ (Lane 3) in non-reducing and reducing (with 50 mM DTT) conditions, respectively.

Example 5

Cloning, Expression and Purification of Anti-CD19-Fab-GCN4$_{C\text{-}term}$

Cloning: Mammalian expression vector of CD19 Fab heavy chain was generated by ligation of amplified CD19 Fab heavy chain (VH and CH1) to pFuse-hIgG1-Fc backbone vector (InvivoGen, CA) without Fc fragment. A gene encoding antibody CD19 light chain was amplified and cloned into the pFuse vector without hIgG1 Fc fragment. A gene encoding GCN4 (NYHLENEVARLKKL=SEQ ID NO: 3) with GGGGS (SEQ ID NO: 48) linker at N-terminal end of GCN4 with was synthesized as oligonucleotides. Subsequently, anti-CD19-Fab-GCN4$_{C\text{-}term}$ term fusion proteins were created by fusing the linker-GCN4 to the C terminus of the Fab heavy chain at C223. The resulting mammalian expression vectors were confirmed by DNA sequencing.

Expression and Purification: anti-CD19-Fab-GCN4$_{C\text{-}term}$ was expressed through transient transfection of FreeStyle HEK 293 cells with expression vectors of CD19-Fab light chain and anti-CD19-Fab-GCN4$_{C\text{-}term}$, according to the manufacturer's protocol. Briefly, 28 mL FreeStyle HEK 293 cells containing 3×107 cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% CO2 environment at 37° C. Culture medium containing secreted proteins was harvested at 48 and 96 hours after transfection. anti-CD19-Fab-GCN4$_{C\text{-}term}$ was purified by Protein G chromatography (Thermo Fisher Scientific, IL). Purified proteins were analyzed by SDS-PAGE gels. FIGS. 5A and 5B show SDS gel images of anti-CD19-Fab-GCN4$_{C\text{-}term}$ (Lane 9) in non-reducing and reducing (with 50 mM DTT) conditions, respectively.

Example 6

Cloning, Expression and Purification of Anti-CD19-IgG-GCN4$_{hinge}$

Cloning: Mammalian expression vector of CD19 IgG heavy chain was generated by in-frame ligation of amplified CD19 Fab heavy chain (VH and CH1) to pFuse-hIgG1-Fc backbone vector (InvivoGen, CA). A gene encoding antibody CD19 light chain was amplified and cloned into the pFuse vector without hIgG1 Fc fragment. A gene encoding GCN4 (NYHLENEVARLKKL=SEQ ID NO: 3) with GGGGS (SEQ ID NO: 48) linker at N-terminal end of GCN4 and GGS (SEQ ID NO: 49) at C-terminal of GCN4 ("linker-GCN4-linker") was synthesized as oligonucleotides. Subsequently, anti-CD19-IgG-GCN4$_{hinge}$ fusion proteins were created by grafting the linker-GCN4-linker between the C terminus of the Fab heavy chain at C223 and the hinge region. Thus, the linker-GCN4-linker extends the hinge region of the IgG, mimicking an IgG3 structure with an elongated hinge region. The resulting mammalian expression vectors were confirmed by DNA sequencing.

Expression and Purification: anti-CD19-IgG-GCN4$_{hinge}$ was expressed through transient transfection of FreeStyle HEK 293 cells with expression vectors of CD19-IgG light chain and GCN4-CD19 hinge heavy chain, according to the manufacturer's protocol. Briefly, 28 mL FreeStyle HEK 293 cells containing 3×107 cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% $CO_2$ environment at 37° C. Culture medium containing secreted proteins was harvested at 48 and 96 hours after transfection. GCN4-CD19 hinge IgG was purified by Protein G chromatography (Thermo Fisher Scientific, IL). Purified proteins were analyzed by SDS-PAGE gels. FIGS. 5A & 5B show SDS gel images of anti-CD19-IgG-GCN4$_{hinge}$ (Lane 5) in non-reducing and reducing (with 50 mM DTT) conditions, respectively.

Example 7

Cloning, Expression and Purification of Anti-CD19-IgG-GCN4$_{CL1}$

Cloning: Mammalian expression vector of CD19 IgG heavy chain was generated by in-frame ligation of amplified CD19 Fab heavy chain (VH and CH1) to pFuse-hIgG1-Fc backbone vector (InvivoGen, CA). A gene encoding antibody CD19 light chain was amplified and cloned into the pFuse vector without hIgG1 Fc fragment. A gene encoding GCN4 (NYHLENEVARLKKL=SEQ ID NO: 3) with GGGGS (SEQ ID NO: 48) linker at both ends was synthesized as oligonucleotides. Subsequently, anti-CD19-IgG-GCN4$_{CL1}$ fusion proteins were created by replacing the K169 in CL region of CD19 light chain with GCN4 with linker sequences at both ends. The resulting mammalian expression vectors were confirmed by DNA sequencing.

Expression and Purification: anti-CD19-IgG-GCN4$_{CL1}$ was expressed through transient transfection of FreeStyle HEK 293 cells with expression vectors of CD19-IgG heavy chain and GCN4-CD19-CL1 light chain, according to the manufacturer's protocol. Briefly, 28 mL FreeStyle HEK 293 cells containing 3×10$^7$ cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% $CO_2$ environment at 37° C. Culture medium containing secreted proteins was harvested at 48 and 96 hours after transfection. anti-CD19-IgG-GCN4$_{CL1}$ was purified by Protein G chromatography (Thermo Fisher Scientific, IL). Purified proteins were analyzed by SDS-PAGE gels. FIGS. 5A & 5B show SDS gel images of anti-CD19-IgG-GCN4$_{CL1}$ (Lane 4) in non-reducing and reducing (with 50 mM DTT) conditions, respectively.

Example 8

Cloning, Expression and Purification of Anti-CD19-Fab-GCN4$_{CL1}$

Cloning: Mammalian expression vector of CD19 Fab heavy chain was generated by ligation of amplified CD19 Fab heavy chain (VH and CH1) to pFuse-hIgG1-Fc backbone vector (InvivoGen, CA) without Fc fragment. A gene encoding antibody CD19 light chain was amplified and cloned into the pFuse vector without hIgG1 Fc fragment. A gene encoding GCN4 (NYHLENEVARLKKL=SEQ ID NO: 3) with GGGGS (SEQ ID NO: 48) linker at both ends was synthesized as oligonucleotides. Subsequently, anti-CD19-Fab-GCN4$_{CL1}$ fusion proteins were created by replacing the K169 in CL region of CD19 light chain with GCN4 with linker sequences at both ends. The resulting mammalian expression vectors were confirmed by DNA sequencing.

Expression and Purification: anti-CD19-Fab-GCN4$_{CL1}$ was expressed through transient transfection of FreeStyle HEK 293 cells with expression vectors of CD19-Fab heavy chain and GCN4-CD19-CL light chain, according to the manufacturer's protocol. Briefly, 28 mL FreeStyle HEK 293 cells containing 3×10$^7$ cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% $CO_2$ environment at 37° C. Culture medium containing secreted proteins was harvested at 48 and 96 hours after transfection. The anti-CD19-Fab-GCN4$_{CL1}$ was purified by Protein G chromatography (Thermo Fisher Scientific, IL). Purified proteins were analyzed by SDS-PAGE gels. FIGS. 5A & 5B show SDS gel images of anti-CD19-Fab-GCN4$_{CL1}$ (Lane 8) in non-reducing and reducing (with 50 mM DTT) conditions, respectively.

Example 9

Cloning, Expression and Purification of Anti-CD19-Fab-GCN4$_{LC1-N-term}$

Cloning: Mammalian expression vector of CD19 Fab heavy chain was generated by ligation of amplified CD19 Fab heavy chain (VH and CH1) to pFuse-hIgG1-Fc backbone vector (InvivoGen, CA) without Fc fragment. A gene encoding antibody CD19 light chain was amplified and cloned into the pFuse vector without hIgG1 Fc fragment. A gene encoding GCN4 (NYHLENEVARLKKL=SEQ ID NO: 3) with GGGGS (SEQ ID NO: 48) linker at C-terminal end of GCN4 with was synthesized as oligonucleotides. Subsequently, anti-CD19-Fab-GCN4$_{LC1-N-term}$ fusion proteins were created by fusing the linker-GCN4 to the N terminus of the Fab light chain. The resulting mammalian expression vectors were confirmed by DNA sequencing.

Expression and Purification: anti-CD19-Fab-GCN4$_{LC1-N-term}$ was expressed through transient transfection of FreeStyle HEK 293 cells with expression vectors of CD19-Fab light chain and GCN4-CD19-C-term, according to the manufacturer's protocol. Briefly, 28 mL FreeStyle HEK 293 cells containing 3×107 cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% $CO_2$ environment at 37° C. Culture medium containing secreted proteins was harvested at 48 and 96 hours after transfection. anti-CD19-Fab-GCN4$_{LC1\text{-}N\text{-}term}$ was purified by Protein G chromatography (Thermo Fisher Scientific, IL). Purified proteins were analyzed by SDS-PAGE gels. FIGS. 5A and 5B show SDS gel images of anti-CD19-Fab-GCN4$_{LC1\text{-}N\text{-}term}$ (Lane 10) in non-reducing and reducing (with 50 mM DTT) conditions, respectively.

Example 10

Cytotoxicity of Anti-CD19 Fab-GCN4$_{CL1}$, Anti-CD19 IgG$_{FcNull}$-GCN4 and Anti-CD19 Fab-GCN4$_{C\text{-}term}$ CAR-EC Switches Peptide CAR-EC switches were created by fusing 14 amino acids of the GCN4 yeast transcription factor peptide sequence 7P14P (defined in Zahnd et al. (2004) Directed in vitro evolution and crystallographic analysis of a peptide-binding single chain antibody fragment (scFv) with low picomolar affinity, The Journal of Biological Chemistry 279, 18870-18877). The 14 amino acids were chosen based on those defined in crystal structure 1P4B of GCN4 peptide 7P14P with scFv c11L32Ser. The switches were constructed by either fusing the GCN4 peptide sequence to the C-terminus of the heavy chain of the Fab antibody or by fusing the GCN4 peptide sequence in the CL loop of the light chain of the Fab or IgG antibody. All expressions were carried out in CHO or HEK cells.

Figure 2:
FIG. 2 depicts a PDB 1P4B crystal structure of an affinity matured scFv (light and medium gray represent light chain and heavy chain) bound to a peptide derived from the yeast transcription factor GCN4 (7P-14P) (dark grey represents the GCN4 peptide).
Figure 3:
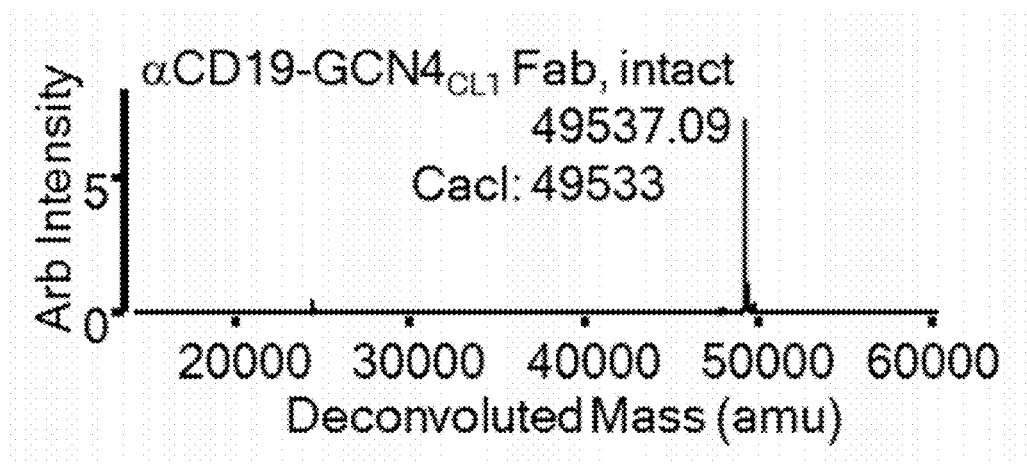
FIG. 3 shows mass spectrometry of an anti-CD19-Fab-GCN4$_{CL1}$ CAR-EC switch. Calculated: 49533, found: 49537.09.

To create a grafted GCN4 peptide based anti-CD19 CAR-T switch (SEQ ID NO: 30), the peptide NYHLENE-VARLKKL (SEQ ID NO: 3), suggested to be the minimal binding epitope according to the crystal structure (PDB: 1P4B) (see FIG. 2) from the yeast transcription factor GCN4 peptide (7P14P) RMKQLEPKVEELLPKNYHLENE-VARLKKLVGER (SEQ ID NO: 2), was grafted to the mouse anti-human CD19 Fab clone FMC63. The graft was carried out by replacing K63 (as counted from the N terminus of the constant region, which would be K169 when counting from the N terminus of the mature protein) of the light chain with the sequence GGGGSNYHLENEVARLK-KLGGGGS (SEQ ID NO: 4)—the GCN4 epitope flanked by GGGGS linkers (SEQ ID NO: 48). The mass spec of anti-CD19 Fab$_{CL1}$-GCN4 is provided below (FIG. 3). Alternatively, the peptide is grafted to the heavy chain (SEQ ID NO: 29).

The cytotoxic activity of the anti-CD19 Fab$_{CL1}$-GCN4 switch was assessed with the human PBMCs transduced with LV-EF1a-GCN4 (52SR4) to create CAR-T-GCN4 at E:T ratios of 10:1 and 24 hour incubation. Activity was assessed against NALM-6 (CD19$^+$), RS4; 11 (CD19$^+$), or RPMI-8226 (CD19$^-$) (Table 1). The activity of the IgG (FcNull) switch was assessed against RS4; 11 (CD19$^+$), or K562 (CD19$^-$) (Table 2). The activity of the C-terminal switch was assessed against RS4; 11 (CD19$^+$), or K562 (CD19$^-$) (Table 3).

TABLE 1

Cytotoxicity of the anti-CD19 Fab$_{CL1}$-GCN4 switch

| Concentration (pM) | % Cytotoxicity | | |
|---|---|---|---|
| | NALM-6 (CD19 positive) | RS4;11 (CD19 positive) | RPMI-8226 (CD19 negative) |
| 10 | 86.74405 | 104.0488 | 15.20283 |
| 1 | 82.23607 | 90.00308 | 8.149928 |
| 0.1 | 77.28449 | 84.11992 | 3.819127 |
| 0.01 | 47.15363 | 45.37116 | 2.656606 |
| 0.001 | −5.794394 | −2.258805 | −4.993927 |
| 0.0001 | −7.191706 | −8.02902 | −7.662813 |
| 0.00001 | −4.779683 | −2.792706 | −1.318068 |

TABLE 2

Cytotoxicity of anti-CD19 IgG$_{FcNull}$-GCN4 switch

| Concentration (pM) | % Cytotoxicity | |
|---|---|---|
| | RS4;11 (CD19 positive) | K562 (CD19 negative) |
| 1 | 53.56274 | 6.218475 |
| 0.1 | 48.75237 | 1.844815 |
| 0.01 | 38.21278 | −2.777584 |
| 0.001 | 12.10702 | −2.964143 |
| 0.0001 | 0.1621473 | −6.301391 |
| 0.00001 | −0.9188344 | −4.891867 |

TABLE 3

Cytotoxicity of anti-CD19 Fab$_{C\text{-}term}$-GCN4 switch

| Concentration (nM) | % Cytotoxicity | |
|---|---|---|
| | RS4;11 (CD19 positive) | K562 (CD19 negative) |
| 10 | 92.10811 | 1.44819 |
| 1 | 76.75676 | −3.445695 |
| 0.1 | 66.59459 | −2.197255 |
| 0.01 | 60.97298 | −1.348315 |
| 0.001 | 8.216215 | −2.147315 |
| 0.0001 | −2.162161 | −3.046195 |
| 0.00001 | 1.945946 | −0.299624 |

Example 11

Figure 4:
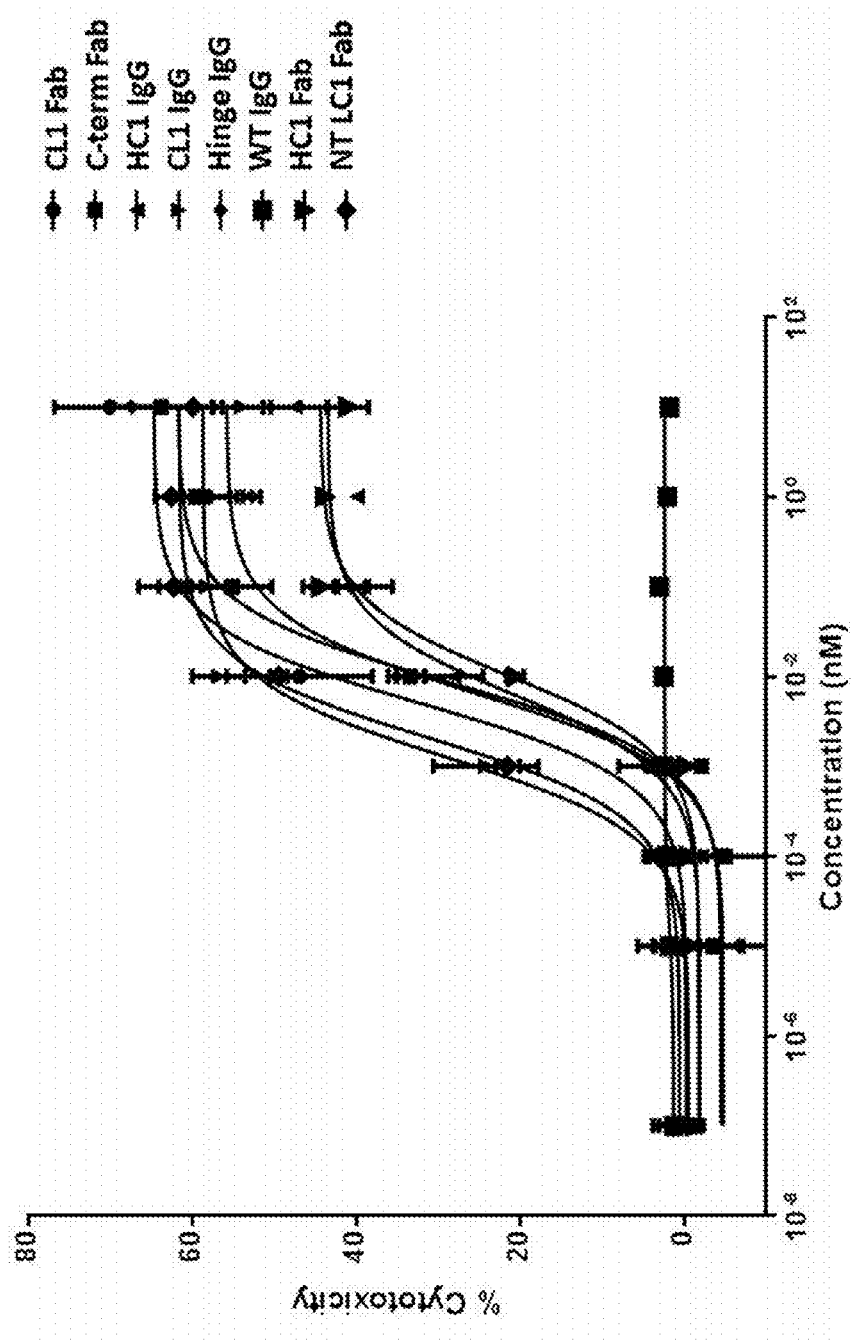
FIG. 4 shows cytotoxicity of an anti-GCN4 CAR T-cell with various anti-CD19 antibodies or antibody fragments with a GCN4 peptide grafted or fused to various regions or domains of the anti-CD19 antibodies or antibody fragments.
Figure 6:
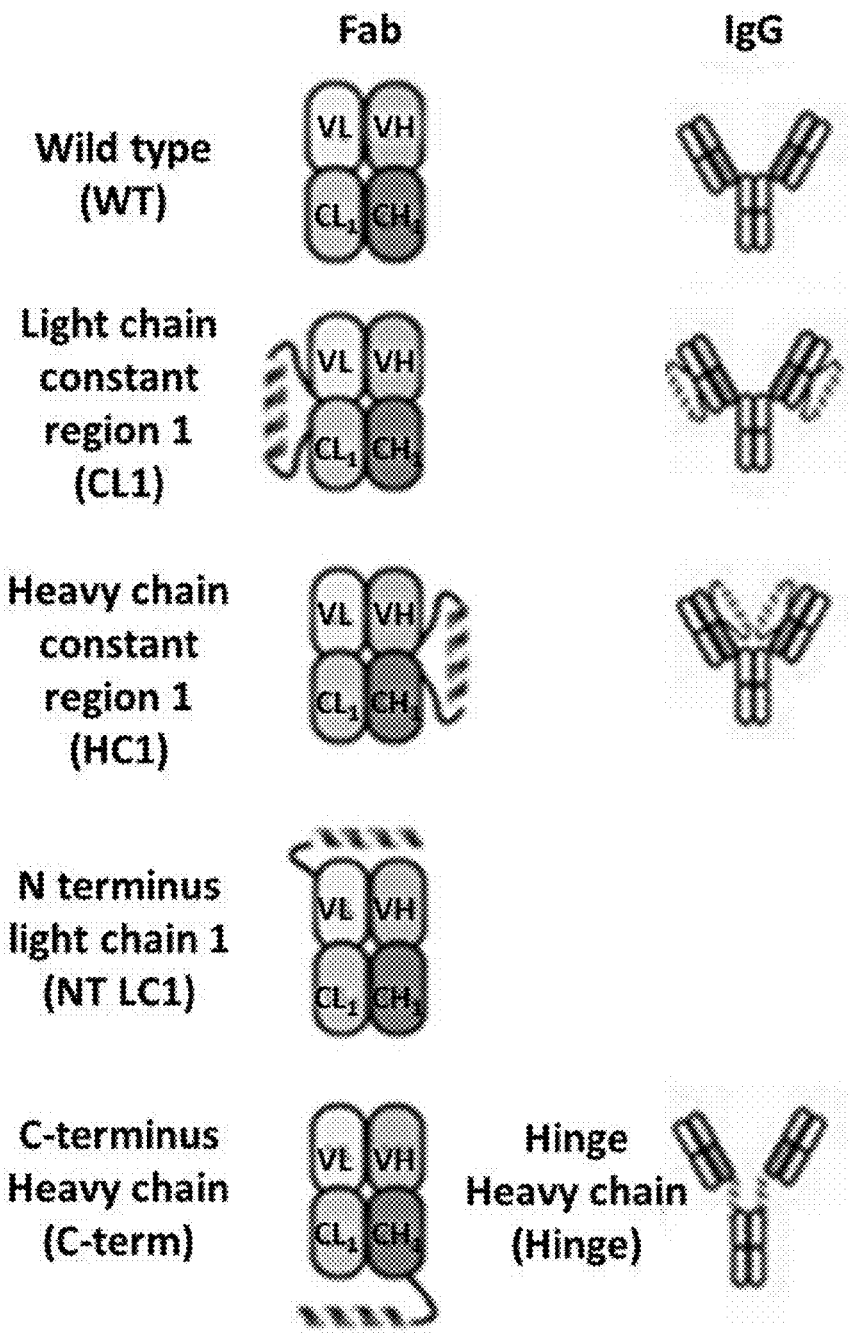
FIG. 6 depicts a yeast GCN4 peptide grafting positions in an anti-CD19 Fab (FMC63).

Cytotoxicity of Various Anti-CD19-GCN4 CAR EC Switches with GCN4 Grafted/Fused to Different Regions of an Anti-CD19 Antibody or Antibody Fragment The cytotoxic activities of various anti-CD19-GCN4 CAR-EC switches grafted/fused to different regions of anti-CD19 FMC63 antibodies or antibody fragments were assessed with the human PBMCs transduced with LV-EF1a-GCN4 (52SR4) to create CAR-T-GCN4 at E:T ratios of 10:1 and 24 hour incubation. Switches tested were anti-CD19 Fab$_{CL1}$-GCN4 ("CL1 Fab), anti-CD19-GCN4 Fab$_{C\text{-}term}$ ("C-term Fab), anti-CD19 IgG$_{HC1}$-GCN4 ("HC1 IgG"), anti-CD19 IgG$_{CL1}$-GCN4 ("CL1 IgG"), anti-CD19 IgG$_{Hinge}$-GCN4 ("Hinge IgG"), anti-CD19 IgG$_{WT}$-GCN4 ("Wt IgG"), anti-CD19 Fab$_{HC1}$-GCN4 ("HC1 Fab"), and anti-CD19 Fab$_{N\text{-}term\ LC1}$-GCN4 ("N-term LC1 Fab"). Activities were assessed against RS4; 11 (CD19$^+$) (FIG. 4, Table 4). FIG. 6 depicts the grafting positions of switches described in this example. The CL1 and HC1 grafting positions were applied to both Fab and IgG formats. The N-terminus grafting is shown as grafted to the light chain, however N-terminal grafting is not restricted to the light chain or Fab and may also be grafted to the heavy chain as well as the IgG format. The C-term position on the Fab is isosteric with the hinge IgG. In this context all Fab constructs are monovalent and all IgG constructs are bivalent, but these are not a necessary requirements for CAR-EC switches in general.

TABLE 4

Cytotoxicity of anti-CD19-GCN4 switches

| Switch Conc (nM) | CL1 Fab | C-term Fab | HC1 IgG | CL1 IgG | Hinge IgG | WT IgG | HC1 Fab | N-term LC1 Fab |
|---|---|---|---|---|---|---|---|---|
| 10 | 70.10483 | 63.81551 | 47.46331 | 54.02444 | 67.4252 | 1.785714 | 41.07143 | 59.97437 |
| 1 | 58.28092 | 59.53878 | 39.91614 | 59.58702 | 52.76022 | 2.040816 | 43.87755 | 62.53738 |
| 0.1 | 60.54507 | 55.26205 | 39.16142 | 58.3228 | 40.62368 | 3.061224 | 44.38776 | 62.28107 |
| 0.01 | 46.96017 | 33.37526 | 28.09225 | 56.80573 | 35.0611 | 2.55102 | 20.66327 | 49.46604 |
| 0.001 | 4.444445 | −2.09644 | 1.174004 | 24.18879 | 2.697009 | 2.55102 | −0.2551 | 21.52926 |
| 0.0001 | 2.180294 | −4.61216 | −2.09644 | 1.685631 | −5.14117 | 2.040817 | −0.5102 | 3.075609 |
| 0.00001 | 1.425577 | −3.60587 | −1.09015 | 0.927097 | −6.65823 | 1.785714 | −0.7653 | 5.07E−07 |
| 1E−07 | 0.922432 | −1.34172 | 0.419288 | 0.674253 | −1.60135 | 1.27551 | −1.27551 | 1.281505 |

Example 12

In Vivo Efficacy of Anti-CD19-Fab-GCN4CL1 CAR EC Switch and Anti-GCN4 CAR T-Cells (swiCAR T-Cells) in a Xenograft Tumor Mouse Model To assess swiCAR-T cell in vivo activity, a pilot study with an orthotopic (liquid) xenograft tumor model based on luciferized NALM-6 cells was conducted. In this model swiCAR T-cells demonstrated regression after just 5 days of daily treatment with 0.5 mg/kg of anti-CD19 (GCN4) CL1 Fab. Treatment with the wild type anti-CD19 Fab with swiCAR T-cells were not capable of mediating tumor regression (not significant by one-way ANOVA). These results demonstrate the ability to redirect swiCAR T-cells in vivo. Experiment details: $10^6$ luciferized NALM-6 cells were injected I.V. into nonobese diabetic-severe combined immunodeficiency (NOD-SCID-γ−/−, NSG) mice. Six days later, $30\times10^6$ swiCAR T-cells or CART-19 cells (50% transduced) were infused I.V. Dosing of αCD19-Fab-GCN4-CL1 (I.V.) began on the same day, q.d. 0.5 mg/kg. After 5 days of dosing (day 11) mice were injected with luciferin and imaged on an in vivo imaging system (IVIS), n=3 or 4, average radiance (p/s/cm²/sr) plotted measured per mouse, and plotted mean±SEM, **p≤0.05, one-way ANOVA. The difference between no treatment and swiCAR-T+WT Fab is not statistically significant. Results are shown in FIG. 7A.

Example 13

Cloning, Expression and Purification of Anti-BCMA-IgG-GCN4$_{CL1}$

Cloning: Mammalian expression vector of CD19 IgG heavy chain was generated by in-frame ligation of amplified anti-BCMA IgG heavy chain (VH and CH1) to pFuse-hIgG1-Fc backbone vector (InvivoGen, CA). A gene encoding antibody BCMA light chain was amplified and cloned into the pFuse vector without hIgG1 Fc fragment. A gene encoding GCN4 (NYHLENEVARLKKL=SEQ ID NO: 3) with GGGGS (SEQ ID NO: 48) linker at both ends was synthesized as oligonucleotides. Subsequently, anti-BCMA-IgG-GCN4$_{CL1}$ fusion proteins were created by grafting GCN4 with linker sequences at both ends into the CL region of the anti-BCMA light chain. The resulting mammalian expression vectors were confirmed by DNA sequencing.

Expression and Purification: anti-BCMA-IgG-GCN4$_{CL1}$ was expressed through transient transfection of FreeStyle HEK 293 cells with expression vectors of BCMA-IgG heavy chain and GCN4-BCMA-CL1 light chain, according to the manufacturer's protocol. Briefly, 28 mL FreeStyle HEK 293 cells containing $3\times10^7$ cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc). After the plasmids were incubated with 293fectin for 30 min, the lipoplex mixture was added to the cell suspension. Cells were then shaken at 125 rpm in a 5% $CO_2$ environment at 37° C. Culture medium containing secreted proteins was harvested at 48 and 96 hours after transfection. anti-BCMA-IgG-GCN4$_{CL1}$ was purified by Protein G chromatography (Thermo Fisher Scientific, IL).

Example 14

Cytotoxicity of Anti-BCMA-IgG-GCN4$_{CL1}$ CAR EC Switch with GCN4 Grafted to the Light Chain of an Anti-BCMA Antibody or Antibody Fragment The cytotoxic activity of the anti-BCMA-IgG-GCN4$_{CL1}$ CAR-EC switch was assessed with the human PBMCs transduced with LV-EF1a-GCN4(52SR4) to create CAR-T-GCN4 at E:T ratios of 10:1 and 24 hour incubation. Transduction efficiency of PBMCs was approximately 50%. Activities were assessed against OPM2 (BCMA+), by quantifying lactate dehydrogenase due to cytolysis of target cells (FIG. 8, Table 5).

TABLE 5

Cytotoxicity of anti-BCMA-IgG-GCN4$_{CL1}$ CAR-EC switch and anti-GCN4 CAR-T cell

| anti-BCMA-IgG-GCN4$_{CL1}$ switch concentration [pM] | % cytotoxicity |
|---|---|
| 10000.000 | 35.52758 |
| 1000.000 | 35.06853 |
| 100.000 | 41.44725 |
| 10.000 | 31.59707 |
| 1.000 | 5.575391 |
| 0.100 | 1.13803 |
| 0.010 | 0.812881 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

TABLE 6

Chimeric Antigen Receptor -Nucleotide Sequence

| NAME | SEQ ID NO | SEQUENCE |
| --- | --- | --- |
| LV-EF1a-GCN4(52SR4)-BBZ | 1 | CAGGTGGCACTTTTCGGGGAAATGTGCGCGGAACCCCTA
TTTGTTTATTTTTCTAAATACATTCAAATATGTATCCGCTC
ATGAGACAATAACCCTGATAAATGCTTCAATAATATTGA
AAAAGGAAGAGTATGAGTATTCAACATTTCCGTGTCGCC
CTTATTCCCTTTTTTGCGGCATTTTGCCTTCCTGTTTTTGC
TCACCCAGAAACGCTGGTGAAAGTAAAAGATGCTGAAGA
TCAGTTGGGTGCACGAGTGGGTTACATCGAACTGGATCT
CAACAGCGGTAAGATCCTTGAGAGTTTTCGCCCCGAAGA
ACGTTTTCCAATGATGAGCACTTTTAAAGTTCTGCTATGT
GGCGCGGTATTATCCCGTATTGACGCCGGGCAAGAGCAA
CTCGGTCGCCGCATACACTATTCTCAGAATGACTTGGTTG
AGTACTCACCAGTCACAGAAAAGCATCTTACGGATGGCA
TGACAGTAAGAGAATTATGCAGTGCTGCCATAACCATGA
GTGATAACACTGCGGCCAACTTACTTCTGACAACGATCG
GAGGACCGAAGGAGCTAACCGCTTTTTTGCACAACATGG
GGGATCATGTAACTCGCCTTGATCGTTGGGAACCGGAGC
TGAATGAAGCCATACCAAACGACGAGCGTGACACCACGA
TGCCTGTAGCAATGGCAACAACGTTGCGCAAACTATTAA
CTGGCGAACTACTTACTCTAGCTTCCCGGCAACAATTAAT
AGACTGGATGGAGGCGGATAAAGTTGCAGGACCACTTCT
GCGCTCGGCCCTTCCGGCTGGCTGGTTTATTGCTGATAAA
TCTGGAGCCGGTGAGCGTGGGTCTCGCGGTATCATTGCA
GCACTGGGGCCAGATGGTAAGCCCTCCCGTATCGTAGTT
ATCTACACGACGGGGAGTCAGGCAACTATGGATGAACGA
AATAGACAGATCGCTGAGATAGGTGCCTCACTGATTAAG
CATTGGTAACTGTCAGACCAAGTTTACTCATATATACTTT
AGATTGATTTAAAACTTCATTTTTAATTTAAAAGGATCTA
GGTGAAGATCCTTTTTGATAATCTCATGACCAAAATCCCT
TAACGTGAGTTTTCGTTCCACTGAGCGTCAGACCCCGTAG
AAAAGATCAAAGGATCTTCTTGAGATCCTTTTTTTCTGCG
CGTAATCTGCTGCTTGCAAACAAAAAAACCACCGCTACC
AGCGGTGGTTTGTTTGCCGGATCAAGAGCTACCAACTCTT
TTTCCGAAGGTAACTGGCTTCAGCAGAGCGCAGATACCA
AATACTGTCCTTCTAGTGTAGCCGTAGTTAGGCCACCACT
TCAAGAACTCTGTAGCACCGCCTACATACCTCGCTCTGCT
AATCCTGTTACCAGTGGCTGCTGCCAGTGGCGATAAGTC
GTGTCTTACCGGGTTGGACTCAAGACGATAGTTACCGGA
TAAGGCGCAGCGGTCGGGCTGAACGGGGGGTTCGTGCAC
ACAGCCCAGCTTGGAGCGAACGACCTACACCGAACTGAG
ATACCTACAGCGTGAGCTATGAGAAAGCGCCACGCTTCC
CGAAGGGAGAAAGGCGGACAGGTATCCGGTAAGCGGCA
GGGTCGGAACAGGAGAGCGCACGAGGGAGCTTCCAGGG
GGAAACGCCTGGTATCTTTATAGTCCTGTCGGGTTTCGCC
ACCTCTGACTTGAGCGTCGATTTTTGTGATGCTCGTCAGG
GGGGCGGAGCCTATGGAAAAACGCCAGCAACGCGGCCTT
TTTACGGTTCCTGGCCTTTTGCTGGCCTTTTGCTCACATGT
TCTTTCCTGCGTTATCCCCTGATTCTGTGGATAACCGTATT
ACCGCCTTTGAGTGAGCTGATACCGCTCGCCGCAGCCGA
ACGACCGAGCGCAGCGAGTCAGTGAGCGAGGAAGCGGA
AGAGCGCCCAATACGCAAACCGCCTCTCCCCGCGCGTTG
GCCGATTCATTAATGCAGCTGGCACGACAGGTTTCCCGA
CTGGAAAGCGGGCAGTGAGCGCAACGCAATTAATGTGAG
TTAGCTCACTCATTAGGCACCCCAGGCTTTACACTTTATG
CTTCCGGCTCGTATGTTGTGTGGAATTGTGAGCGGATAAC
AATTTCACACAGGAAACAGCTATGACCATGATTACGCCA
AGCGCGCAATTAACCCTCACTAAAGGGAACAAAAGCTGG
AGCTGCAAGCTTAATGTAGTCTTATGCAATACTCTTGTAG
TCTTGCAACATGGTAACGATGAGTTAGCAACATGCCTTA
CAAGGAGAGAAAAAGCACCGTGCATGCCGATTGGTGGA
AGTAAGGTGGTACGATCGTGCCTTATTAGGAAGGCAACA
GACGGGTCTGACATGGATTGGACGAACCACTGAATTGCC
GCATTGCAGAGATATTGTATTTAAGTGCCTAGCTCGATAC
AATAAACGGGTCTCTCTGGTTAGACCAGATCTGAGCCTG
GGAGCTCTCTGGCTAACTAGGGAACCCACTGCTTAAGCC
TCAATAAAGCTTGCCTTGAGTGCTTCAAGTAGTGTGTGCC
CGTCTGTTGTGTGACTCTGGTAACTAGAGATCCCTCAGAC
CCTTTTAGTCAGTGTGGAAAATCTCTAGCAGTGGCGCCCG
AACAGGGACCTGAAAGCGAAAGGGAAACCAGAGCTCTC
TCGACGCAGGACTCGGCTTGCTGAAGCGCGCACGGCAAG |

TABLE 6-continued

Chimeric Antigen Receptor -Nucleotide Sequence

| NAME | SEQ ID NO | SEQUENCE |
|------|-----------|----------|
| | | AGGCGAGGGGCGGCGACTGGTGAGTACGCCAAAAATTTT |
| | | GACTAGCGGAGGCTAGAAGGAGAGAGATGGGTGCGAGA |
| | | GCGTCAGTATTAAGCGGGGGAGAATTAGATCGCGATGGG |
| | | AAAAAATTCGGTTAAGGCCAGGGGGAAAGAAAAAATAT |
| | | AAATTAAAACATATAGTATGGGCAAGCAGGGAGCTAGA |
| | | ACGATTCGCAGTTAATCCTGGCCTGTTAGAAACATCAGA |
| | | AGGCTGTAGACAAATACTGGGACAGCTACAACCATCCCT |
| | | TCAGACAGGATCAGAAGAACTTAGATCATTATATAATAC |
| | | AGTAGCAACCCTCTATTGTGTGCATCAAAGGATAGAGAT |
| | | AAAAGACACCAAGGAAGCTTTAGACAAGATAGAGGAAG |
| | | AGCAAAACAAAAGTAAGACCACCGCACAGCAAGCGGCC |
| | | GCTGATCTTCAGACCTGGAGGAGGAGATATGAGGGACAA |
| | | TTGGAGAAGTGAATTATATAAATATAAAGTAGTAAAAAT |
| | | TGAACCATTAGGAGTAGCACCCACCAAGGCAAAGAGAA |
| | | GAGTGGTGCAGAGAGAAAAAAGAGCAGTGGGAATAGGA |
| | | GCTTTGTTCCTTGGGTTCTTGGGAGCAGCAGGAAGCACTA |
| | | TGGGCGCAGCCTCAATGACGCTGACGGTACAGGCCAGAC |
| | | AATTATTGTCTGGTATAGTGCAGCAGCAGAACAATTTGCT |
| | | GAGGGCTATTGAGGCGCAACAGCATCTGTTGCAACTCAC |
| | | AGTCTGGGCATCAAGCAGCTCCAGGCAAGAATCCTGGC |
| | | TGTGGAAAGATACCTAAAGGATCAACAGCTCCTGGGGAT |
| | | TTGGGGTTGCTCTGGAAAACTCATTTGCACCACTGCTGTG |
| | | CCTTGGAATGCTAGTTGGAGTAATAAATCTCTGGAACAG |
| | | ATTGGAATCACACGACCTGGATGGAGTGGGACAGAGAA |
| | | ATTAACAATTACACAAGCTTAATACACTCCTTAATTGAAG |
| | | AATCGCAAAACCAGCAAGAAAAGAATGAACAAGAATTA |
| | | TTGGAATTAGATAAATGGGCAAGTTTGTGGAATTGGTTT |
| | | AACATAACAAATTGGCTGTGGTATATAAAATTATTCATA |
| | | ATGATAGTAGGAGGCTTGGTAGGTTTAAGAATAGTTTTT |
| | | GCTGTACTTTCTATAGTGAATAGAGTTAGGCAGGGATATT |
| | | CACCATTATCGTTTCAGACCCACCTCCCAACCCCGAGGG |
| | | GACCCGACAGGCCCGAAGGAATAGAAGAAGAAGGTGGA |
| | | GAGAGAGACAGAGACAGATCCATTCGATTAGTGAACGG |
| | | ATCTCGACGGTTAACTTTTAAAAGAAAAGGGGGGATTGG |
| | | GGGGTACAGTGCAGGGGAAAGAATAGTAGACATAATAG |
| | | CAACAGACATACAAACTAAAGAATTACAAAAACAAATTA |
| | | CAAAAATTCAAAATTTTATCGAGCTTTGCAAAGATGGAT |
| | | AAAGTTTTAAACAGAGAGGAATCTTTGCAGCTAATGGAC |
| | | CTTCTAGGTCTTGAAAGGAGTGCCTCGTGAGGCTCCGGT |
| | | GCCCGTCAGTGGGCAGAGCGCACATCGCCCACAGTCCCC |
| | | GAGAAGTTGGGGGGAGGGGTCGGCAATTGAACCGGTGC |
| | | CTAGAGAAGGTGGCGCGGGGTAAACTGGGAAAGTGATG |
| | | TCGTGTACTGGCTCCGCCTTTTTCCCGAGGGTGGGGGAGA |
| | | ACCGTATATAAGTGCAGTAGTCGCCGTGAACGTTCTTTTT |
| | | CGCAACGGGTTTGCCGCCAGAACACAGGTAAGTGCCGTG |
| | | TGTGGTTCCCGCGGGCCTGGCCTCTTTACGGGTTATGGCC |
| | | CTTGCGTGCCTTGAATTACTTCCACCTGGCTGCAGTACGT |
| | | GATTCTTGATCCCGAGCTTCGGGTTGGAAGTGGGTGGGA |
| | | GAGTTCGAGGCCTTGCGCTTAAGGAGCCCCTTCGCCTCGT |
| | | GCTTGAGTTGAGGCCTGGCCTGGGCGCTGGGGCCGCCGC |
| | | GTGCGAATCTGGTGGCACCTTCGCGCCTGTCTCGCTGCTT |
| | | TCGATAAGTCTCTAGCCATTTAAAATTTTTGATGACCTGC |
| | | TGCGACGCTTTTTTTCTGGCAAGATAGTCTTGTAAATGCG |
| | | GGCCAAGATCTGCACACTGGTATTTCGGTTTTTGGGGCCG |
| | | CGGGCGGCGACGGGGCCCGTGCGTCCCAGCGCACATGTT |
| | | CGGCGAGGCGGGGCCTGCGAGCGCGGCCACCGAGAATC |
| | | GGACGGGGGTAGTCTCAAGCTGGCCGGCCTGCTCTGGTG |
| | | CCTGGCCTCGCGCCGCCGTGTATCGCCCCGCCCTGGGCG |
| | | GCAAGGCTGGCCCGGTCGGCACCAGTTGCGTGAGCGGAA |
| | | AGATGGCCGCTTCCCGGCCCTGCTGCAGGGAGCTCAAAA |
| | | TGGAGGACGCGGCGCTCGGGAGAGCGGGCGGGTGAGTC |
| | | ACCCACACAAAGGAAAAGGGCCTTTCCGTCCTCAGCCGT |
| | | CGCTTCATGTGACTCCACGGAGTACCGGGCGCCGTCCAG |
| | | GCACCTCGATTAGTTCTCGAGCTTTTGGAGTACGTCGTCT |
| | | TTAGGTTGGGGGGAGGGGTTTTATGCGATGGAGTTTCCC |
| | | CACACTGAGTGGGTGGAGACTGAAGTTAGGCCAGCTTGG |
| | | CACTTGATGTAATTCTCCTTGGAATTTGCCCTTTTTGAGTT |
| | | TGGATCTTGGTTCATTCTCAAGCCTCAGACAGTGGTTCAA |
| | | AGTTTTTTTCTTCCATTTCAGGTGTCGTGAGGAATTCGGT |
| | | ACCGCGGCCGCCCGGGGATCCATGGCCTTACCAGTGACC |
| | | GCCTTGCTCCTGCCGCTGGCCTTGCTGCTCCACGCCGCCA |
| | | GGCCGGACGCCGTTGTGACCCAGGAATCCGCTCTGACCT |
| | | CTTCTCCAGGCGAAACCGTGACTCTGACTTGCCGTAGTAG |
| | | CACCGGGGCTGTGACCACATCTAACTATGCCAGTTGGGT |
| | | CCAGGAAAAACCGGATCACCTGTTTACTGGCCTGATTGG |
| | | CGGCACCAACAATCGCGCACCGGGTGTGCCCGCTCGTTT |

TABLE 6-continued

Chimeric Antigen Receptor -Nucleotide Sequence

| NAME | SEQ ID NO | SEQUENCE |
|------|-----------|----------|
| | | CAGCGGTTCCCTGATTGGGGACAAGGCAGCACTGACTAT |
| | | CACCGGCGCCCAGACCGAAGATGAGGCGATCTATTTTTG |
| | | CGTCCTGTGGTACAGCGACCATTGGGTGTTCGGGGGAGG |
| | | CACCAAACTGACAGTGCTGGGCGGAGGAGGAGGTTCAG |
| | | GAGGAGGAGGTAGCGGGGGAGGCGGTTCCGGGGGAGGC |
| | | GGTTCTGATGTGCAGCTGCAAGAATCCGGGCCAGGACTG |
| | | GTTGCGCCTTCTCAGAGTCTGTCAATTACATGTACTGTTA |
| | | GTGGCTTTCTGCTGACCGACTATGGTGTGAACTGGGTTCG |
| | | TCAGAGCCCAGGCAAGGGTCTGGAGTGGCTGGGAGTGAT |
| | | TTGGGGGGATGGAATCACAGACTACAATAGCGCACTGAA |
| | | ATCTCGGCTGAGTGTTACCAAAGATAACAGCAAGTCCCA |
| | | GGTCTTCCTGAAGATGAACAGCCTGCAAAGCGGCGACTC |
| | | CGCTCGCTATTACTGCGTTACCGGACTGTTTGATTATTGG |
| | | GGGCAGGGGACAACTCTGACTGTTTCCTCCACCACGACG |
| | | CCAGCGCCGCGACCACCAACACCGGCGCCCACCATCGCG |
| | | TCGCAGCCCCTGTCCCTGCGCCCAGAGGCGTGCCGGCCA |
| | | GCGGCGGGGGCGCAGTGCACACGAGGGGGCTGGACTT |
| | | CGCCTGTGATATCTACATCTGGGCGCCCTTGGCCGGGACT |
| | | TGTGGGGTCCTTCTCCTGTCACTGGTTATCACCCTTTACT |
| | | GCAAACGGGGCAGAAAGAAACTCCTGTATATATTCAAAC |
| | | AACCATTTATGAGACCAGTACAAACTACTCAAGAGGAAG |
| | | ATGGCTGTAGCTGCCGATTTCCAGAAGAAGAAGAAGGAG |
| | | GATGTGAACTGAGAGTGAAGTTCAGCAGGAGCGCAGAC |
| | | GCCCCCGCGTACAAGCAGGGCCAGAACCAGCTCTATAAC |
| | | GAGCTCAATCTAGGACGAAGAGAGGAGTACGATGTTTTG |
| | | GACAAGAGACGTGGCCGGGACCCTGAGATGGGGGGAAA |
| | | GCCGAGAAGGAAGAACCCTCAGGAAGGCCTGTACAATG |
| | | AACTGCAGAAAGATAAGATGGCGGAGGCCTACAGTGAG |
| | | ATTGGGATGAAAGGCGAGCGCCGGAGGGGCAAGGGGCA |
| | | CGATGGCCTTTACCAGGGTCTCAGTACAGCCACCAAGGA |
| | | CACCTACGACGCCCTTCACATGCAGGCCCTGCCCCCTCGC |
| | | TAAGTCGACAATCAACCTCTGGATTACAAAATTTGTGAA |
| | | AGATTGACTGGTATTCTTAACTATGTTGCTCCTTTTACGC |
| | | TATGTGGATACGCTGCTTTAATGCCTTTGTATCATGCTAT |
| | | TGCTTCCCGTATGGCTTTCATTTTCTCCTCCTTGTATAAAT |
| | | CCTGGTTGCTGTCTCTTTATGAGGAGTTGTGGCCCGTTGT |
| | | CAGGCAACGTGGCGTGGTGTGCACTGTGTTTGCTGACGC |
| | | AACCCCCACTGGTTGGGGCATTGCCACCACCTGTCAGCTC |
| | | CTTTCGGGACTTTCGCTTTCCCCCTCCCTATTGCCACGG |
| | | CGGAACTCATCGCCGCCTGCCTTGCCCGCTGCTGGACAG |
| | | GGGCTCGGCTGTTGGGCACTGACAATTCCGTGGTGTTGTC |
| | | GGGGAAGCTGACGTCCTTTCCATGGCTGCTCGCCTGTGTT |
| | | GCCACCTGGATTCTGCGCGGGACGTCCTTCTGCTACGTCC |
| | | CTTCGGCCCTCAATCCAGCGGACCTTCCTTCCCGCGGCCT |
| | | GCTGCCGGCTCTGCGGCCTCTTCCGCGTCTTCGCCTTCGC |
| | | CCTCAGACGAGTCGGATCTCCCTTTGGGCCGCCTCCCCGC |
| | | CTGGAATTCGAGCTCGGTACCTTTAAGACCAATGACTTAC |
| | | AAGGCAGCTGTAGATCTTAGCCACTTTTTAAAAGAAAAG |
| | | GGGGGACTGGAAGGGCTAATTCACTCCCAACGAAGACAA |
| | | GATCTGCTTTTTGCTTGTACTGGGTCTCTCTGGTTAGACC |
| | | AGATCTGAGCCTGGGAGCTCTCTGGCTAACTAGGGAACC |
| | | CACTGCTTAAGCCTCAATAAAGCTTGCCTTGAGTGCTTCA |
| | | AGTAGTGTGTGCCCGTCTGTTGTGTGACTCTGGTAACTAG |
| | | AGATCCCTCAGACCCTTTTAGTCAGTGTGGAAAATCTCTA |
| | | GCAGTAGTAGTTCATGTCATCTTATTATTCAGTATTTATA |
| | | ACTTGCAAAGAAATGAATATCAGAGAGTGAGAGGAACTT |
| | | GTTTATTGCAGCTTATAATGGTTACAAATAAAGCAATAG |
| | | CATCACAAATTTCACAAATAAAGCATTTTTTTCACTGCAT |
| | | TCTAGTTGTGGTTTGTCCAAACTCATCAATGTATCTTATC |
| | | ATGTCTGGCTCTAGCTATCCCGCCCCTAACTCCGCCCAGT |
| | | TCCGCCCATTCTCCGCCCCATGGCTGACTAATTTTTTTTAT |
| | | TTATGCAGAGGCCGAGGCCGCCTCGGCCTCTGAGCTATT |
| | | CCAGAAGTAGTGAGGAGGCTTTTTTGGAGGCCTAGGCTT |
| | | TTGCGTCGAGACGTACCCAATTCGCCCTATAGTGAGTCGT |
| | | ATTACGCGCGCTCACTGGCCGTCGTTTTACAACGTCGTGA |
| | | CTGGGAAAACCCTGGCGTTACCCAACTTAATCGCCTTGC |
| | | AGCACATCCCCCTTTCGCCAGCTGGCGTAATAGCGAAGA |
| | | GGCCCGCACCGATCGCCCTTCCCAACAGTTGCGCAGCCT |
| | | GAATGGCGAATGGCGCGACGCGCCCTGTAGCGGCGCATT |
| | | AAGCGCGGCGGGTGTGGTGGTTACGCGCAGCGTGACCGC |
| | | TACACTTGCCAGCGCCCTAGCGCCCGCTCCTTTCGCTTTC |
| | | TTCCCTTCCTTTCTCGCCACGTTCGCCGGCTTTCCCCGTCA |
| | | AGCTCTAAATCGGGGCTCCCTTTAGGGTTCCGATTTAGT |
| | | GCTTTACGGCACCTCGACCCCAAAAAACTTGATTAGGGT |
| | | GATGGTTCACGTAGTGGGCCATCGCCCTGATAGACGGTT |
| | | TTTCGCCCTTTGACGTTGGAGTCCACGTTCTTTAATAGTG |

TABLE 6-continued

Chimeric Antigen Receptor -Nucleotide Sequence

| NAME | SEQ ID NO | SEQUENCE |
|---|---|---|
| | | GACTCTTGTTCCAAACTGGAACAACACTCAACCCTATCTC GGTCTATTCTTTTGATTTATAAGGGATTTTGCCGATTTCG GCCTATTGGTTAAAAAATGAGCTGATTTAACAAAAATTT AACGCGAATTTTAACAAAATATTAACGTTTACAATTTCC |

TABLE 7

CAR Binding Region -Nucleotide & Amino Acid Sequences

| NAME | SEQ ID NO | SEQUENCE |
|---|---|---|
| yeast transcription factor GCN4 (7P14P) | 2 | RMKQLEPKVEELLPKNYH LENEVARLKKLVGER |
| yeast transcription factor GCN4 minimal binding peptide | 3 | NYHLENEVARLKKL |
| yeast transcription factor GCN4 minimal binding peptide with linkers | 4 | GGGGSNYHLENEVARLKK LGGGGS |
| Hydrophilic target peptide (HTP) | 5 | GGGGSDYKDDDDK |
| Hydrophilic target peptide (HTP) P | 6 | GGGGSDYKDDDDKP |
| FLAG® | 7 | DYKDDDDK |

TABLE 8

CAR-T switch targeting polypeptides-Nucleotide Sequence

| NAME | SEQ ID NO | SEQUENCE |
|---|---|---|
| Light chain of anti-CD19 antibody | 8 | GACATCCAGATGACACAGACTACATCCTCCCTGTCTGCCTCTC TGGGAGACAGAGTCACCATCAGTTGCAGGGCAAGTCAGGACA TTAGTAAATATTTAAATTGGTATCAGCAGAAACCAGATGGAA CTGTTAAACTCCTGATCTACCATACATCAAGATTACACTCAGG AGTCCCATCAAGGTTCAGTGGCAGTGGGTCTGGAACAGATTA TTCTCTCACCATTAGCAACCTGGAGCAAGAAGATATTGCCACT TACTTTTGCCAACAGGGTAATACGCTTCCGTACACGTTCGGAG GGGGGACCAAGCTTGAGATCAAACGAACTGTGGCTGCACCAT CTGTCTTCATCTTCCCGCCATCTGATGAGCAGTTGAAATCTGG AACTGCCTCTGTCGTGTGCCTGCTGAATAACTTCTATCCCAGA GAGGCCAAAGTACAGTGGAAGGTGGATAACGCCCTCCAATCG GGTAACTCCCAGGAGAGTGTCACAGAGCAGGACAGCAAGGAC AGCACCTACAGCCTCAGCAGCACCCTGACGCTGAGCAAAGCA GACTACGAGAAACACAAAGTCTACGCCTGCGAAGTCACCCAT CAGGGCCTGTCCTCGCCCGTCACAAAGAGCTTCAACAGGGGA GAGTGT |
| Heavy chain of anti-CD19 antibody Fab | 9 | GAGGTGAAACTGCAGGAGTCAGGACCTGGCCTGGTGGCGCCC TCACAGAGCCTGTCCGTCACATGCACTGTCTCAGGGGTCTCAT TACCCGACTATGGTGTAAGCTGGATTCGCCAGCCTCCACGAAA GGGTCTGGAGTGGCTGGGAGTAATATGGGGTAGTGAAACCAC ATACTATAATTCAGCTCTCAAATCCAGACTGACCATCATCAAG GACAACTCCAAGAGCCAAGTTTTCTTAAAAATGAACAGTCTG CAAACTGATGACACAGCCATTTACTACTGTGCCAAACATTATT ACTACGGTGGTAGCTATGCTATGGACTACTGGGGCCAAGGAA CCTCAGTCACCGTCTCCTCAGCCTCCACCAAGGGCCCATCGGT CTTCCCCCTGGCACCCTCCTCCAAGAGCACCTCTGGGGGCACA GCGGCCCTGGGCTGCCTGGTCAAGGACTACTTCCCCGAACCG GTGACGGTGTCGTGGAACTCAGGCGCCCTGACCAGCGGCGTG CACACCTTCCCGGCTGTCCTACAGTCCTCAGGACTCTACTCCC TCAGCAGCGTGGTGACTGTGCCCTCTAGCAGCTTGGGCACCCA GACCTACATCTGCAACGTGAATCACAAGCCCAGCAACACCAA GGTGGACAAGAAAGTTGAGCCCAAATCTTGT |
| Heavy chain of anti-CD19 IgG | 10 | GAGGTGAAACTGCAGGAGTCAGGACCTGGCCTGGTGGCGCCC TCACAGAGCCTGTCCGTCACATGCACTGTCTCAGGGGTCTCAT TACCCGACTATGGTGTAAGCTGGATTCGCCAGCCTCCACGAAA GGGTCTGGAGTGGCTGGGAGTAATATGGGGTAGTGAAACCAC ATACTATAATTCAGCTCTCAAATCCAGACTGACCATCATCAAG GACAACTCCAAGAGCCAAGTTTTCTTAAAAATGAACAGTCTG CAAACTGATGACACAGCCATTTACTACTGTGCCAAACATTATT |

TABLE 8-continued

CAR-T switch targeting polypeptides-Nucleotide Sequence

| NAME | SEQ ID NO | SEQUENCE |
|---|---|---|
| | | ACTACGGTGGTAGCTATGCTATGGACTACTGGGGCCAAGGAA<br>CCTCAGTCACCGTCTCCTCAGCCTCCACCAAGGGCCCATCGGT<br>CTTCCCCCTGGCACCCTCCTCCAAGAGCACCTCTGGGGGCACA<br>GCGGCCCTGGGCTGCCTGGTCAAGGACTACTTCCCCGAACCG<br>GTGACGGTGTCGTGGAACTCAGGCGCCCTGACCAGCGGCGTG<br>CACACCTTCCCGGCTGTCCTACAGTCCTCAGGACTCTACTCCC<br>TCAGCAGCGTGGTGACTGTGCCCTCTAGCAGCTTGGGCACCCA<br>GACCTACATCTGCAACGTGAATCACAAGCCCAGCAACACCAA<br>GGTGGACAAGAAAGTTGAGCCCAAATCTTGTGACAAAACTCA<br>CACATGCCCACCGTGCCCAGCACCTCCAGTCGCCGGACCGTCA<br>GTCTTCCTCTTCCCTCCAAAACCCAAGGACACCCTCATGATCT<br>CCCGGACCCCTGAGGTCACATGCGTGGTGGTGGACGTGAGCC<br>ACGAAGACCCTGAGGTCAAGTTCAACTGGTACGTGGACGGCG<br>TGGAGGTGCATAATGCCAAGACAAAGCCGCGGGAGGAGCAGT<br>ACAACAGCACGTACCGTGTGGTCAGCGTCCTCACCGTCCTGCA<br>CCAGGACTGGCTGAATGGCAAGGAGTACAAGTGCAAGGTCTC<br>CAACAAAGGCCTCCCAAGCTCCATCGAGAAAACCATCTCCAA<br>AGCCAAAGGGCAGCCCCGAGAACCACAGGTGTACACCCTGCC<br>TCCATCCCGGGATGAGCTGACCAAGAACCAGGTCAGCCTGAC<br>CTGCCTGGTCAAAGGCTTCTATCCCAGCGACATCGCCGTGGAG<br>TGGGAGAGCAATGGGCAGCCGGAGAACAACTACAAGACCAC<br>GCCTCCCGTGCTGGACTCCGACGGCTCCTTCTTCCTCTACAGC<br>AAGCTCACCGTGGACAAGAGCAGGTGGCAGCAGGGGAACGTC<br>TTCTCATGCTCCGTGATGCATGAGGCTCTGCACAACCACTACA<br>CGCAGAAGAGCCTCTCCCTGTCTCCGGGTAAA |
| Light chain of<br>Trastuzumab<br>(anti-Her2) | 11 | ATGAAAAAGAATATCGCATTTCTTCTTGCTAGCATGTTCGTTT<br>TTTCTATTGCTACAAACGCATACGCTGACATCCAGATGACCCA<br>GTCTCCATCCTCCCTGTCTGCATCTGTAGGAGACAGAGTCACC<br>ATCACTTGCCGGGCAAGTCAGGATGTGAATACCGCGGTCGCA<br>TGGTATCAGCAGAAACCAGGGAAAGCCCCTAAGCTCCTGATC<br>TATTCTGCATCCTTCTTGTATAGTGGGGTCCCATCAAGGTTCA<br>GTGGCAGTAGATCTGGGACAGATTTCACTCTCACCATCAGCAG<br>TCTGCAACCTGAAGATTTTGCAACTTACTACTGTCAACAGCAT<br>TACACTACCCCTCCGACGTTCGGCCAAGGTACCAAGCTTGAGA<br>TCAAACGAACTGTGGCTGCACCATCTGTCTTCATCTTCCCGCC<br>ATCTGATGAGCAGTTGAAATCTGGAACTGCCTCTGTCGTGTGC<br>CTGCTGAATAACTTCTATCCCAGAGAGGCCAAAGTACAGTGG<br>AAGGTGGATAACGCCCTCCAATCGGGTAACTCCCAGGAGAGT<br>GTCACAGAGCAGGACAGCAAGGACAGCACCTACAGCCTCAGC<br>AGCACCCTGACGCTGAGCAAAGCAGACTACGAGAAACACAAA<br>GTCTACGCCTGCGAAGTCACCCATCAGGGCCTGTCCTCGCCCG<br>TCACAAAGAGCTTCAACAGGGGAGAGTGT |
| Heavy chain<br>of<br>Trastuzumab<br>(anti-Her2) | 12 | ATGAAAAAGAATATCGCATTTCTTCTTGCATCTATGTTCGTTTT<br>TTCTATTGCTACAAACGCGTACGCTGAGGTGCAGCTGGTGGA<br>TCTGGAGGAGGCTTGGTCCAGCCTGGGGGGTCCCTGAGACTCT<br>CCTGTGCAGCCTCTGGGTTCAATATTAAGGACACTTACATCCA<br>CTGGGTCCGCCAGGCTCCAGGGAAGGGGCTGGAGTGGGTCGC<br>ACGTATTTATCCTACCAATGGTTACACACGCTACGCAGACTCC<br>GTGAAGGGCCGATTCACCATCTCCGCAGACACTTCCAAGAAC<br>ACGGCGTATCTTCAAATGAACAGCCTGAGAGCCGAGGACACG<br>GCCGTGTATTACTGTTCGAGATGGGGCGGTGACGGCTTCTATG<br>CCATGGACTACTGGGGCCAAGGAACCCTGGTCACCGTCTCCTC<br>AGCCTCCACCAAGGGCCCATCGGTCTTCCCCCTGGCACCCTCC<br>TCCAAGAGCACCTCTGGGGGCACAGCGGCCCTGGGCTGCCTG<br>GTCAAGGACTACTTCCCCGAACCGGTGACGGTGTCGTGGAAC<br>TCAGGCGCCCTGACCAGCGGCGTGCACACCTTCCCGGCTGTCC<br>TACAGTCCTCAGGACTCTACTCCCTCAGCAGCGTGGTGACTGT<br>GCCCTCTAGCAGCTTGGGCACCCAGACCTACATCTGCAACGTG<br>AATCACAAGCCCAGCAACACCAAGGTGGACAAGAAAGTTGAG<br>CCCAAATCTTGTGACAAAACTCACACA |
| Light Chain of<br>Rituximab<br>(anti-CD20) | 13 | ATGAAAAAGAATATCGCATTTCTTCTTGCTAGCATGTTCGTTT<br>TTTCTATTGCTACAAACGCATACGCTCAGATTGTGCTGAGCCA<br>GAGCCCGGCGATTCTGAGCGCGAGCCCGGGCGAAAAAGTGAC<br>CATGACCTGCCGCGCGAGCAGCAGCGTGAGCTATATTCATTG<br>GTTTCAGCAGAAACCGGGCAGCAGCCCGAAACCGTGGATTTA<br>TGCGACCAGCAACCTGGCGAGCGGCGTGCCGGTGCGCTTTAG<br>CGGCAGCGGCAGCGGCACCAGCTATAGCCTGACCATTAGCCG<br>CGTGGAAGCGGAAGATGCGGCGACCTATTATTGCCAGCAGTG<br>GACCAGCAACCCGCCGACCTTTGGCGGCGGCACCAAGCTTGA<br>GATCAAACGAACTGTGGCTGCACCATCTGTCTTCATCTTCCCG<br>CCATCTGATGAGCAGTTGAAATCTGGAACTGCCTCTGTCGTGT<br>GCCTGCTGAATAACTTCTATCCCAGAGAGGCCAAAGTACAGT<br>GGAAGGTGGATAACGCCCTCCAATCGGGTAACTCCCAGGAGA |

TABLE 8-continued

CAR-T switch targeting polypeptides-Nucleotide Sequence

| NAME | SEQ ID NO | SEQUENCE |
|---|---|---|
| | | GTGTCACAGAGCAGGACAGCAAGGACAGCACCTACAGCCTCA<br>GCAGCACCCTGACGCTGAGCAAAGCAGACTACGAGAAACACA<br>AAGTCTACGCCTGCGAAGTCACCCATCAGGGCCTGTCCTCGCC<br>CGTCACAAAGAGCTTCAACAGGGGAGAGTGT |
| Heavy Chain of Rituximab (anti-CD20) | 14 | ATGAAAAAGAATATCGCATTTCTTCTTGCATCTATGTTCGTTTT<br>TTCTATTGCTACAAACGCGTACGCTCAGGTGCAGCTGCAGCAG<br>CCGGGCGCGGAACTGGTGAAACCGGGCGCGAGCGTGAAAATG<br>AGCTGCAAAGCGAGCGGCTATACCTTTACCAGCTATAACATG<br>CATTGGGTGAAACAGACCCCGGGCCGCGGCCTGGAATGGATT<br>GGCGCGATTTATCCGGGCAACGGCGATACCAGCTATAACCAG<br>AAATTTAAAGGCAAAGCGACCCTGACCGCGGATAAAAGCAGC<br>AGCACCGCGTATATGCAGCTGAGCAGCCTGACCAGCGAAGAT<br>AGCGCGGTGTATTATTGCGCGCGCAGCACCTATTATGGCGGCG<br>ATTGGTATTTTAACGTGTGGGGCGCGGGCACCACCGTGACCGT<br>GAGCGCGGCGAGCACCAAGGGCCCATCGGTCTTCCCCCTGGC<br>ACCCTCCTCCAAGAGCACCTCTGGGGGCACAGCGGCCCTGGG<br>CTGCCTGGTCAAGGACTACTTCCCCGAACCGGTGACGGTGTCG<br>TGGAACTCAGGCGCCCTGACCAGCGGCGTGCACACCTTCCCG<br>GCTGTCCTACAGTCCTCAGGACTCTACTCCCTCAGCAGCGTGG<br>TGACTGTGCCCTCTAGCAGCTTGGGCACCCAGACCTACATCTG<br>CAACGTGAATCACAAGCCCAGCAACACCAAGGTGGACAAGAA<br>AGTTGAGCCCAAATCTTGTGACAAAACTCACACA |
| Light chain of Clone C225 (anti-EGFR) | 15 | ATGAGGGTCCCCGCTCAGCTCCTGGGGCTCCTGCTGCTCTGGC<br>TCCCAGGTGCACGATGTGACATCGTTGCTGACCCAGTCCCCGT<br>GATCCTGTCCGTGTCCCCTGGCGAGCGGGTGTCCTTCTCCTGC<br>CGGGCCTCCCAGTCCATCGGCACCAACATCCACTGGTATCAGC<br>AGCGGACCAACGGCTCCCCTCGGCTGCTGATCAAGTACGCCTC<br>CGAGTCTATCTCCGGCATCCCTTCCCGGTTCTCCGGCTCCGGC<br>TCTGGCACCGACTTCACCCTGTCCATCAACTCCGTGGAGTCCG<br>AGGATATCGCCGACTACTACTGCCAGCAGAACAACAACTGGC<br>CTACCACCTTCGGCGCTGGAACCAAGCTGGAGCTGAAGCGTA<br>CGGTGGCTGCACCATCTGTCTTCATCTTCCCGCCATCTGATGA<br>GCAGTTGAAATCTGGAACTGCCTCTGTTGTGTGCCTGCTGAAT<br>AACTTCTATCCCAGAGAGGCCAAAGTACAGTGGAAGGTGGAT<br>AACGCCCTCCAATCGGGTAACTCCCAGGAGAGTGTCACAGAG<br>CAGGACAGCAAGGACAGCACCTACAGCCTCAGCAGCACCCTG<br>ACGCTGAGCAAAGCAGACTACGAGAAACACAAAGTCTACGCC<br>TGCGAAGTCACCCATCAGGGCCTGAGCTCGCCCGTCACAAAG<br>AGCTTCAACAGGGGAGAGTGTTGATGA |
| Heavy chain of Clone C225 (anti-EGFR) | 16 | ATGGGTTGGAGCCTCATCTTGCTCTTCCTTGTCGCTGTTGCTAC<br>GCGTGTCCACTCCCAGGTGCAGCTGAAGCAGTCCGGCCCTGG<br>CCTGGTGCAGCCTTCCCAGTCCCTGTCCATCACCTGCACCGTG<br>TCCGGCTTCTCCCTGACCAACTACGGCGTGCACTGGGTGCGCC<br>AGTCCCCCGGCAAGGGCCTGGAGTGGCTGGGCGTGATCTGGT<br>CCGGCGGCAACACCGACTACAACACCCCTTTCACCTCCCGGCT<br>GTCCATCAACAAGGACAACTCCAAGTCCCAGGTGTTCTTCAAG<br>ATGAACTCCCTGCAGTCCAACGACACCGCCATCTACTACTGCG<br>CCAGAGCCCTGACCTACTATGACTACGAGTTCGCCTACTGGGG<br>CCAGGGCACCCTGGTGACCGTGTCCGCCGCTAGCACCAAGGG<br>CCCATCGGTCTTCCCCCTGGCACCCTCCTCCAAGAGCACCTCT<br>GGGGGCACAGCGGCCCTGGGCTGCCTGGTCAAGGACTACTTC<br>CCCGAACCGGTGACGGTGTCGTGGAACTCAGGCGCCCTGACC<br>AGCGGCGTGCACACCTTCCCGGCTGTCCTACAGTCCTCAGGAC<br>TCTACTCCCTCAGCAGCGTGGTGACCGTGCCCTCCAGCAGCTT<br>GGGCACCCAGACCTACATCTGCAACGTGAATCACAAGCCCAG<br>CAACACCAAGGTGGACAAGAAAGTTGAGCCCAAATCTTGTGA<br>CAAAACTCACACATGCCCACCGTGCCCA |
| Light chain of anti-CLL-1 antibody | 17 | GAGAACGTGCTCACCCAATCCCCCGCCATTATGTCCGCCTCCC<br>CAGGCGAAAAGGTGACAATGACCTGCAGGGCCAGCTCCAACG<br>TGATCAGCTCTTACGTGCACTGGTACCAGCAACGGTCCGGCGC<br>CTCCCCTAAGCTGTGGATCTATAGCACAAGCAACCTGGCTTCC<br>GGCGTGCCTGCACGGTTCAGCGGAAGCGGAAGCGGAACAAGT<br>TACTCCCTCACCATTTCTAGCGTTGAAGCCGAGGATGCCGCTA<br>CATACTATTGTCAACAGTACAGCGGATACCCCCTGACCTTCGG<br>AGCCGGCACAAAACTGGAGCTCAAGAGAGCAGCTGCAGCTCC<br>CAGCGTGTTCATTTTTCCTCCCTCCGACGAACAACTGAAAAGC<br>GGAACAGCCTCTGTCGTTTGCCTGTTGAACAATTTCTACCCTA<br>GGGAGGCCAAGGTCCAGTGGAAAGTGGATAACGCTCTGCAAA<br>GCGGAAATTCTCAGGAAAGCGTTACCGAACAGGATTCTAAGG |

TABLE 8-continued

CAR-T switch targeting polypeptides-Nucleotide Sequence

| NAME | SEQ ID NO | SEQUENCE |
|---|---|---|
| | | ACTCTACATACTCTCTGTCTAGCACACTCACGCTGAGCAAAGC<br>AGACTACGAGAAACACAAAGTCTACGCCTGCGAAGTCACCCA<br>TCAGGGCCTGTCCTCGCCCGTCACAAAGAGCTTCAACAGGGG<br>AGAGTGT |
| Heavy chain of anti-CLL-1 antibody | 18 | GACATCCAGCTGCAGGAGAGCGGCCCCGGCCTGGTGAAGCCC<br>AGCCAGAGCCTGAGCCTGACCTGCAGCGTGACCGGCTACAGC<br>ATCACCAGCGCCTATTACTGGAACTGGATCCGGCAGTTCCCCG<br>GCAACAAGCTGGAGTGGATGGGCTACATCAGCTACGACGGCC<br>GGAACAACTACAACCCAAGCCTGAAGAACCGGATCAGCATCA<br>CCCGGGACACCAGCAAGAACCAGTTTTTCCTGAAGCTGAACA<br>GCGTGACCACAGAGGACACCGCCACCTATTACTGCGCCAGG<br>AGGGAGACTACGACGTGGGCAACTACTACGCCATGGACTACT<br>GGGGCCAGGGCACCAGCGTGACCGTGTCTAGCGCCCGGACCA<br>AGGGCCCCAGCGTGTTCCCCCTGGCCCCCAGCTCTAAGAGCAC<br>CAGCGGCGGAACCGCCGCTCTGGGCTGCCTGGTGAAGGACTA<br>CTTCCCCGAGCCCGTGACCGTGAGCTGGAACAGCGGCGCCCT<br>GACCAGCGGCGTGCACACCTTCCCCGCCGTGCTGCAGAGCTCT<br>GGCCTGTACAGCCTGAGCAGCGTGGTTACCGTGCCCAGTTCTT<br>CCCTGGGCACCCAGACCTACATCTGCAACGTGAACCACAAGC<br>CCAGCAACACCAAGGTGGACAAGAAAGTGGAGCCCAAGAGC<br>TGC |
| Light chain of anti-CD33 antibody | 19 | GATATTCAGATGACCCAGAGCCCGAGCAGCCTGAGCGCGAGC<br>GTGGGCGATCGCGTGACCATTACCTGCCGCGCGAGCGAAAGC<br>GTGGATAACTATGGCATTAGCTTTATGAACTGGTTTCAGCAGA<br>AACCGGGCAAAGCGCCGAAACTGCTGATTTATGCGGCGAGCA<br>CCAGGGCAGCGGCGTGCCGAGCCGCTTTAGCGGCAGCGGCA<br>GCGGCACCGATTTTACCCTGAACATTAGCAGCCTGCAGCCGG<br>ATGATTTTGCGACCTATTATTGCCAGCAGAGCAAAGAAGTGCC<br>GTGGACCTTTGGCCAGGGCACCAAAGTGGAAATTAAACGAAC<br>TGTGGCTGCACCATCTGTCTTCATCTTCCCGCCATCTGATGAG<br>CAGTTGAAATCTGGAACTGCCTCTGTTGTGTGCCTGCTGAATA<br>ACTTCTATCCCAGAGAGGCCAAAGTACAGTGGAAGGTGGATA<br>ACGCCCTCCAATCGGGTAACTCCCAGGAGAGTGTCACAGAGC<br>AGGACAGCAAGGACAGCACCTACAGCCTCAGCAGCACCCTGA<br>CGCTGAGCAAAGCAGACTACGAGAAACACAAAGTCTACGCCT<br>GCGAAGTCACCCATCAGGGCCTGAGCTCGCCCGTCACAAAGA<br>GCTTCAACAGGGGAGAGTGT |
| Heavy chain of anti-CD33 antibody | 20 | CAGGTGCAGCTGGTGCAGAGCGGCGCGGAAGTGAAAAAACCG<br>GGCAGCAGCGTGAAAGTGAGCTGCAAAGCGAGCGGCTATACC<br>TTTACCGATTATAACATGCATTGGGTGCGCCAGGCGCCGGGCC<br>AGGGCCTGGAATGGATTGGCTATATTTATCCGTATAACGGCGG<br>CACCGGCTATAACCAGAAATTTAAAAGCAAAGCGACCATTAC<br>CGCGGATGAAAGCACCAACACCGCGTATATGGAACTGAGCAG<br>CCTGCGCAGCGAAGATACCGCGGTGTATTATTGCGCGCGCGG<br>CCGCCCCGGCGATGGATTATTGGGGCCAGGGCACCCTGGTGAC<br>CGTGAGCAGCGCCTCCACCAAGGGCCCATCGGTCTTCCCCCTG<br>GCACCCTCCTCCTAGAGCACCTCTGGGGGCACAGCGGCCCTG<br>GGCTGCCTGGTCAAGGACTACTTCCCCGAACGGTGACGGTGT<br>CGTGGAACTCAGGCGCCCTGACCAGCGGCGTGCACACCTTCC<br>CGGCTGTCCTACAGTCCTCAGGACTCTACTCCCTCAGCAGCGT<br>GGTGACCGTGCCCTCCAGCAGCTTGGGCACCCAGACCTACATC<br>TGCAACGTGAATCACAAGCCCAGCAACACCAAGGTCGACAAG<br>AAAGTTGAGCCCAAATCTTGTGGTGGCGGTCACCATCACCATC<br>ATCACCACCAC |

TABLE 9

CAR-T switch targeting polypeptides -Amino Acid Sequence

| NAME | SEQ ID NO | SEQUENCE |
|---|---|---|
| Light chain of wildtype anti-CS1 antibody | 21 | DIQMTQSPSSLSASVGDRVTITCKASQDVGIAVAWYQQKPG<br>KVPKLLIYWASTRHTGVPDRFSGSGSGTDFTLTISSLQPEDV<br>ATYYCQQYSSYPYTFGQGTKLEIK |

TABLE 9-continued

CAR-T switch targeting polypeptides -Amino Acid Sequence

| NAME | SEQ ID NO | SEQUENCE |
|---|---|---|
| Heavy chain of wildtype anti-CS1 antibody Fab | 22 | EVQLVESGGGLVQPGGSLRLSCAASGFDFSRYWMSWVRQ APGKGLEWIGEINPDSSTINYAPSLKDKFIISRDNAKNSLYLQ MNSLRAEDTAVYYCARPDGNYWYFDVWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSC |
| Light chain of anti-EGFRvIII antibody (Hu806) Fab | 23 | DIQMTQSPSSMSVSVGDRVTITCHSSQDINSNIGWLQQKPGK SFKGLIYHGTNLDDGVPSRFSGSGSGTDYTLTISSLQPEDFAT YYCVQYAQFPWTFGGGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKS FNRGEC |
| Heavy chain of anti-EGFRvIII antibody (Hu806) Fab | 24 | QLQESGPGLVKPSQTLSLTCTVSGYSISSDFAWNWIRQPPGK GLEWMGYISYSGNTRYQPSLKSRITISRDTSKNQFFLKLNSV TAADTATYYCVTAGRGFPYWGQGTLVTVSSASTKGPSVFP LAPSSKSTSGGTAALGCLVKDYFPEPVTVSWNSGALTSGVH TFPAVLQSSGLYSLSSVVTVPSSSLGTQTYICNVNHKPSNTK VDKKVEPKSC |
| Light chain of anti-BCMA antibody (BCMA98) Fab | 25 | DIQMTQSPSSLSASVGDRVTITCRANQGISNNLNWYQQKPG KAPKPLIYYTSNLQSGVPSRFSGSGSGTDYTLTISSLQPEDFA TYYCQQFTSLPYTFGQGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKS FNRGEC |
| Heavy chain of anti-BCMA antibody (BCMA98) Fab | 26 | EVQLVESGGGLVQPGGSLRLSCAASGFTFSNFDMAWVRQA PGKGLVWVSSITTGGGDTYYADSVKGRFTISRDNAKSTLYL QMDSLRSEDTAVYYCVRHGYYDGYHLFDYWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSC |
| Light Chain of anti-CD19 antibody | 27 | DIQMTQTTSSLSASLGDRVTISCRASQDISKYLNWYQQKPD GTVKLLIYHTSRLHSGVPSRFSGSGSGTDYSLTISNLEQEDIA TYFCQQGNTLPYTFGGGTKLEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC |
| Heavy Chain of anti-CD19 antibody IgG | 28 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSCDKTHTCPPCPAPPVAGPSVFLFPP KPKDTLMISRTPEVTCVVVDVSHEDPEVKFNWYVDGVEVH NAKTKPREEQYNSTYRVVSVLTVLHQDWLNGKEYKCKVS NKGLPSSIEKTISKAKGQPREPQVYTLPPSRDELTKNQVSLT CLVKGFYPSDIAVEWESNGQPENNYKTTPPVLDSDGSFFLY SKLTVDKSRWQQGNVFSCSVMHEALHNHYTQKSLSLSPGK |
| Heavy Chain of anti-CD19 antibody Fab | 29 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSC |

TABLE 10

CAR-T switches-Amino Acid Sequence

| NAME | SEQ ID NO | SEQUENCE |
|---|---|---|
| anti-CD19 Fab CL1-GCN4 switch Light Chain | 30 | DIQMTQTTSSLSASLGDRVTISCRASQDISKYLNWYQQKPD GTVKLLIYHTSRLHSGVPSRFSGSGSGTDYSLTISNLEQEDIA TYFCQQGNTLPYTFGGGTKLEIKRTVAAPSVFIFPPSDEQLK SGTASVVCLLNNFYPREAKVQWKVDNALQSGNSQESVTEQ DSGGGGSNYHLENEVARLKKLGGGGSDSTYSLSSTLTLS KADYEKHKVYACEVTHQGLSSPVTKSFNRGEC |

TABLE 10-continued

CAR-T switches-Amino Acid Sequence

| NAME | SEQ ID NO | SEQUENCE |
|---|---|---|
| anti-CD19 IgG CL1-GCN4 switch Light Chain | 31 | DIQMTQTTSSLSASLGDRVTISCRASQDISKYLNWYQQKPD GTVKLLIYHTSRLHSGVPSRFSGSGSGTDYSLTISNLEQEDIA TYFCQQGNTLPYTFGGGTKLEIKRTVAAPSVFIFPPSDEQLK SGTASVVCLLNNFYPREAKVQWKVDNALQSGNSQESVTEQ DSGGGGSNYHLENEVARLKKLGGGGSDSTYSLSSTLTLS KADYEKHKVYACEVTHQGLSSPVTKSFNRGEC |
| anti-CD19 Fab HC1-GCN4 switch Heavy Chain | 32 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSNYHLENEVARLKKLSGGTAALGCLVKD YFPEPVTVSWNSGALTSGVHTFPAVLQSSGLYSLSSVVTVPS SSLGTQTYICNVNHKPSNTKVDKKVEPKSC |
| anti-CD19 IgG HC1-GCN4 switch Heavy Chain | 33 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSNYHLENEVARLKKLSGGTAALGCLVKD YFPEPVTVSWNSGALTSGVHTFPAVLQSSGLYSLSSVVTVPS SSLGTQTYICNVNHKPSNTKVDKKVEPKSCDKTHTCPPCPA PPVAGPSVFLFPPKPKDTLMISRTPEVTCVVVDVSHEDPEVK FNWYVDGVEVHNAKTKPREEQYNSTYRVVSVLTVLHQDW LNGKEYKCKVSNKGLPSSIEKTISKAKGQPREPQVYTLPPSR DELTKNQVSLTCLVKGFYPSDIAVEWESNGQPENNYKTTPP VLDSDGSFFLYSKLTVDKSRWQQGNVFSCSVMHEALHNHY TQKSLSLSPGK |
| anti-CD19 Fab C term-GCN4 switch Heavy Chain | 34 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSCGGGGSNYHLENEVARLKKL |
| anti-CD19 IgG hinge-GCN4 switch Heavy Chain | 35 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSCGGGGSNYHLENEVARLKKLG GSDKTHTCPPCPAPPVAGPSVFLFPPKPKDTLMISRTPEVTC VVVDVSHEDPEVKFNWYVDGVEVHNAKTKPREEQYNSTY RVVSVLTVLHQDWLNGKEYKCKVSNKGLPSSIEKTISKAKG QPREPQVYTLPPSRDELTKNQVSLTCLVKGFYPSDIAVEWES NGQPENNYKTTPPVLDSDGSFFLYSKLTVDKSRWQQGNVF SCSVMHEALHNHYTQKSLSLSPGK |
| anti-CD19 Fab CL1 N-term Light Chain | 36 | NYHLENEVARLKKLGGGGSDIQMTQTTSSLSASLGDRVTI SCRASQDISKYLNWYQQKPDGTVKLLIYHTSRLHSGVPSRF SGSGSGTDYSLTISNLEQEDIATYFCQQGNTLPYTFGGGTKL EIKRTVAAPSVFIFPPSDEQLKSGTASVVCLLNNFYPREAKV QWKVDNALQSGNSQESVTEQDSKDSTYSLSSTLTLSKADYE KHKVYACEVTHQGLSSPVTKSFNRGEC |
| anti-BCMA GCN4 CL1 light chain | 37 | DIQMTQSPSSLSASVGDRVTITCRANQGISNNLNWYQQKPG KAPKPLIYYTSNLQSGVPSRFSGSGSGTDYTLTISSLQPEDFA TYYCQQFTSLPYTFGQGTKLEIKRTVAAPSVFIFPPSDEQLKS GTASVVCLLNNFYPREAKVQWKVDNALQSGNSQESVTEQD SGGGGSNYHLENEVARLKKLGGGGSDSTYSLSSTLTLSK ADYEKHKVYACEVTHQGLSSPVTKSFNRGEC |
| anti-BCMA heavy chain WT IgG | 38 | EVQLVESGGGLVQPGGSLRLSCAASGFTFSNFDMAWVRQA PGKGLVWVSSITTGGGDTYYADSVKGRFTISRDNAKSTLYL QMDSLRSEDTAVYYCVRHGYYDGYHLFDYWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPPVAGPSVFL FPPKPKDTLMISRTPEVTCVVVDVSHEDPEVKFNWYVDGVE VHNAKTKPREEQYNSTYRVVSVLTVLHQDWLNGKEYKCK VSNKGLPSSIEKTISKAKGQPREPQVYTLPPSRDELTKNQVS LTCLVKGFYPSDIAVEWESNGQPENNYKTTPPVLDSDGSFF LYSKLTVDKSRWQQGNVFSCSVMHEALHNHYTQKSLSLSP GK |

Bold indicates grafted region (peptide and/or linker(s)).
Underline indicates peptide.

TABLE 11 pBAD vector with CAR-T targeting moiety -Nucleotide Sequence

| SEQ NAME | ID NO | SEQUENCE |
|---|---|---|
| pBAD-CD19wt | 39 | AAGAAACCAATTGTCCATATTGCATCAGACATTGCCGTC<br>ACTGCGTCTTTTACTGGCTCTTCTCGCTAACCAAACCGGT<br>AACCCTGATTATTTGCACGGAGTCACACTTTGCTATGCCA<br>TAGCATTTTTATCCATAAGATTAGCGGATCCTACCTGACG<br>CTTTTTATCGCAACTCTCTACTGTTTCTCCATACCCGTTTT<br>TTTGGGCTAGAAATAATTTTGTTTAACTTTAAGAAGGAGA<br>ATACATCAACTAGTACGCAAGTTCACGTAAAAAGGGTAT<br>CTAGAGGTTGAGGTGATTTATGAAAAAGAATATCGCAT<br>TTCTTCTTGCTAGCATGTTCGTTTTTTCTATTGCTACAAAC<br>GCATACGCTGACATCCAGATGACACAGACTACATCCTCC<br>CTGTCTGCCTCTCTGGGAGACAGAGTCACCATCAGTTGCA<br>GGGCAAGTCAGGACATTAGTAAATATTTAAATTGGTATC<br>AGCAGAAACCAGATGGAACTGTTAAACTCCTGATCTACC<br>ATACATCAAGATTACACTCAGGAGTCCCATCAAGGTTCA<br>GTGGCAGTGGGTCTGGAACAGATTATTCTCTCACCATTAG<br>CAACCTGGAGCAAGAAGATATTGCCACTTACTTTTGCCA<br>ACAGGGTAATACGCTTCCGTACACGTTCGGAGGGGGGAC<br>CAAGCTTGAGATCAAACGAACTGTGGCTGCACCATCTGT<br>CTTCATCTTCCCGCCATCTGATGAGCAGTTGAAATCTGGA<br>ACTGCCTCTGTCGTGTGCCTGCTGAATAACTTCTATCCCA<br>GAGAGGCCAAAGTACAGTGGAAGGTGGATAACGCCCTCC<br>AATCGGGTAACTCCCAGGAGAGTGTCACAGAGCAGGACA<br>GCAAGGACAGCACCTACAGCCTCAGCAGCACCCTGACGC<br>TGAGCAAAGCAGACTACGAGAAACACAAAGTCTACGCCT<br>GCGAAGTCACCCATCAGGGCCTGTCCTCGCCCGTCACAA<br>AGAGCTTCAACAGGGGAGAGTGTTAAGCTGGGGATCCTC<br>TAGAGGTTGAGGTGATTTTATGAAAAAGAATATCGCATT<br>TCTTCTTGCATCTATGTTCGTTTTTTCTATTGCTACAAACG<br>CGTACGCTGAGGTGAAACTGCAGGAGTCAGGACCTGGCC<br>TGGTGGCGCCCTCACAGAGCCTGTCCGTCACATGCACTGT<br>CTCAGGGGTCTCATTACCCGACTATGGTGTAAGCTGGATT<br>CGCCAGCCTCCACGAAAGGGTCTGGAGTGGCTGGGAGTA<br>ATATGGGGTAGTGAAACCACATACTATAATTCAGCTCTC<br>AAATCCAGACTGACCATCATCAAGGACAACTCCAAGAGC<br>CAAGTTTTCTTAAAAATGAACAGTCTGCAAACTGATGAC<br>ACAGCCATTTACTACTGTGCCAAACATTATTACTACGGTG<br>GTAGCTATGCTATGGACTACTGGGGCCAAGGAACCTCAG<br>TCACCGTCTCCTCAGCCTCCACCAAGGGCCCATCGGTCTT<br>CCCCCTGGCACCCTCCTCCAAGAGCACCTCTGGGGGCAC<br>AGCGGCCCTGGGCTGCCTGGTCAAGGACTACTTCCCCGA<br>ACCGGTGACGGTGTCGTGGAACTCAGGCGCCCTGACCAG<br>CGGCGTGCACACCTTCCCGGCTGTCCTACAGTCCTCAGGA<br>CTCTACTCCCTCAGCAGCGTGGTGACTGTGCCCTCTAGCA<br>GCTTGGGCACCCAGACCTACATCTGCAACGTGAATCACA<br>AGCCCAGCAACACCAAGGTGGACAAGAAAGTTGAGCCC<br>AAATCTTGTGACAAAACTCACACATAATAAGTCGACCGA<br>TGCCCTTGAGAGCCTTCAACCCAGTCAGCTCCTTCCGGTG<br>GGCGCGGGGCATGACTATCGTCGCCGCACTTATGACTGT<br>CTTCTTTATCATGCAACTCGTAGGACAGGTGCCAAACGGT<br>CTCCAGCTTGGCTGTTTTGGCGGATGAGAAGATTTTCA<br>GCCTGATACAGGATTCAGAACGCAGAAGCGTCTGA<br>TAAAACAGAATTTGCCTGGCGGCAGTAGCGCGGTGGTCC<br>CACCTGACCCCATGCCGAACTCAGAAGTGAAACGCCGTA<br>GCGCCGATGGTAGTGTGGGGTCTCCCCATGCGAGAGTAG<br>GGAACTGCCAGGCATCAAATAAAACGAAAGGCTCAGTCG<br>AAAGACTGGGCCTTTCGTTTTATCTGTTGTTTGTCGGTGA<br>ACGCTCTCCTGAGTAGGACAAATCCGCCGGGAGCGGATT<br>TGAACGTTGCGAAGCAACGGCCCGGAGGGTGGCGGGCA<br>GGACGCCCGCCATAAACTGCCAGGCATCAAATTAAGCAG<br>AAGGCCATCCTGACGGATGGCCTTTTTGCGTTTCTACAAA<br>CTCTTTTTGTTTATTTTTCTAAATACATTCAAATATGTATC<br>CGCTCATGAGACAATAACCCTGATAAATGCTTCAATAAT<br>ATTGAAAAGGAAGAGTATGAGTATTCAACATTTCCGTG<br>TCGCCCTTATTCCCTTTTTTGCGGCATTTTGCCTTCCTGTT<br>TTTGCTCACCCAGAAACGCTGGTGAAAGTAAAAGATGCT<br>GAAGATCAGTTGGGTGCACGAGTGGGTTACATCGAACTG<br>GATCTCAACAGCGGTAAGATCCTTGAGAGTTTTCGCCCC<br>GAAGAACGTTTTCCAATGATGAGCACTTTTAAAGTTCTGC<br>TATGTGGCGCGGTATTATCCCGTGTTGACGCCGGGCAAG<br>AGCAACTCGGTCGCCGCATACACTATTCTCAGAATGACTT<br>GGTTGAGTACTCACCAGTCACAGAAAAGCATCTTACGGA<br>TGGCATGACAGTAAGAGAATTATGCAGTGCTGCCATAAC<br>CATGAGTGATAACACTGCGGCCAACTTACTTCTGACAAC |

GATCGGAGGACCGAAGGAGCTAACCGCTTTTTTGCACAA<br>CATGGGGGATCATGTAACTCGCCTTGATCGTTGGGAACC<br>GGAGCTGAATGAAGCCATACCAAACGACGAGCGTGACA<br>CCACGATGCCTGTAGCAATGGCAACAACGTTGCGCAAAC<br>TATTAACTGGCGAACTACTTACTCTAGCTTCCCGGCAACA<br>ATTAATAGACTGGATGGAGGCGGATAAAGTTGCAGGACC<br>ACTTCTGCGCTCGGCCCTTCCGGCTGGCTGGTTTATTGCT<br>GATAAATCTGGAGCCGGTGAGCGTGGGTCTCGCGGTATC<br>ATTGCAGCACTGGGGCCAGATGGTAAGCCCTCCCGTATC<br>GTAGTTATCTACACGACGGGGAGTCAGGCAACTATGGAT<br>GAACGAAATAGACAGATCGCTGAGATAGGTGCCTCACTG<br>ATTAAGCATTGGTAACTGTCAGACCAAGTTTACTCATATA<br>TACTTTAGATTGATTTAAAACTTCATTTTTAATTTAAAAG<br>GATCTAGGTGAAGATCCTTTTTGATAATCTCATGACCAAA<br>ATCCCTTAACGTGAGTTTTCGTTCCACTGAGCGTCAGACC<br>CCGTAGAAAAGATCAAAGGATCTTCTTGAGATCCTTTTTT<br>TCTGCGCGTAATCTGCTGCTTGCAAACAAAAAAACCACC<br>GCTACCAGCGGTGGTTTGTTTGCCGGATCAAGAGCTACC<br>AACTCTTTTTCCGAAGGTAACTGGCTTCAGCAGAGCGCA<br>GATACCAAATACTGTCCTTCTAGTGTAGCCGTAGTTAGGC<br>CACCACTTCAAGAACTCTGTAGCACCGCCTACATACCTCG<br>CTCTGCTAATCCTGTTACCAGTGGCTGCTGCCAGTGGCGA<br>TAAGTCGTGTCTTACCGGGTTGGACTCAAGACGATAGTT<br>ACCGGATAAGGCGCAGCGGTCGGGCTGAACGGGGGGTTC<br>GTGCACACAGCCCAGCTTGGAGCGAACGACCTACACCGA<br>ACTGAGATACCTACAGCGTGAGCTATGAGAAAGCGCCAC<br>GCTTCCCGAAGGGAGAAAGGCGGACAGGTATCCGGTAA<br>GCGGCAGGGTCGGAACAGGAGAGCGCACGAGGGAGCTT<br>CCAGGGGGAAACGCCTGGTATCTTTATAGTCCTGTCGGG<br>TTTCGCCACCTCTGACTTGAGCGTCGATTTTTGTGATGCT<br>CGTCAGGGGGGCGGAGCCTATGGAAAAACGCCAGCAAC<br>GCGGCCTTTTTACGGTTCCTGGCCTTTTGCTGGCCTTTTGC<br>TCACATGTTCTTTCCTGCGTTATCCCCTGATTCTGTGGATA<br>ACCGTATTACCGCCTTTGAGTGAGCTGATACCGCTCGCCG<br>CAGCCGAACGACCGAGCGCAGCGAGTCAGTGAGCGAGG<br>AAGCGGAAGAGCGCCTGATGCGGTATTTTCTCCTTACGC<br>ATCTGTGCGGTATTTCACACCGCATATGGTGCACTCTCAG<br>TACAATCTGCTCTGATGCCGCATAGTTAAGCCAGTATACA<br>CTCCGCTATCGCTACGTGACTGGGTCATGGCTGCGCCCCG<br>ACACCCGCCAACACCCGCTGACGCGCCCTGACGGGCTTG<br>TCTGCTCCCGGCATCCGCTTACAGACAAGCTGTGACCGTC<br>TCCGGGAGCTGCATGTGTCAGAGGTTTTCACCGTCATCAC<br>CGAAACGCGCGAGGCAGCAGATCAATTCGCGCGCGAAG<br>GCGAAGCGGCATGCATAATGTGCCTGTCAAATGGACGAA<br>GCAGGGATTCTGCAAACCCTATGCTACTCCGTCAAGCCG<br>TCAATTGTCTGATTCGTTACCAATTATGACAACTTGACGG<br>CTACATCATTCACTTTTTCTTCACAACCGGCACGGAACTC<br>GCTCGGGCTGGCCCCGGTGCATTTTTTAAATACCCGCGAG<br>AAATAGACTTGATCGTCAAAACCAACATTGCGACCGACG<br>GTGGCGATAGGCATCCGGGTGGTGCTCAAAAGCAGCTTC<br>GCCTGGCTGATACGTTGGTCCTCGCGCCAGCTTAAGACG<br>CTAATCCCTAACTGCTGGCGGAAAAGATGTGACAGACGC<br>GACGGCGACAAGCAAACATGCTGTGCGACGCTGGCGATA<br>TCAAAATTGCTGTCTGCCAGGTGATCGCTGATGTACTGAC<br>AAGCCTCGCGTACCCGATTATCCATCGGTGGATGGAGCG<br>ACTCGTTAATCGCTTCCATGCGCCGCAGTAACAATTGCTC<br>AAGCAGATTTATCGCCAGCAGCTCCGAATAGCGCCCTTC<br>CCCTTGCCCGGCGTTAATGATTTGCCCAAACAGGTCGCTG<br>AAATGCGGCTGGTGCGCTTCATCCGGGCGAAAGAACCCC<br>GTATTGGCAAATATTGACGGCCAGTTAAGCCATTCATGC<br>CAGTAGGCGCGCGGACGAAAGTAAACCCACTGGTGATAC<br>CATTCGCGAGCCTCCGGATGACGACCGTAGTGATGAATC<br>TCTCCTGGCGGGAACAGCAAAATATCACCCGGTCGGCAA<br>ACAAATTCTCGTCCCTGATTTTTCACCACCCCCTGACCGC<br>GAATGGTGAGATTGAGAATATAACCTTTCATTCCCAGCG<br>GTCGGTCGATAAAAAAATCGAGATAACCGTTGGCCTCAA<br>TCGGCGTTAAACCCGCCACCAGATGGGCATTAAACGAGT<br>ATCCCGGCAGCAGGGGATCATTTTGCGCTTCAGCCATACT<br>TTTCATACTCCCGCCATTCAGAG

TABLE 12

| NAME | SEQ ID NO | SEQUENCE |
|---|---|---|
| | 40 | (GGGGS)$_n$, n is at least 1 |
| | 41 | (GGGS)$_n$, n is at least 1 |
| | 42 | (GGS)$_n$, n is at least 1 |
| | 43 | (G$_m$S)$_n$, n is at least 1, m is at least 1 |

TABLE 12-continued

| NAME | SEQ ID NO | SEQUENCE |
|---|---|---|
| | 44 | (X$_m$S)$_n$, n is at least 1, m is least 1 and X is an amino acid |

Bold indicates grafted region (peptide and/or linker(s)).
Underline indicates peptide.

What is claimed is:

1. A kit comprising:
   a. a chimeric antigen receptor-effector cell switch comprising:
      i. a peptidic antigen comprising a yeast transcription factor GCN4 peptide that binds to and activates an anti-GCN4 chimeric antigen receptor on an effector cell; said GCN4 peptide comprising a portion of SEQ ID NO: 2 that is at least 12 amino acids; and
      ii. a targeting moiety that binds a cell surface molecule on a target cell; and
   b. a chimeric antigen receptor-effector cell comprising an anti-GNC4 chimeric antigen receptor that binds to the peptidic antigen of the chimeric antigen receptor-effector cell switch.

2. The kit of claim 1, wherein the binding of the chimeric antigen receptor-effector cell switch to the chimeric antigen receptor on an effector cell induces an immune response that is cytotoxic to the target cell also bound to the chimeric antigen receptor-effector cell switch.

3. The kit of claim 1, wherein the targeting moiety comprises a targeting peptide.

4. The kit of claim 1, wherein the targeting moiety comprises a targeting antibody or an antigen binding fragment of an antibody.

5. The kit of claim 4, wherein the targeting antibody or the antigen binding fragment of the antibody is selected from the group consisting of: an immunoglobulin, an Fc null immunoglobulin, a Fab, and antigen binding fragments thereof.

6. The kit of claim 4, wherein the targeting moiety is selected from the group consisting of: an anti-EGFR antibody, an anti-Her2 antibody, an anti-EGFRvIII antibody, an anti-CD33 antibody, an anti-CLL-1 antibody, an anti-CEA antibody, an anti-CD19 antibody, an anti-CD22 antibody, an anti-BCMA antibody, and an anti-CS1 antibody, and antigen binding fragments thereof.

7. The kit of claim 4, wherein the targeting antibody or the antigen binding fragment of the antibody comprises a light chain and a heavy chain pair, wherein the light chain and heavy chain are encoded by nucleic acid sequences comprising nucleic acid sequence pairs selected from the group consisting of: SEQ ID NOs: 8 and 9; SEQ ID NOs: 8 and 10; SEQ ID NOs: 11 and 12; SEQ ID NOs. 13 and 14; SEQ ID NOs: 15 and 16; SEQ ID NOs: 17 and 18; and SEQ ID NOs: 19 and 20.

8. The kit of claim 4, wherein the targeting antibody or the antigen binding fragment of the antibody comprises a light chain and a heavy chain pair, wherein the light chain and heavy chain comprise amino acid sequence pairs selected from the group consisting of: SEQ ID NOs: 21 and 22; SEQ ID NOs: 23 and 24; SEQ ID NOs. 25 and 26; SEQ ID NOs: 27 and 28; and SEQ ID NOs: 27 and 29.

9. The kit of claim 4, wherein the targeting antibody or the antigen binding fragment of the antibody comprises a light chain and a heavy chain pair, wherein the light chain and heavy chain comprise amino acid sequence pairs selected from the group consisting of: SEQ ID NOs: 30 and 29; SEQ ID NOs: 36 and 29; SEQ ID NOs: 31 and 28; SEQ ID NOs: 27 and 32; SEQ ID NOs: 27 and 33; SEQ ID NOs: 27 and 34; and SEQ ID NOs: 27 and 35.

10. The kit of claim 4, wherein the peptidic antigen is fused to a terminus of the targeting antibody or the antigen binding fragment of the antibody.

11. The kit of claim 4, wherein the peptidic antigen is fused to a region of the targeting antibody or antigen binding fragment of the antibody selected from the group consisting of: an N terminus of a light chain, a C terminus of a light chain, an N terminus of a heavy chain, a C terminus of a Fab heavy chain, and a C terminus of a heavy chain constant region.

12. The kit of claim 1, further comprising a linker that links the peptidic antigen and the targeting moiety.

13. The kit of claim 12, wherein the linker comprises about 1 to about 20 amino acids.

14. The kit of claim 12, wherein the linker comprises a sequence selected from SEQ ID NOs: 38-42.

15. The kit of claim 1, wherein the targeting moiety is selected from the group consisting of: an anti-Her2 antibody, an anti-BCMA antibody, an anti-CD19 antibody, an anti-CEA antibody, and antigen binding fragments thereof.

16. The kit of claim 1, wherein the target cell is a cancer cell.

17. The kit of claim 1, wherein the cell surface molecule is a tumor associated antigen.

18. The kit of claim 1, wherein the cell surface molecule is selected from the group consisting of: a cluster of differentiation protein, a receptor, an integral membrane protein and a glycoprotein.

19. The kit of claim 4, wherein the targeting antibody or antigen binding fragment of the antibody comprises a light chain and a heavy chain pair, wherein the light chain and heavy chain are encoded by nucleic acid sequences comprising nucleic acid sequence pairs selected from the group consisting of: SEQ ID NOs: 8 and 9; SEQ ID NOs: 8 and 10.

20. The kit of claim 4, wherein the targeting antibody or the antigen binding fragment of the antibody comprises a light chain and a heavy chain pair, wherein the light chain and heavy chain comprise amino acid sequence pairs selected from the group consisting of: SEQ ID NOs: 27 and 28; and SEQ ID NOs: 27 and 29.

21. The kit of claim 1, wherein the chimeric antigen receptor-effector cell switch comprises a light chain and a heavy chain pair, wherein the light chain and heavy chain comprise amino acid sequences of SEQ ID NOs: 36 and 29.

22. The kit of claim 1, wherein the yeast transcription factor GCN4 peptide comprises a sequence that is at least 85% identical to SEQ ID NO: 3.

23. The kit of claim 1, wherein the yeast transcription factor GCN4 peptide that binds to and activates the anti-GCN4 chimeric antigen receptor on an effector cell; said GCN4 peptide comprising a portion of SEQ ID NO: 2 that (i) is at least 12 amino acids (ii) is at least 85% identical to SEQ ID NO: 3; and (iii) that does not dimerize.

24. The kit of claim 23, wherein the targeting moiety comprises a targeting antibody or an antigen binding fragment of an antibody.

25. The kit of claim 24, wherein the targeting moiety is selected from the group consisting of: an anti-EGFR antibody, an anti-Her2 antibody, an anti-EGFRvIII antibody, an anti-CD33 antibody, an anti-CLL-1 antibody, an anti-CEA antibody, an anti-CD19 antibody, an anti-CD22 antibody, an anti-BCMA antibody, and an anti-CS1 antibody, and antigen binding fragments thereof.

* * * * *